(12) United States Patent
Altman et al.

(10) Patent No.: US 12,678,451 B2
(45) Date of Patent: *Jul. 14, 2026

(54) CANNABINOID AND OMEGA FATTY ACID COMPOSITIONS AND METHODS OF USING

(71) Applicant: GreenWay Herbal Products, LLC, Murfreesboro, TN (US)

(72) Inventors: Elliot Altman, Rockvale, TN (US); Matthew Fuller, Murfreesboro, TN (US); Gheda Alsaif, Hail (SA); Shannon Antoine Smith, Murfreesboro, TN (US); Karen Maynard, Murfreesboro, TN (US); Anthony Farone, Murfreesboro, TN (US)

(73) Assignee: GREENWAY HERBAL PRODUCTS, LLC, Nashville, TN (US)

( * ) Notice: Subject to any disclaimer, the term of this patent is extended or adjusted under 35 U.S.C. 154(b) by 589 days.

This patent is subject to a terminal disclaimer.

(21) Appl. No.: 18/164,044

(22) Filed: Feb. 3, 2023

(65) Prior Publication Data

US 2023/0248747 A1 Aug. 10, 2023

Related U.S. Application Data

(63) Continuation-in-part of application No. 17/931,249, filed on Sep. 12, 2022, which is a continuation-in-part of application No. 17/594,830, filed as application No. PCT/US2020/030777 on Apr. 30, 2020.

(60) Provisional application No. 62/840,972, filed on Apr. 30, 2019.

(51) Int. Cl.

| | |
|---|---|
| *A61K 31/00* | (2006.01) |
| *A61K 31/202* | (2006.01) |
| *A61K 45/06* | (2006.01) |
| *A61P 29/00* | (2006.01) |
| *A61P 39/06* | (2006.01) |

(52) U.S. Cl.
CPC .......... *A61K 31/658* (2023.05); *A61K 31/202* (2013.01); *A61K 45/06* (2013.01); *A61P 29/00* (2018.01); *A61P 39/06* (2018.01)

(58) Field of Classification Search
CPC ..... A61P 29/00; A61K 45/06; A61K 39/3955; A61K 31/05; A61K 31/60; A61K 31/201; A61K 31/352; A61K 31/573; A61K 31/658
See application file for complete search history.

(56) References Cited

U.S. PATENT DOCUMENTS

| | | | |
|---|---|---|---|
| 9,962,341 | B2 | 5/2018 | Stott et al. |
| 11,712,456 | B2 | 8/2023 | Howland et al. |
| 2014/0302086 | A1 | 10/2014 | Kelly |
| 2016/0228385 | A1 | 8/2016 | Sievers et al. |
| 2017/0143642 | A1 | 5/2017 | Stott et al. |
| 2018/0021438 | A1 | 1/2018 | Naheed |
| 2019/0111093 | A1 | 4/2019 | Siurkus et al. |
| 2019/0336471 | A1 | 11/2019 | DeMarco et al. |
| 2019/0374502 | A1 | 12/2019 | Jha |
| 2021/0275485 | A1 | 9/2021 | Rager |
| 2022/0249586 | A1 | 8/2022 | Howland et al. |
| 2023/0090094 | A1 | 3/2023 | Kjaer et al. |
| 2023/0285318 | A1 | 9/2023 | Kjaer et al. |
| 2024/0075087 | A1 | 3/2024 | Wakshlag |

FOREIGN PATENT DOCUMENTS

| | | | | |
|---|---|---|---|---|
| EP | 3449914 A1 | 3/2019 | | |
| GB | 2496688 A | 5/2013 | | |
| GB | 2527590 A | 12/2015 | | |
| GB | 2542797 A | 4/2017 | | |
| WO | 9952524 A1 | 10/1999 | | |
| WO | 2005072719 A1 | 8/2005 | | |
| WO | 2017025712 A1 | 2/2017 | | |
| WO | 2017177261 A1 | 10/2017 | | |
| WO | WO-2017178937 A1 * | 10/2017 | ........... | A61K 31/658 |
| WO | 2019199861 A2 | 10/2019 | | |
| WO | 2020223510 A1 | 11/2020 | | |
| WO | 2020/257875 A1 | 12/2020 | | |
| WO | 20220006413 A2 | 1/2022 | | |
| WO | 20220006413 A3 | 1/2022 | | |

OTHER PUBLICATIONS

Calder (Biochemical Society Transactions (2017) 45 1105-1115) (Year: 2017).*
Siddiquee (Immunopharmacology and Immunotoxicology 2019, vol. 41, No. 2, 250-257) (Year: 2019).*
Fava (Journal of Autoimmunity 96 (2019) 1-13) (Year: 2019).*
OâBrien (Cancers 2022, 14, 885. 1-24) (Year: 2022).*
Patent Cooperation Treaty, International Patent Application No. PCT/US2023/061944, "International Search Report and Written Opinion" dated May 24, 2023, 5 pages.
International Patent Application No. PCT/US2023/061944, "International Search Report and Written Opinion of the International Searching Authority," dated May 24, 2023.
U.K. Intellectual Property Office, GB Patent Application No. GB2304091.8, Examination Report under Section 18(3), Jul. 20, 2023.

(Continued)

*Primary Examiner* — Kortney L. Klinkel
*Assistant Examiner* — Richard Grant Peckham
(74) *Attorney, Agent, or Firm* — André J. Bahou; Luke R. Yordy; Bradley Arant Boult Cummings LLP

(57) ABSTRACT

This disclosure describes compositions including cannabinoids and omega fatty acids and methods of using those compositions including, for example, to treat or prevent inflammation, as an immunosuppressant, and/or as an anti-cancer therapeutic. In some aspects, the cannabinoid is chosen from i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA. In some aspects, the omega fatty acid is chosen from an omega-3 fatty acid (such as ALA, DHA, or EPA), an omega-7 fatty acid, or an omega-9 fatty acid.

16 Claims, 18 Drawing Sheets

(56) References Cited

OTHER PUBLICATIONS

U.K. Intellectual Property Office, GB Patent Application No. GB2115666.6, "Patents Act 1977: Report of telephone conversation between Kate Wilson and Examiner Dr. Bill Thomson held Mar. 7, 2023," Mar. 8, 2023, 2 pages.

U.K. Intellectual Property Office, GB Patent Application No. GB2115666.6, Examination Report under Section 18(3), Jan. 17, 2023.

U.K. Intellectual Property Office, GB Patent Application No. GB2115666.6, Examination Report under Section 18(3), Jan. 27, 2023.

Wirth, Philip W., et al., "Anti-inflammatory Properties of Cannabichromene," Life Sciences 26, pp. 1991-1995, Apr. 4, 1980.

U.K. Intellectual Property Office, GB Patent Application No. GB2304091.8, Combined Search and Examination Report under Section 18(3), May 4, 2023.

Fajgenbaum, David C., and June, Carl H., "Cytokine Storm," New England Journal of Medicine 383(23), pp. 2255-2273, Dec. 3, 2020.

Qian, Mengjia, et al., "Autophagy and Inflammation," Clinical and Translational Medicine 6(24), pp. 1-11, Dec. 2017.

Gerlach, Herwig, "Agents to Reduce Cytokine Storm," F1000Research 5(2909), pp. 1-8, Dec. 22, 2016.

Canadian Intellectual Property Office; Canadian Patent Application No. 3,132, 856; Examination Report dated Jan. 12, 2024, 5 pages.

Fava, Andrea et al., "Systemic lupus erythematosus: Diagnosis and clinical management," Journal of Autoimmunity, vol. 96, Jan. 2019, Elsevier, pp. 1-13. doi: 10.1016/j.jaut.2018.11.001.

Israeli Patent Office, Israeli Patent Application No. 287456, Examination Report dated Jun. 30, 2024, 5 pages.

Katz, Daphna et al., "Cannabidiol as a Therapy for ASIA Syndrome? An Editorial on a Novel Study," The Israel Medical Association Journal, vol. 19, Issue 2, Feb. 2017, pp. 98-99.

China National Intellectual Property Administration, Chinese Application No. 202080032535.0, "Notification of Divisional Application (including Search Report)," dated Mar. 19, 2024, 7 pages.

Cornell University, "Ex Vivo In Vitro Anti-inflammatory Effects of a Mixed CBD/CBDA Hemp Oil Formulation," Project Period Mar. 2020-Dec. 2020, retrieved from https://www.vet.cornell.edu/research/awards/202003/ex-vivo-vitro-anti-inflammatory-effects-mixed-cbdcbda-hemp-oil-formulation, retrieved Dec. 5, 2022.

E.M. Rock, et al., "The Role of 5-HT1A Receptor, and Nausea and Vomiting Relief by Cannabidiol (CBD), Cannabidiolic Acid (CBDA), and Cannabigerol (CBG)," Handbook of Cannabis and Related Pathologies, p. 703-712, 2017.

Ellevet Sciences, "CBD + CBDA Studies Conducted by ElleVet Sciences," retrieved from https://www.ellevetsciences.com/cbd-science/, retrieved Dec. 5, 2022.

International Preliminary Report of Patentability for PCT Application No. PCT/US2020/030777 issued Nov. 2, 2021.

International Search Report and Written Opinion for PCT Application No. PCT/US2020/030777 mailed Jul. 22, 2020.

U.K. Intellectual Property Office, GB Patent Application No. GB2115666.6, Examination Report under Section 18(3), Aug. 2, 2022.

Burstein, Summer, "Cannabidiol (CBD) and its analogs: a review of their effects on inflammation," Bioorganic & Medicinal Chemistry 23 (2015), pp. 1377-1385, Feb. 7, 2015.

Costa, Lia et al., "Cannabinoid-induced autophagy: Protective or death role?" Prostaglandins and Other Lipid Mediators 122 (2016), pp. 54-63, Dec. 28, 2015.

EP App. No. 20798958.3 European Search Report dated Jan. 9, 2023 (10 pages).

Pellati, Federica et al., "Cannabis sativa L. and Nonpsychoactive Cannabinoids: Their Chemistry and Role against Oxidative Stress, Inflammation, and Cancer," BioMed Research International, vol. 2018, article ID 1691428, Hindawi, Dec. 4, 2018.

International Patent Application No. PCT/US2022/076278 International Search Report and Written Opinion dated Dec. 27, 2022.

Burstein, Summer, "Cannabidiol (CBD) and its analogs: a review of their effects on inflammation," Bioorganic & Medicinal Chemistry 23 (2015), pp. 1377-1385, Feb. 7, 2015.

Ellevet Sciences, "CBD + CBDA Studies Conducted by ElleVet Sciences," retrieved from , retrieved Dec. 5, 2022.

European Patent Office, European Patent Application No. 25219044.2, "Extended European Search Report" dated Mar. 13, 2026, 14 pages.

Komarnytsky, Slavko, "Endocannabinoid System and Its Regulation by Polyunsaturated Fatty Acids and Full Spectrum Hemp Oils," International Journal of Molecular Sciences, May 22, 2021, 16 pages.

European Patent Office, European Patent Application No. 23866300.9, "Supplementary European Search Report" dated Sep. 29, 2025, 10 pages.

Charles River, "MSU-001—Part B: Investigating the Synergistic Immunosuppressive Effects of CBD and CBDA Cannabirioids in a LPS Stimulated Human THP-1 Macrophage Assay".

Ying,. Kong, "THP-1 cellular essay to determine the poteritial synergistic effect of an equimolar 1:1 CBD:CBDA mixture as an anti-inflammatory agent," The University of Tennessee Health Science Center College of Medicine, Nov. 17, 2020.

Pascoe, Anna, "MSU-001—Part. B: Investigating the Synergistic Immunosuppressive Effects of OBD and CBDA Cannabinoids in a LPS Stimulated Human THP-1 Macrophage Assay," Charles River Laboratories, Jul. 8. 2020.

Ying, Kong, "THP-1 cellular assay to determine the potential synergistic effect of an equimolar 1:1 CBD:CBDA mixture as an anti-inflammatory agent," The University of Tennessee Health Science Center College of Medicine, Nov. 17, 2020.

* cited by examiner dimethyl allyl pyrophosphate (DMAPP)

Figure 1A:
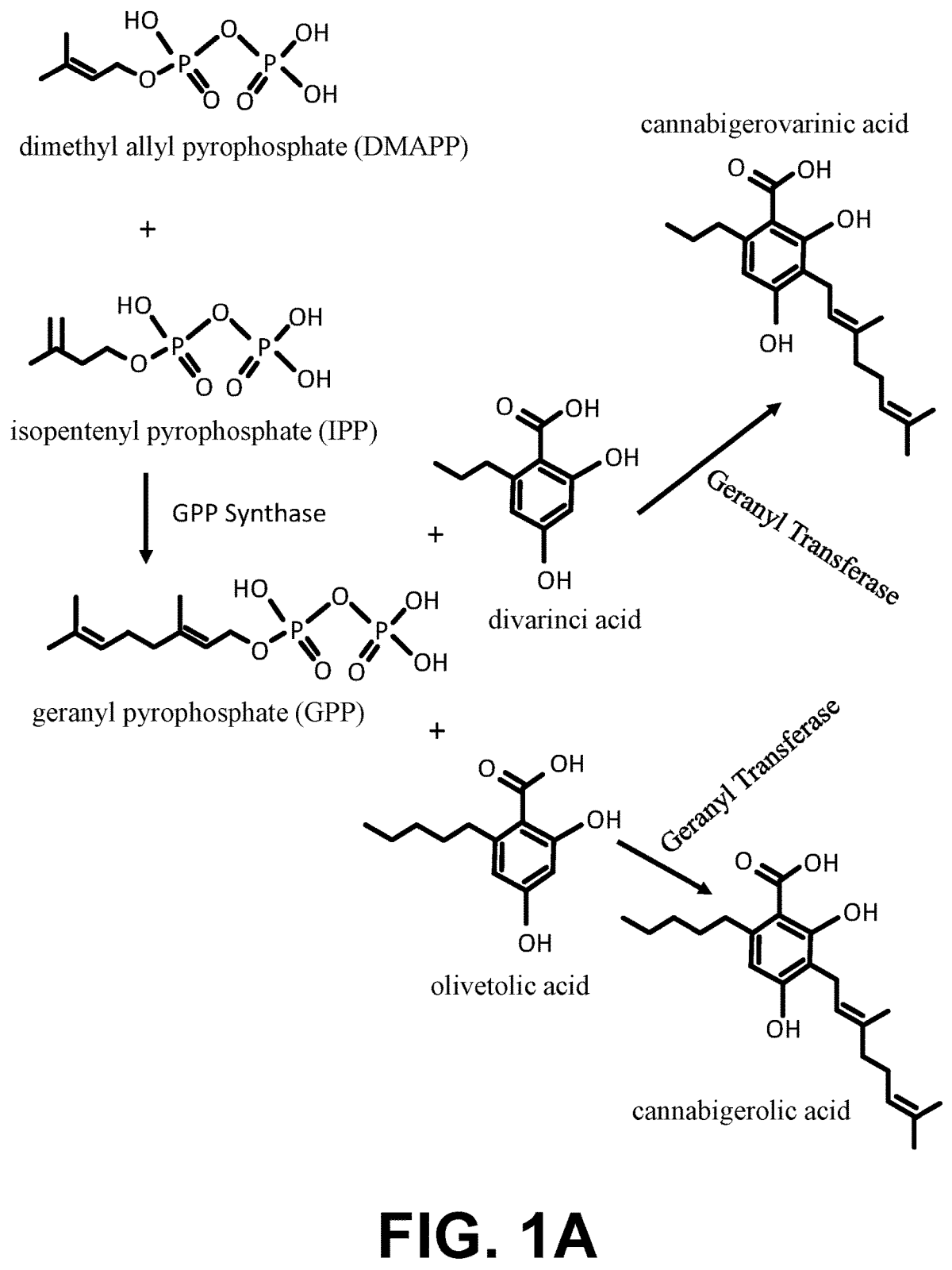

+ isopentenyl pyrophosphate (IPP)

GPP Synthase geranyl pyrophosphate (GPP)

+ divarinci acid

Geranyl Transferase cannabigerovarinic acid

+ olivetolic acid

Geranyl Transferase cannabigerolic acid

FIG. 1A cannabichromevarinic acid (CBCVA)

tetrahydrocannabivarinic acid (Δ-9 THCVA)

cannabidivarinic acid (CBDVA)

cannabidiolic acid (CBDA)

tetrahydrocannabinolic acid (Δ-9 THCVA)

cannabichromenic acid (CBCA)

cannabigerovarinic acid cannabigerolic acid

CBC

CBCA

CBD

CBDA

CBDV

CBDVA

CBG

CBGA

FIG. 2D

CBL

CBLA

CBN

CBNA

FIG. 2F

THCV

THCVA

FIG. 2G

Omega-3 α-linolenic acid (ALA), $C_{18}H_{30}O_2$

FIG. 3A

Omega-3 docosahexaenoic acid (DHA) , $C_{22}H_{32}O_2$

FIG. 3B

Omega-3 eicosapentaenoic acid (EPA) , $C_{20}H_{30}O_2$

FIG. 3C

Omega-3 octadecatetraenoic acid , $C_{18}H_{28}O_2$

Omega-7 palmitoleic acid, $C_{16}H_{30}O_2$

Omega-7 vaccenic acid , $C_{18}H_{34}O_2$

Omega-9 gondoic acid, $C_{20}H_{38}O_2$

Omega-9 oleic acid, $C_{18}H_{34}O_2$

CANNABINOID AND OMEGA FATTY ACID COMPOSITIONS AND METHODS OF USING

CROSS-REFERENCES TO RELATED APPLICATIONS

This application is a continuation-in-part of U.S. patent application Ser. No. 17/931,249, entitled "Cannabinoid and Omega Fatty Acid Compositions and Methods of Use," filed on Sep. 12, 2022, which is pending; which is a continuation-in-part of U.S. patent application Ser. No. 17/594,830, entitled "Cannabinoid Compositions and Methods of Using," filed on Oct. 29, 2021, which is pending; which is the § 371 U.S. national stage entry of International Application No. PCT/US2020/030777, entitled "Cannabinoid Compositions and Methods of Using," filed on Apr. 30, 2020, which is expired; which claims priority to U.S. Provisional Application No. 62/840,972, entitled "Cannabinoid Compositions and Methods of Using," filed on Apr. 30, 2019. The contents of these applications are hereby incorporated by reference in their entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The immune system is a complex network of cells, effector proteins, and compounds that defends the body against invading agents. Usually the immune system responds to foreign antigens, such as bacteria, fungi, and viruses, or to tissue damage caused by contusions or abrasions. These responses are typically referred to as inflammatory since they induce or turn on the immune system. Unfortunately, the immune system can also respond to antigens produced by the body as well, the result of which is the development of autoimmune diseases. The prevalence of autoimmune diseases is rapidly increasing with Addison's disease, autoimmune hepatitis, Celiac disease, Crohn's disease, Grave's disease, idiopathic thrombocytopenic purpura, multiple sclerosis, primary biliary cirrhosis, psoriatic disease, rheumatoid arthritis, scleroderma, Sjogren's syndrome, systemic lupus erythematosus, type I diabetes, and ulcerative colitis all being recognized as autoimmune diseases.

Therapeutics used to treat inflammatory conditions or autoimmune diseases include nonsteroidal anti-inflammatory drugs (NSAIDs), such as acetylsalicylic acid, ibuprofen, naproxen, and celecoxib; conventional synthetic disease-modifying antirheumatic drugs (DMARDs), such as methotrexate, hydroxychloroquine, sulfasalazine, leflunomide, and gold salts; corticosteroids, such as cortisone, dexamethasone, hydrocortisone, and prednisone; non-antibody tumor necrosis factor alpha (TNFα or TNF) inhibitors such as the xanthine derivatives pentoxifylline and bupropion; and monoclonal antibody TNF inhibitors, such as adalimumab, etanercept, and infliximab.

Typically, NSAIDs are tried first to alleviate inflammatory conditions or symptoms of autoimmune diseases before progressing to conventional synthetic DMARDs, then corticosteroids, and ultimately TNF inhibitors.

Unfortunately for people with aggravated inflammatory conditions or advanced autoimmune diseases, the TNF inhibitors, the most potent therapeutics, often do not work and can cause life threatening responses that require discontinuation of use (Jain and Singh, 2013; Hadam et al., 2014). Accordingly, there is a need for additional therapeutics to alleviate inflammatory conditions or symptoms of autoimmune diseases.

The endocannabinoid system, which functions due to the interaction of endocannabinoid compounds with G protein-coupled endocannabinoid receptors and is a key regulator of the brain and central nervous system, is also involved in the regulation of the immune system (Pandey et al., 2009; Barrie and Manolios, 2017). The $\Delta^9$-tetrahydrocannibinol ($\Delta^9$-THC or THC) is a cannabinoid that can be derived by the decarboxylation of the natural plant phytocannabinoid THCA produced by *Cannabis* varieties. It mimics the endocannabinoid anandamide and interacts with the CB1 and CB2 endocannabinoid receptors and is well documented for its use as a psychotropic agent in relieving pain and anxiety (Fine and Rosenfeld, 2013). The non-psychotropic cannabidiol (CBD) is a cannabinoid that can be derived by the decarboxylation of the natural plant phytocannabinoid cannabidiolic acid (CBDA). It is produced by *Cannabis* varieties, and has gained attention as a potential anti-inflammatory or immunosuppressant therapeutic (Nagarkatti et al., 2009; Lodzki et al., 2003; Costa et al., 2004; Raj an et al., 2016; Petrosino et al., 2018). While it is unclear how CBD affects the endocannabinoid system, a number of studies have postulated potential mechanisms by which this might occur (Di Marzo and Piscitelli, 2015; McPartland et al., 2015).

*Cannabis* varieties produce eight major cannabinoids. The metabolic pathway by which these cannabinoids are synthesized is shown in FIG. 1. Cannabigerovarinic acid (CBGVA) is produced from geranyl pyrophosphate by geranyl transferase with the addition of divarinic acid, while cannabigerolic acid (CBGA) is produced from geranyl pyrophosphate by geranyl transferase with the addition of olivetolic acid. Cannabichromevarinic acid (CBCVA), $\Delta^9$-tetrahydrocannabivarinic acid ($\Delta^9$-THCVA or THCVA) and cannabidivarinic acid (CBDVA) is produced from CBGVA by cannabichromenic acid (CBCA) synthase, $\Delta^9$-tetrahydrocannabinolic acid A ($\Delta^9$-THCA or THCA) synthase and cannabidiolic acid (CBDA) synthase, respectively. CBCA, $\Delta^9$-THCA and CBDA is produced from CBGA by CBCA synthase, $\Delta^9$-THCA synthase and CBDA synthase, respectively. The natural CBGVA, CBGA, CBCVA, $\Delta^9$-THCVA, CBDVA, CBCA, $\Delta^9$-THCA and CBDA cannabinoids that are produced via the cannabinoid metabolic pathway can be decarboxylated with heat to yield cannabigerivarin (CBGV), cannabigerol (CBG), cannabichromevarin (CBCV), tetrahydrocannabivarin ($\Delta^9$-THCV or THCV), cannabidivarin (CBDV), cannabichromene (CBC), $\Delta^9$-tetrahydrocannabinol ($\Delta^9$-THC or THC) and cannabidiol (CBD), respectively. A number of the natural cannabinoids and their decarboxylated derivatives can be converted to other cannabinoids. For example, CBCA and CBC can be converted to cannabicyclolic acid (CBLA) and cannabicyclol (CBL) by UV photo-irradiation, while $\Delta^9$-THCA and $\Delta^9$-THC can be converted to cannabinolic acid (CBNA) and cannabinol (CBN) by oxidative degradation.

Currently the most abundantly available non-psychotropic cannabinoid is CBDA and numerous hemp plants have been demonstrated to produce buds that contain upwards of 25% CBDA by mass. While CBDA is more difficult to isolate than CBD because of decarboxylation that occurs during purification, a number of processes have been developed that can generate CBDA extracts that contain upwards of 80% CBDA.

While the potential of CBD to act as an anti-inflammatory or immunosuppressant has been documented, no studies have investigated the ability of its precursor, CBDA, or the other major non-psychotropic cannabinoids and their decarboxylated derivatives, to act as an anti-inflammatory or immunosuppressant agents. Accordingly, there remains a need for improved cannabinoid compositions having enhanced biologic activity, such as anti-inflammatory and/or immunosuppressant activity.

SUMMARY OF THE INVENTION

This disclosure describes compositions including a cannabinoid including, for example, a phytocannabinoid (that is, a cannabinoid derived from or produced by a plant), and methods of using those compositions. In some embodiments, the composition may be useful for treating an inflammatory condition and/or an autoimmune disease. In some embodiments, the composition may be useful as an anticancer therapeutic.

In one aspect, this disclosure describes a pharmaceutical composition comprising a cannabinoid. The cannabinoid may be chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA. Combinations thereof may include, for example, two cannabinoids, three cannabinoids, four cannabinoids, five cannabinoids, or more. Exemplary combinations include CBC and CBCA; CBG and CBGA; CBL and CBLA; CBD and CBDA; CBC and CBDV; CBG, CBGA, and CBDA; CBD, CBDV, and CBGA; etc.

In another aspect, this disclosure describes a composition comprising an approximately 1:1 equimolar mixture of CBD:CBDA. In some embodiments, the composition comprising an approximately 1:1 equimolar mixture of CBD:CBDA further comprises an additional cannabinoid comprising CBC, CBCA, CBDV, CBDVA, CBG, CBGA, CBL, CBLA, CBN, CBNA, THCV, or THCVA, or a combination thereof. In other embodiments, the composition comprising an approximately 1:1 equimolar mixture of CBD:CBDA is free of or substantially free of other cannabinoids.

In another aspect, this disclosure describes a composition comprising a cannabinoid, an approximately 1:1 equimolar mixture of CBD:CBDA, and an omega unsaturated fatty acid (referred to herein as an "omega fatty acid"). In another aspect, the disclosure describes a composition comprising an approximately 1:1 equimolar mixture of CBD:CBDA and an omega fatty acid. In other embodiments, the composition comprising an approximately 1:1 equimolar mixture of CBD:CBDA and an omega fatty acid is free of or substantially free of other cannabinoids.

In some embodiments, the pharmaceutical composition is formulated for use as an anti-inflammatory agent or an immunosuppressant.

In a further aspect, this disclosure describes a method for treating or preventing inflammation or autoimmunity in a subject. The method includes administering to the subject a composition including an effective amount of a cannabinoid. In some embodiments, the cannabinoid is chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA. In some embodiments, the cannabinoid is chosen from i) CBL, CBLA, THCVA, and any combination thereof, and ii) an approximately 1:1 equimolar mixture of CBD:CBDA.

In another further aspect, this disclosure describes a method for treating or preventing inflammation or autoimmunity in a subject. The method includes administering to the subject a composition including an effective amount of a cannabinoid. In some embodiments, the cannabinoid is chosen from: i) CBC, CBCA, CBD, CBDA, CBDV, CBDVA, CBG, CBGA, CBL, CBLA, CBN, CBNA, THCV, THCVA, and any combination thereof, ii) an approximately 1:1 equimolar mixture of CBD:CBDA, and iii) an omega fatty acid. In some embodiments, the cannabinoid is chosen from i) CBL, CBLA, THCVA, and any combination thereof, ii) an approximately 1:1 equimolar mixture of CBD:CBDA, and iii) an omega fatty acid.

As used herein, "approximately" is defined as being within 10%, preferably within 5%, more preferably within 1%, and most preferably within 0.5%.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The term "consisting essentially of" indicates that the elements listed after the phrase are included, and that other elements than those listed may be included provided that those elements do not materially affect the basic and novel characteristic(s)" of the claimed invention.

The term "free of" or "substantially free of" indicates that any elements listed after the phrase are not included or, if they are included, those elements do not substantially interfere with or contribute to the activity or action specified in the disclosure for the other elements in the composition. Those skilled in the art will readily appreciate that elements listed after the term "free of" or "substantially free of" may, in some circumstances, be present as the result of impurities from process such as extraction of cannabinoids from *Cannabis*. In some embodiments, when a composition is substantially free of other cannabinoids, the composition contains 10% or less, 5% or less, 4% or less, 3% or less, 2% or less, 1% or less, 0.5% or less, or 0.1% or less of the other cannabinoids.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE DRAWINGS

FIG. 1A-FIG. 1B show an exemplary *Cannabis* metabolic pathway for the synthesis of the major cannabinoids. The synthesis of CBCA, CBDA, CBCVA, CBDVA, CBGA, CBGVA, Δ9-THCA and Δ9-THCVA from geranyl pyrophosphate (GPP) are shown along with the key enzymes that are involved. FIG. 1A shows the synthesis of CBGA and CBGVA from GPP. FIG. 1B shows the synthesis of CBCVA, CBDVA and THCVA from CBGVA and the synthesis of CBCA, CBDA and THCA and from CBGA.

FIG. 2A-FIG. 2G show structures of the cannabinoids used in Example 1. FIG. 2A shows the structures of cannabichromene (CBC) and cannabichromenic acid (CBCA).

FIG. 2B shows the structures of cannabidiol (CBD) and cannabidiolic acid (CBDA). FIG. 2C shows the structures of cannabidivarin (CBDV) and cannabidivarinic acid (CBDVA). FIG. 2D shows the structures of cannabigerol (CBG) and cannabigerolic acid (CBGA). FIG. 2E shows the structures of cannabicyclol (CBL) and cannabicyclolic acid (CBLA). FIG. 2F shows the structures of cannabinol (CBN) and cannabinolic acid (CBNA). FIG. 2G shows the structures of tetrahydrocannabivarin (THCV) and tetrahydrocannabivarinic acid (THCVA).

FIG. 3A-FIG. 3H show structures of omega fatty acids used in the studies of Examples 6A-C. FIG. 3A shows the structures of α-linolenic acid (ALA) omega-3 fatty acid. FIG. 3B shows the structures of docosahexaenoic acid (DHA) omega-3 fatty acid. FIG. 3C shows the structures of eicosapentaenoic acid (EPA) omega-3 fatty acid. FIG. 3D shows the structures of octadecatetraenoic acid omega-3 fatty acid. FIG. 3E shows the structures of palmitoleic acid omega-7 fatty acid. FIG. 3F shows the structures of vaccenic acid omega-7 fatty acid. FIG. 3G shows the structures of gondoic acid omega-9 fatty acid. FIG. 3H shows the structures of oleic acid omega-9 fatty acid.

DETAILED DESCRIPTION OF THE INVENTION

Figure 1B:
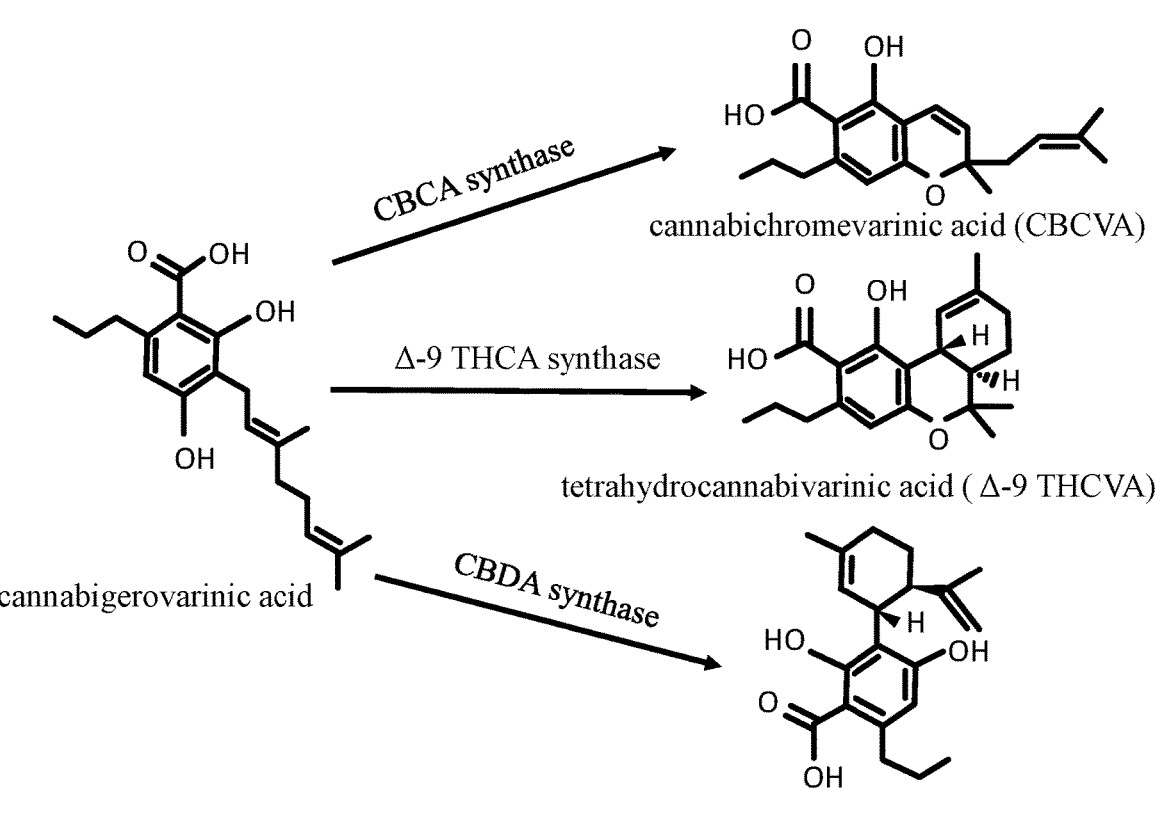
Figure 2A:
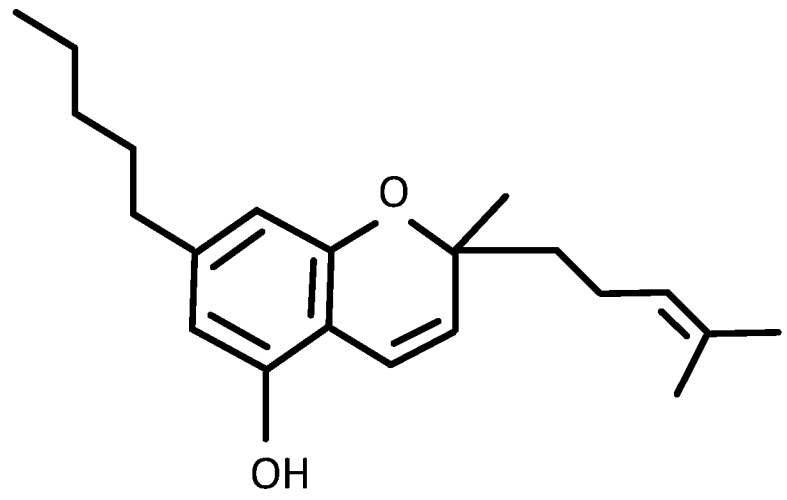
Figure 2B:
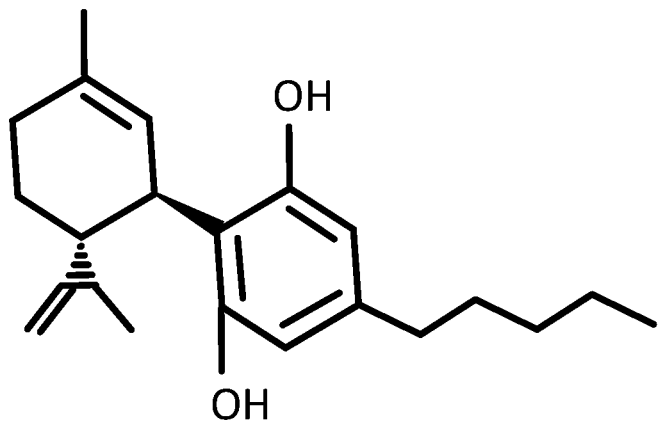
Figure 2C:
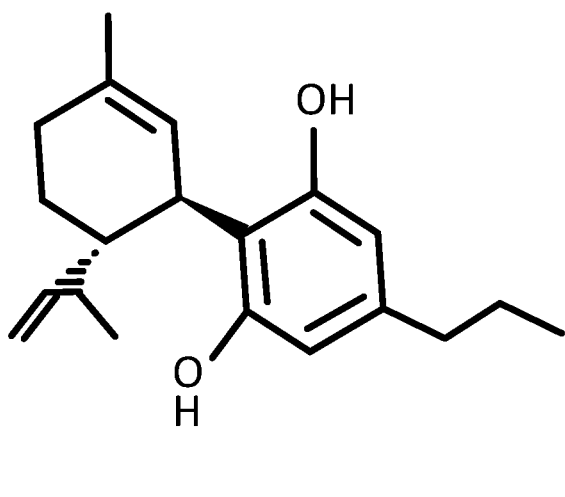
Figure 2D:
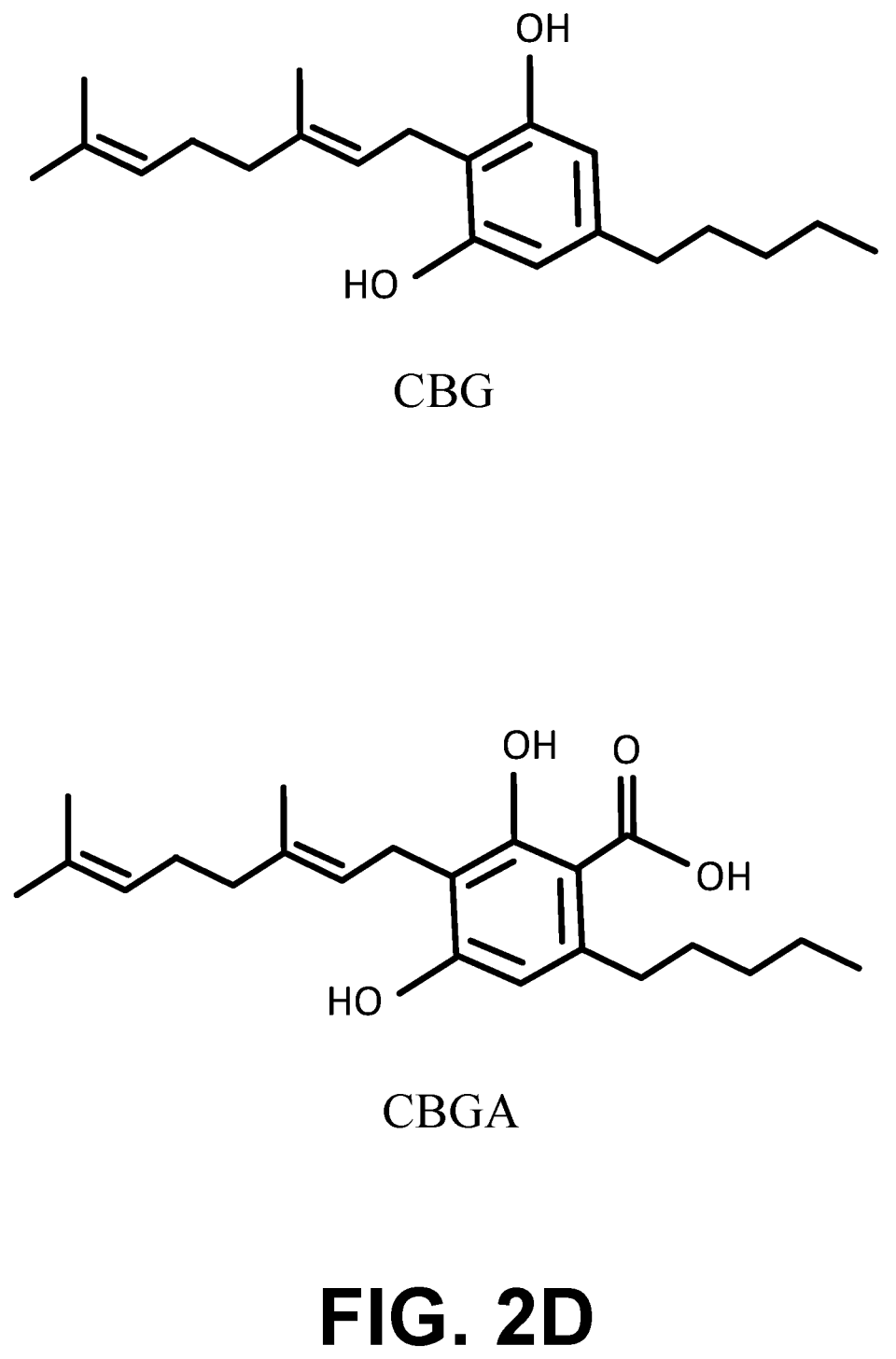
Figure 2E:
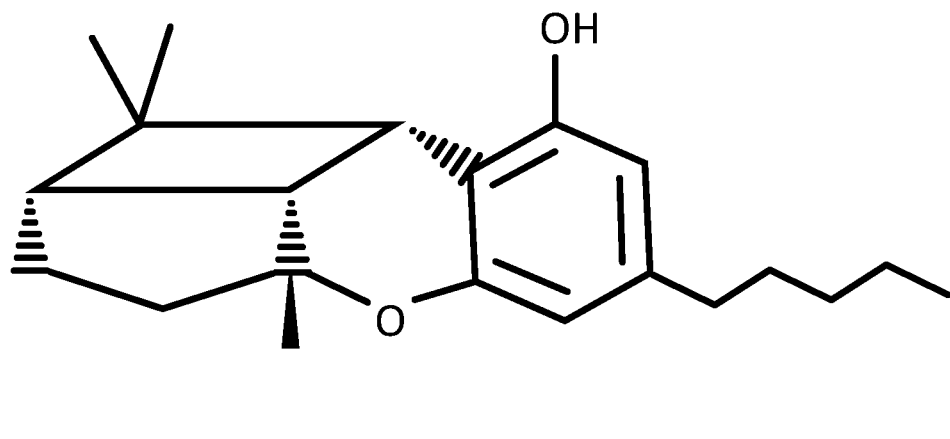
Figure 2E:
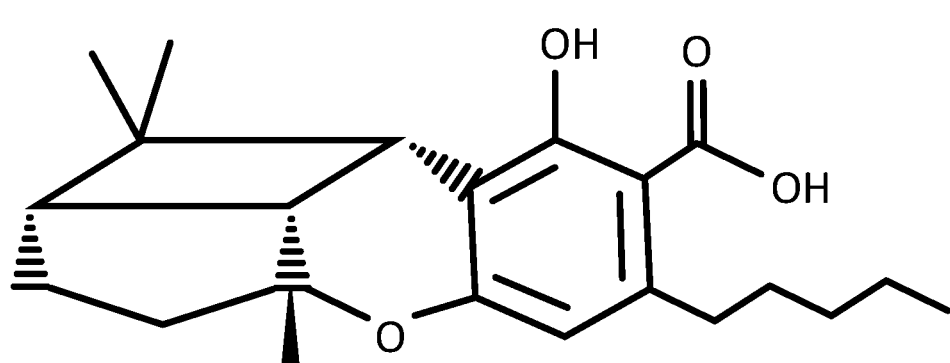
Figure 2F:
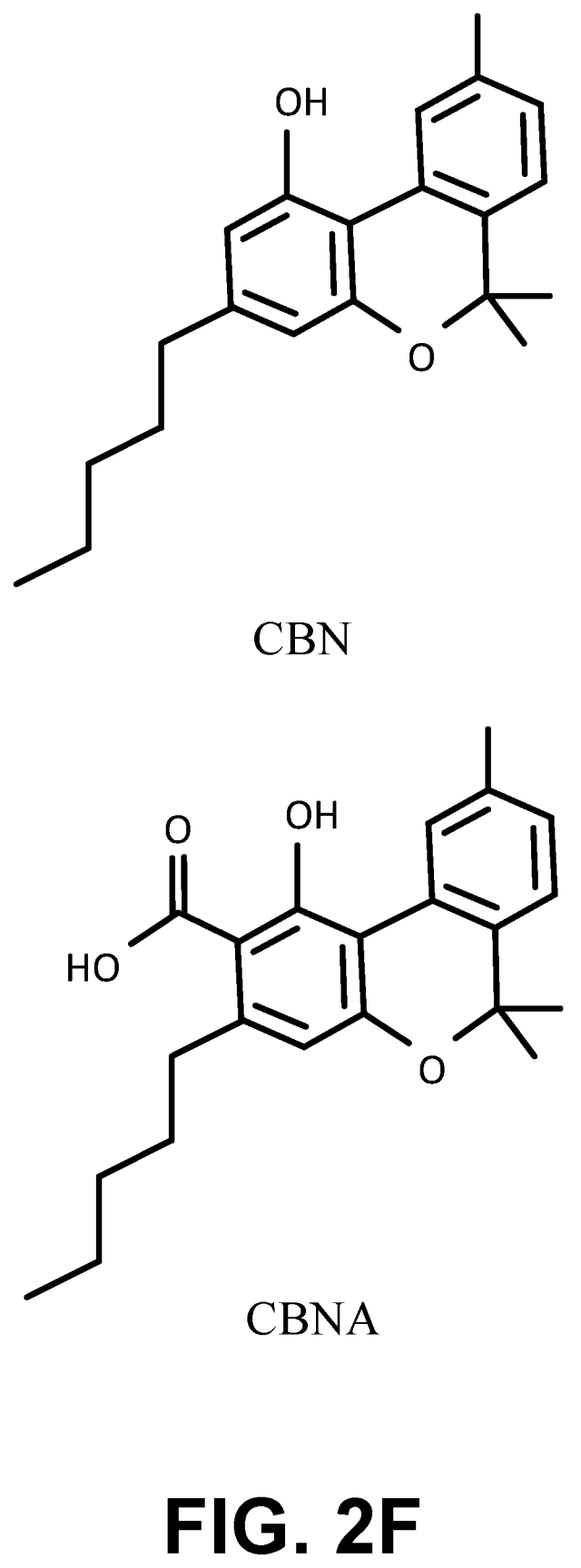
Figure 2G:
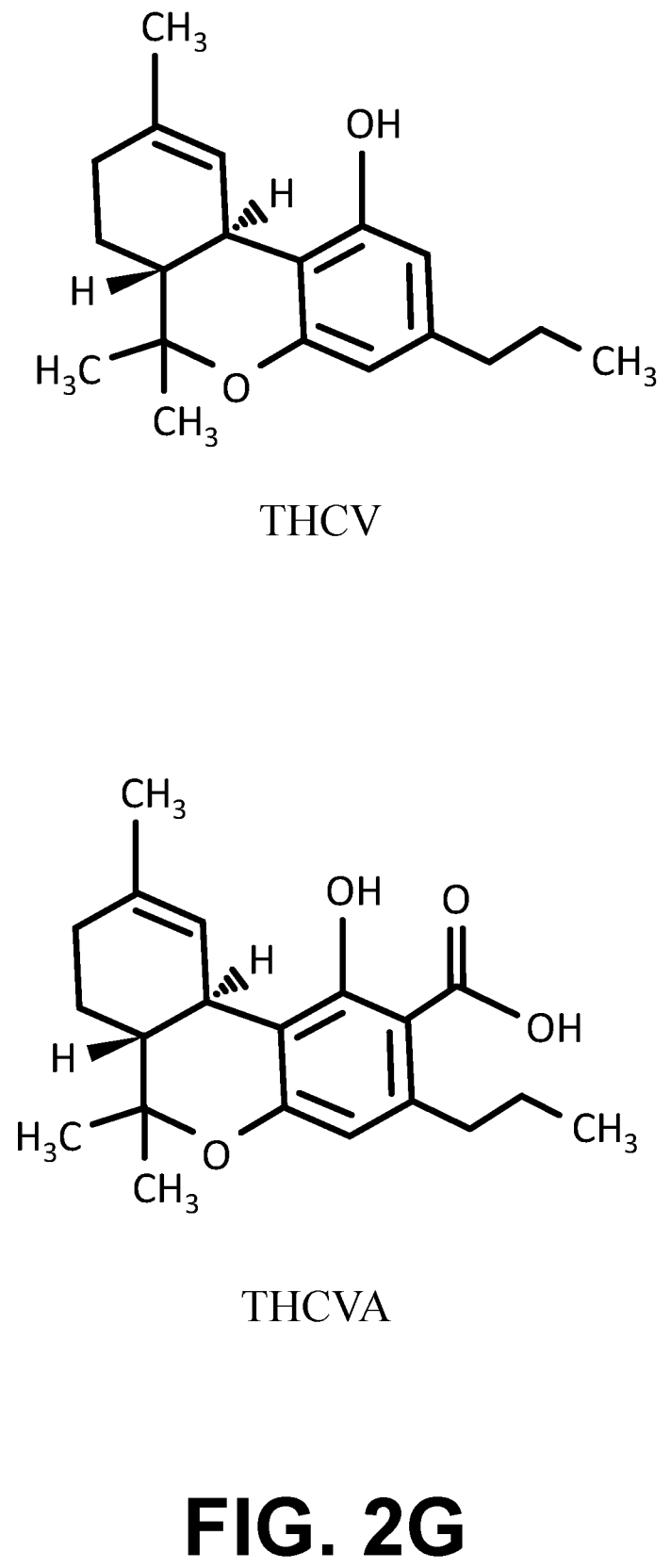

This disclosure describes compositions comprising cannabinoids and methods of using those compositions including, for example, to treat or prevent inflammation, as an immunosuppressant, and/or as an anti-cancer therapeutic.
Cannabinoid Compositions In one aspect, this disclosure describes a pharmaceutical composition including a cannabinoid. In exemplary embodiments, the cannabinoid is chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA. The IUPAC names of each of these cannabinoids are listed below in Table 1, and their structures are shown in FIG. 2.

TABLE 1

Listing of Exemplary Cannabinoids

| Cannabinoid | IUPAC Name |
|---|---|
| CBC | 2-Methyl-2-(4-methyl-3-penten-1-yl)-7-pentyl-2H-chromen-5-ol |
| CBCA | 5-Hydroxy-2-methyl-2-(4-methyl-3-penten-1-yl)-7-pentyl-2H-chromene-6-carboxylic acid |
| CBD | 2-[(1R,6R)-6-Isopropenyl-3-methyl-2-cyclohexen-1-yl]-5-pentyl-1,3-benzenediol |
| CBDA | 2,4-Dihydroxy-3-[(1R,6R)-6-isopropenyl-3-methyl-2-cyclohexen-1-yl]-6-pentylbenzoic acid |
| CBDV | 2-(6-Isopropenyl-3-methyl-2-cyclohexen-1-yl)-5-propyl-1,3-benzenediol |
| CBDVA | 2,4-Dihydroxy-3-[(1R,6R)-6-isopropenyl-3-methyl-2-cyclohexen-1-yl]-6-propylbenzoic acid |
| CBG | 2-[(2E)-3,7-Dimethyl-2,6-octadien-1-yl]-5-pentyl-1,3-benzenediol |
| CBGA | 3-[(2E)-3,7-Dimethyl-2,6-octadien-1-yl]-2,4-dihydroxy-6-pentylbenzoic acid |
| CBL | 1,1,3a-Trimethyl-6-pentyl-1a,2,3,3a,8b,8c-hexahydro-1H-4-oxabenzo[f]cyclobuta[cd]inden-8-ol |
| CBLA | (1aS,3aR,8bR,8cR)-8-Hydroxy-1,1,3a-trimethyl-6-pentyl-1a,2,3,3a,8b,8c-hexahydro-1H-4-oxabenzo[f]cyclobuta[cd]indene-7-carboxylic acid |
| CBN | 6,6,9-Trimethyl-3-pentyl-6H-benzo[c]chromen-1-ol |
| CBNA | 1-Hydroxy-6,6,9-trimethyl-3-pentyl-6H-benzo[c]chromene-2-carboxylic acid |

TABLE 1-continued

Listing of Exemplary Cannabinoids

| Cannabinoid | IUPAC Name |
|---|---|
| THCV | (6aR,10aR)-6,6,9-trimethyl-3-propyl-6H,6aH,7H,8H,10aH-benzo[c]isochromen-1-ol |
| THCVA | (6aR,10aR)-6a,7,8,10a-tetrahydro-1-hydroxy-6,6,9-trimethyl-3-propyl-6H-Dibenzo[b,d] pyran-2-carboxylic acid |

In some embodiments, the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA. In other embodiments, the cannabinoid is chosen from cannabinoid is chosen from the CBC, CBCA, CBD, CBDA, CBDV, CBDVA, CBG, CBGA, CBL, CBLA, CBN, CBNA, THCV, THCVA, and any combination thereof. In further embodiments, the cannabinoid is chosen from is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA. In still other embodiments, the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA. In other embodiments, the cannabinoid is chosen from the CBCA, CBDA, CBDV, CBDVA, CBGA, CBL, CBLA, CBN, CBNA, and any combination thereof. In other embodiments, the cannabinoid is chosen from the CBDV, CBL, CBLA, CBN, CBNA and any combination thereof.

In other embodiments, the cannabinoid is chosen from the cannabinoid is chosen from i) the CBCA, CBD, CBDA, CBDV, CBDVA, CBG, CBL, CBLA, CBN, CBNA, THCV, and THCVA, and ii) the approximately 1:1 equimolar mixture of CBD:CBDA. In other embodiments, the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

In some embodiments, a composition includes the approximately 1:1 equimolar mixture of CBD:CBDA. When the composition includes the approximately 1:1 equimolar mixture of CBD:CBDA, the composition may be substantially free of other cannabinoids. In some embodiments, the cannabinoid consists essentially of the approximately 1:1 equimolar mixture of CBD:CBDA. In other embodiments, the cannabinoid consists essentially of a 1:1 equimolar mixture of CBD:CBDA. In other embodiments when the cannabinoid includes the approximately 1:1 equimolar mixture of CBD:CBDA, the composition may further include an additional cannabinoid chosen from CBC, CBCA, CBDV, CBDVA, CBG, CBGA, CBL, CBLA, CBN, CBNA, THCV, THCVA, and any combination thereof.

In some embodiments, the cannabinoid is chosen from i) the CBD, CBDA, CBDV, CBDVA, CBG, and THCV and ii) the approximately 1:1 equimolar mixture of CBD:CBDA.

In other embodiments, the cannabinoid is chosen from chosen from: i) CBL, CBLA, and THCVA, and any mixture thereof; and ii) an approximately 1:1 equimolar mixture of CBD:CBDA.

In some embodiments, the composition may include a cannabinoid extract including, for example, from hemp flowers or buds. Extracts from hemp flowers or buds that contain high concentrations of a cannabinoid can be easily prepared by a variety of methods, which include but are not limited to supercritical fluid extraction using carbon dioxide, butane or water, or ethanol solvent extraction.

As further described in the Examples, the individual cannabinoids CBC, CBCA, CBD, CBDA, CBDV, CBDVA, CBG, CBGA, CBL, CBLA, CBN, CBNA, THCV, and THCVA, and a 1:1 equimolar mixture of CBD:CBDA each showed potential as antioxidant, anti-inflammatory agents and/or immunosuppressants. In some embodiments, the cannabinoid may be at least half as effective as dexamethasone at reducing elevated cytokine levels in differentiated THP-1 cells that had been treated with LPS, indicating anti-inflammatory and/or immunosuppressant activity. For example, the individual cannabinoids CBCA, CBD, CBDA, CBDVA, CBDV, CBG, CBGA, CBLA, CBL, CBNA, CBN, THCVA, THCV, and a 1:1 equimolar mixture of CBD:CBDA were very effective at reducing elevated cytokine levels in differentiated THP-1 cells that had been treated with LPS.

In some embodiments, the cannabinoid induces radical scavenging activity by at least two-fold compared to an untreated control. For example, the individual cannabinoids CBD, CBDA, CBDV, CBDVA, CBG, THCV and a 1:1 equimolar mixture of CBD:CBDA had significant antioxidant activity in a DPPH assay.

The individual cannabinoids CBL, CBLA, THCVA, and a 1:1 equimolar mixture of CBD:CBDA proved to be particularly effective at inducing autophagy in differentiated U937 cells.

The immune system is stringently regulated via a counterbalance between inflammatory (proinflammatory) and anti-inflammatory cytokines. Inflammatory cytokines induce the immune system while anti-inflammatory cytokines repress the immune system. Normally this counterbalance keeps the immune system in check and ready to act when necessary. When an inflammatory response occurs due to inflammation or autoimmune diseases, the levels of inflammatory cytokines drastically increase. There are a number of extensive reviews that describe the regulation of the immune system by inflammatory and anti-inflammatory cytokines (Pripp and Stanišić M, 2014; Wang et al., 2015; Musolino et al., 2017; Nalbant and Birlik, 2017). The term "cytokine storm" is generally used to describe the increase in inflammatory cytokine levels that occur in people suffering from inflammatory conditions or autoimmune diseases. The inflammatory cytokines that are involved in cytokine storms and how their repression by pharmaceutical agents as treatment regimens has been extensively reviewed (Tisoncik et al. 2012; Gerlach, 2016; Behrens and Koretzky, 2017).

There is not universal agreement as to which cytokines are inflammatory or anti-inflammatory, however, IFNγ, IL-1β, IL-2, IL-6, IL-12, IL-15, IL-16, IL-17, IL-18, IL-23 and TNFα are widely recognized as being inflammatory cytokines while IL-1RA, IL-4, IL-10, IL-11, IL-13 and TGFβ are widely recognized as being anti-inflammatory cytokines (Pripp and Stanišić M, 2014; Wang et al., 2015; Musolino et al., 2017; Nalbant and Birlik, 2017). Over 100 cytokines have been identified to date and many have not yet been thoroughly characterized.

While not being bound by theory, it is believed that present compositions, in some embodiments, are capable of suppressing or preventing the release of proinflammatory cytokines in the course of an inflammatory or autoimmune event, thereby reducing or preventing the cytokine storm.

In some embodiments, a composition including a particular cannabinoid may consist essentially of that cannabinoid. For example, in an exemplary embodiment, a composition including CBC may consist essentially of CBC. In another exemplary embodiments, a composition including a 1:1 equimolar mixture of CBD:CBDA may consist essentially of CBD and CBDA. A person having skill in the art will recognize, however, that a composition comprising a cannabinoid (including, for example, a cannabinoid extract) may also likely contain other cannabinoids in lesser amounts. (See Example 2.) While not being bound by theory, the present examples demonstrate surprising synergistic activity of a 1:1 equimolar mixture of CBD:CBDA. In some embodiments, when one or more additional cannabinoids is present in a composition having a 1:1 equimolar mixture of CBD:CBDA, this synergistic activity is still present.

In some embodiments, a composition including a particular cannabinoid may preferably be free of other cannabinoids. For example, in an exemplary embodiment, a composition including CBC may be free of CBCA, CBD, CBDA, CBDV, CBDVA, CBG, CBGA, CBL, CBLA, CBN, CBNA, THCV, and THCVA. In another exemplary embodiment, a composition comprising CBL, CBLA, CBD, and CBDA may be free of other cannabinoids. In a further exemplary embodiment, a composition comprising a 1:1 equimolar mixture of CBD:CBDA may be free of CBC, CBCA, CBDV, CBDVA, CBG, CBGA, CBL, CBLA, CBN, CBNA, THCV, and THCVA.

In some embodiments, including, for example, when the composition is formulated for use as an anti-inflammatory agent or an immunosuppressant the cannabinoid comprises i) CBC, CBCA, CBD, CBDA, CBDV, CBDVA, CBG, CBGA, CBL, CBLA, CBN, CBNA, THCV, or THCVA, or a combination thereof, or ii) an approximately 1:1 equimolar mixture of CBD:CBDA.

In some embodiments, including, for example, when the composition is formulated to reduce elevated cytokine levels, the cannabinoid comprises the CBC, CBCA, CBD, CBDA, CBDV, CBDVA, CBG, CBGA, CBL, CBLA, CBN, CBNA, THCV, or THCVA, or a combination thereof. In some embodiments, including, for example, when the composition is formulated to reduce elevated cytokine levels, the cannabinoid comprises the CBD, CBDA, CBDV, CBDVA, CBG, and THCV, or any combination thereof. In some embodiments, when the cannabinoid comprises the CBD, and CBDA, the composition comprises an approximately 1:1 equimolar mixture of CBD:CBDA.

In some embodiments, including, for example, when the composition is formulated to have antioxidant activity, the cannabinoid comprises the CBD, CBDA, CBDV, CBDVA, CBG, or THCV, or any combination thereof. In some embodiments, when the cannabinoid comprises the CBD, and CBDA, the composition includes an approximately 1:1 equimolar mixture of CBD:CBDA.

In some embodiments, including, for example, when the composition is formulated to induce autophagy, the cannabinoid comprises CBL, CBLA, THCVA, or any combination thereof, comprises the approximately 1:1 equimolar mixture of CBD:CBDA.

In some embodiments, a cannabinoid composition comprises an approximately 1:1 equimolar mixture of CBD:CBDA. In some embodiments, a cannabinoid composition comprises a 1:1 equimolar mixture of CBD:CBDA. As further described in Example 1, a 1:1 equimolar mixture of CBD:CBDA was surprisingly found to be more effective at reducing elevated cytokine levels in THP-1 cells treated with LPS than CBD or CBDA alone, to demonstrate a significant antioxidant activity in a DPPH assay, and to induce autophagy in differentiated U937 cells—each indicating its potential as an anti-inflammatory agent or an immunosuppressant. The 1:1 equimolar mixture of CBD:CBDA demonstrated a significant effect of all three of these activities in the present Examples.

Moreover, that both CBD and CBDA act as potent anti-inflammatory agents was also surprising and somewhat counterintuitive. Numerous studies on THCA and its decarboxylated derivative, THC, have made it abundantly clear that while THC is a potent psychoactive compound, THCA is not. Based on this fact, most studies on other phytocannabinoids have presumed that the decarboxylated derivative and not the precursor is biologically active. Thus, it was surprising to find that the precursor CBDA is actually more potent than CBD as an anti-inflammatory agent.

In one embodiment, this disclosure describes a pharmaceutical composition including a cannabinoid and an omega fatty acid. In exemplary embodiments, the cannabinoid is chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA. The IUPAC names of each of these cannabinoids are listed above in Table 1, and their structures are shown in FIG. 2. In some embodiments, the pharmaceutical composition may include i) an approximately 1:1 equimolar mixture of CBD:CBDA, and ii) an omega fatty acid. The IUPAC names of possible omega fatty acids are listed below in Table 2, and their structures are shown in FIGS. 3A-3H.

TABLE 2

| Listing of Exemplary Omega Fatty Acids | |
| --- | --- |
| Omega Fatty Acid | IUPAC Name |
| Omega-3 alpha-linolenic acid | (9Z,12Z,15Z)-octadeca-9,12,15-trienoic acid |
| Omega-3 docosahexaenoic acid | (4Z,7Z,10Z,13Z,16Z,19Z)-docosa-4,7,10,13,16,19-hexaenoic acid |
| Omega-3 eicosapentaenoic acid | (5Z,8Z,11Z,14Z,17Z)-eicosa-5,8,11,14,17-pentenoic acid |
| Omega-3 octadecatetraenoic acid | (2E,4E,6E,8E)-octadeca-2,4,6,8-tetraenoic acid |
| Omega-7 palmitoleic acid | (9Z)-hexadec-9-enoic acid |
| Omega-7 vaccenic acid | (11E)-11-octadecenoic acid |

TABLE 2-continued

| Listing of Exemplary Omega Fatty Acids | |
|---|---|
| Omega Fatty Acid | IUPAC Name |
| Omega-9 gondoic acid | 11Z)-icos-11-enoic acid |
| Omega-9 oleic acid | (9Z)-octadec-9-enoic acid |

Figure 3A:
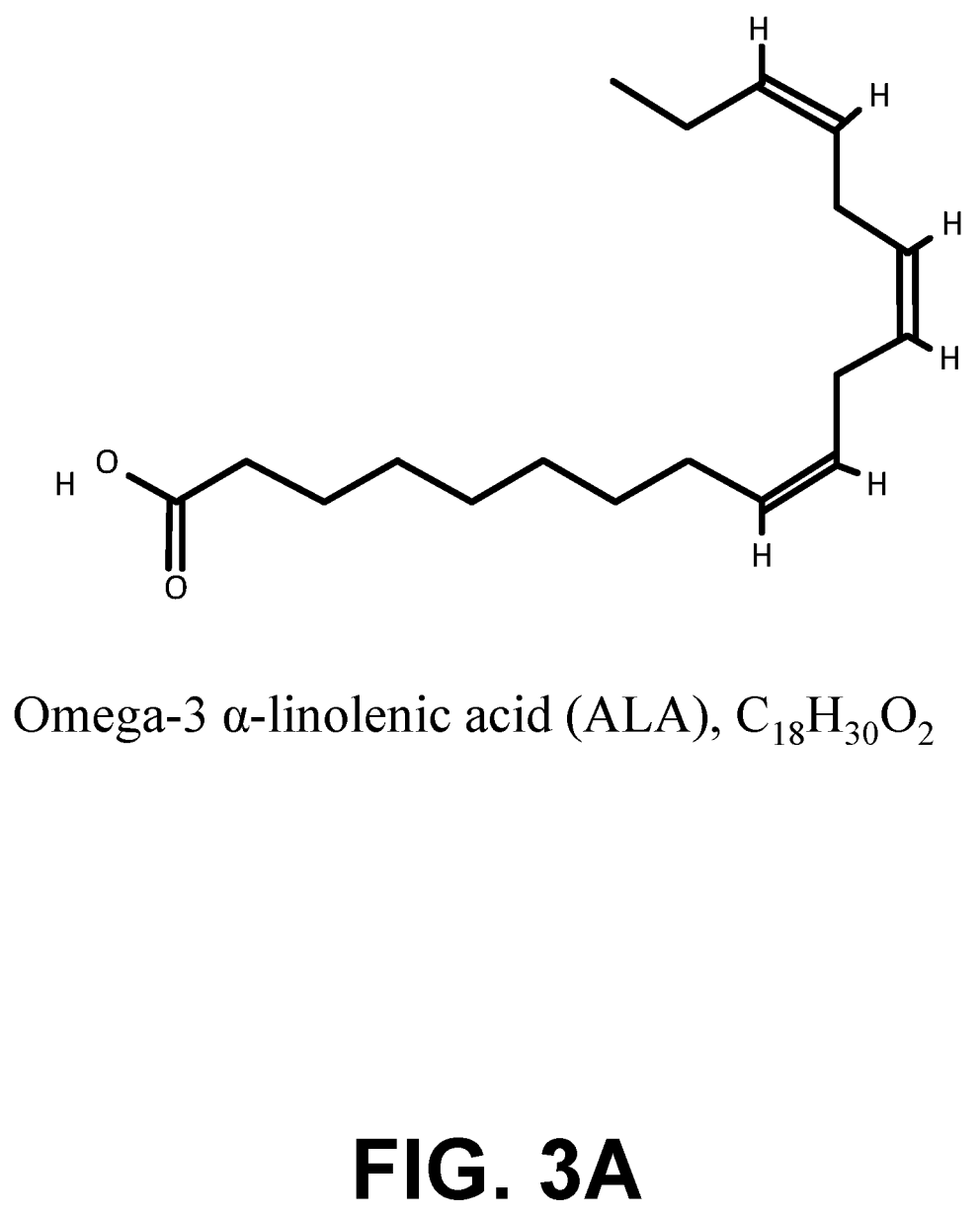
Figure 3B:
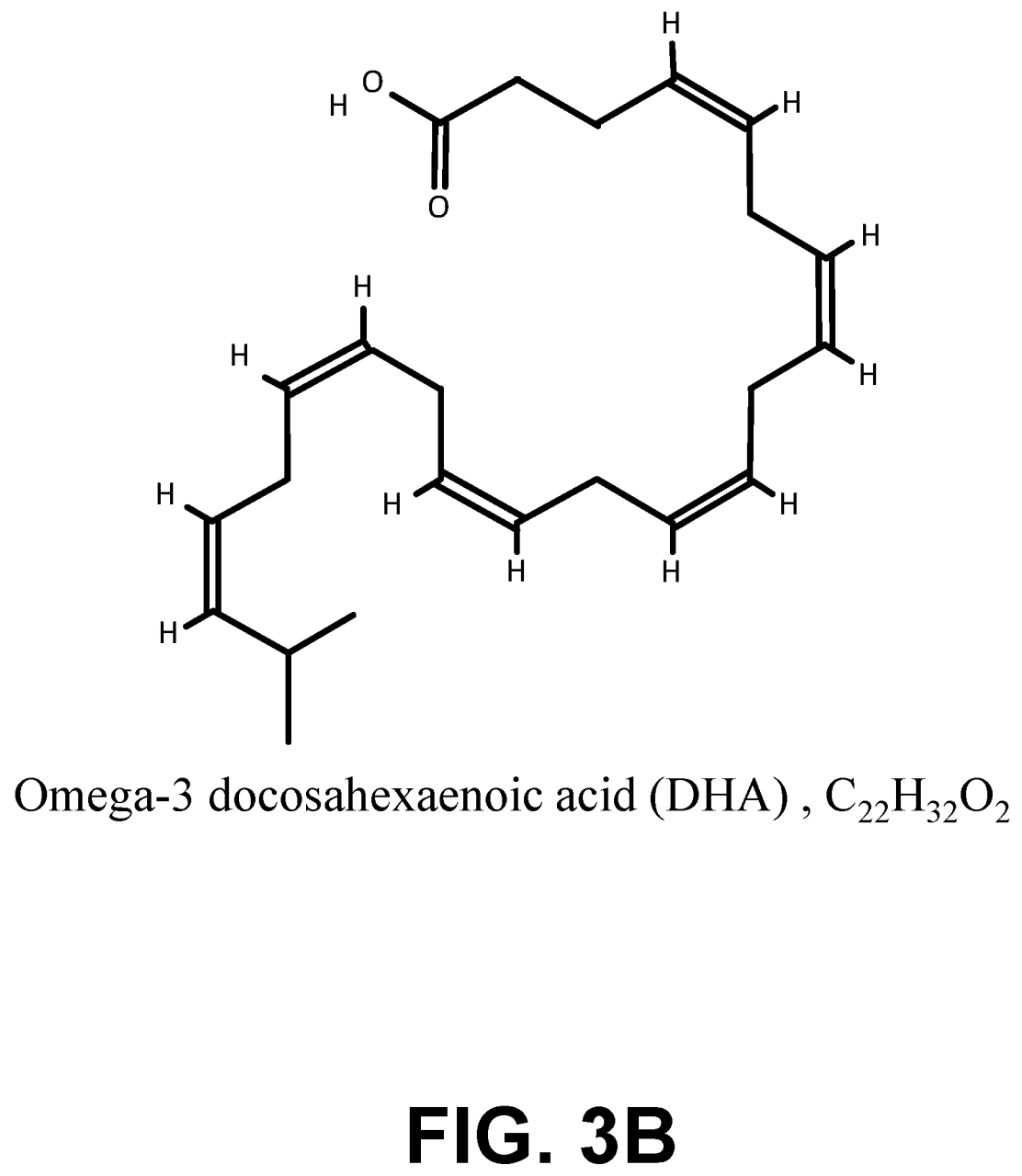
Figure 3C:
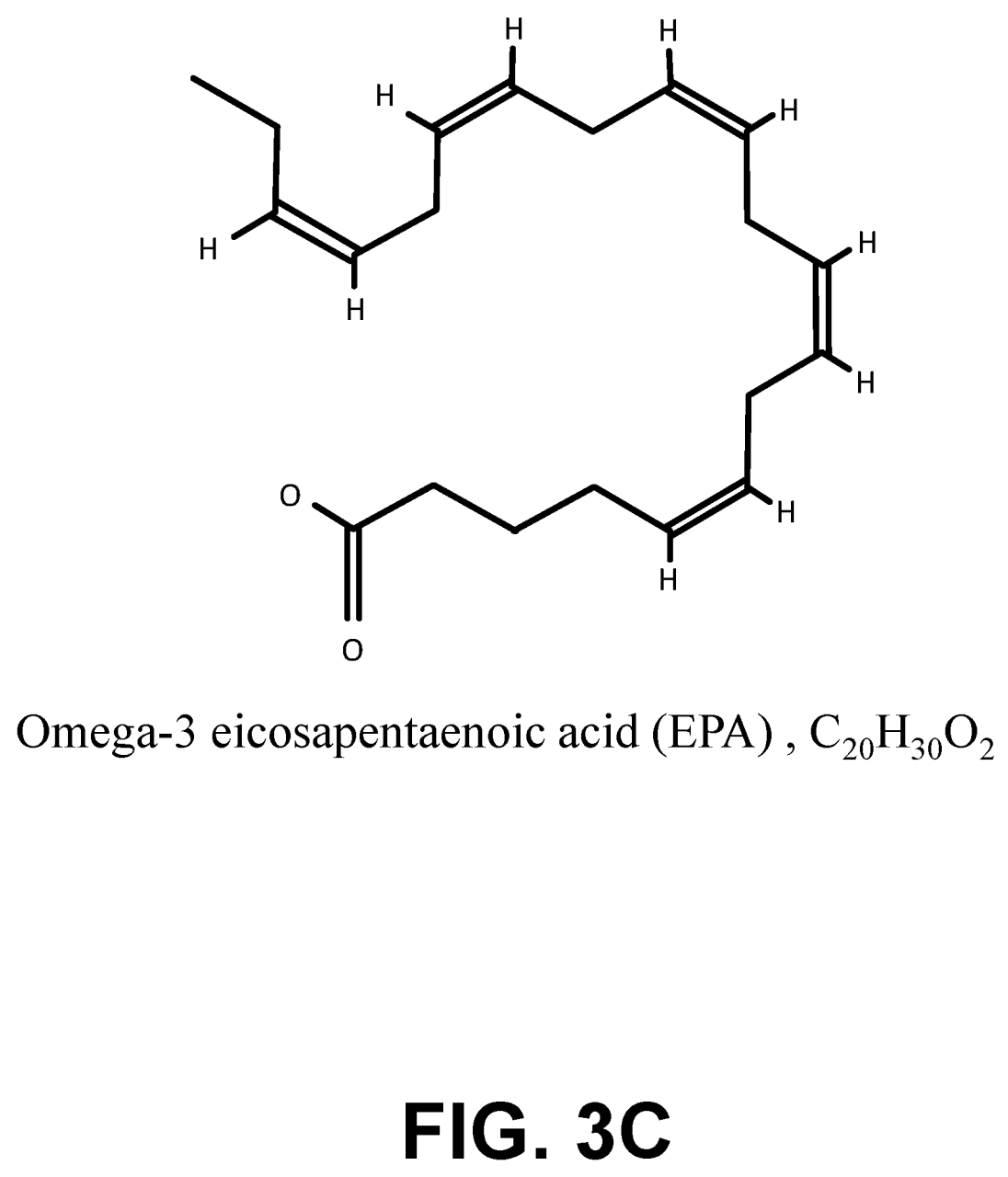
Figure 3D:
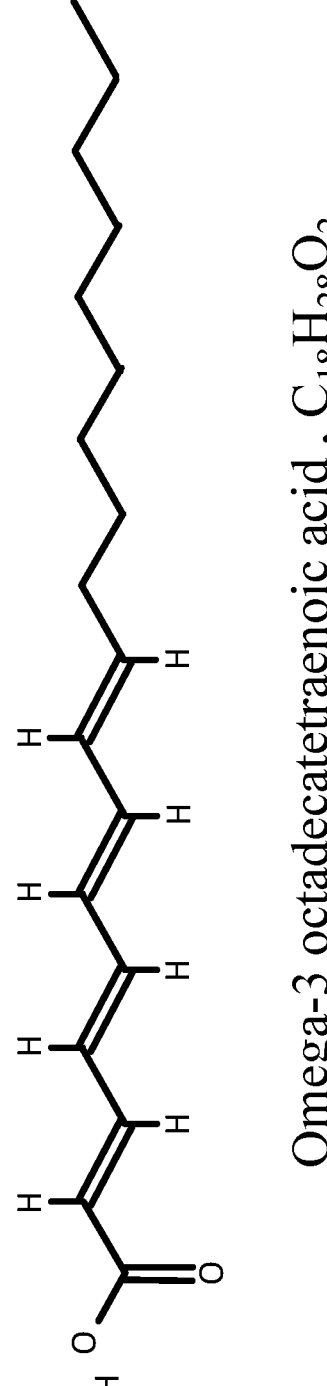
Figure 3E:
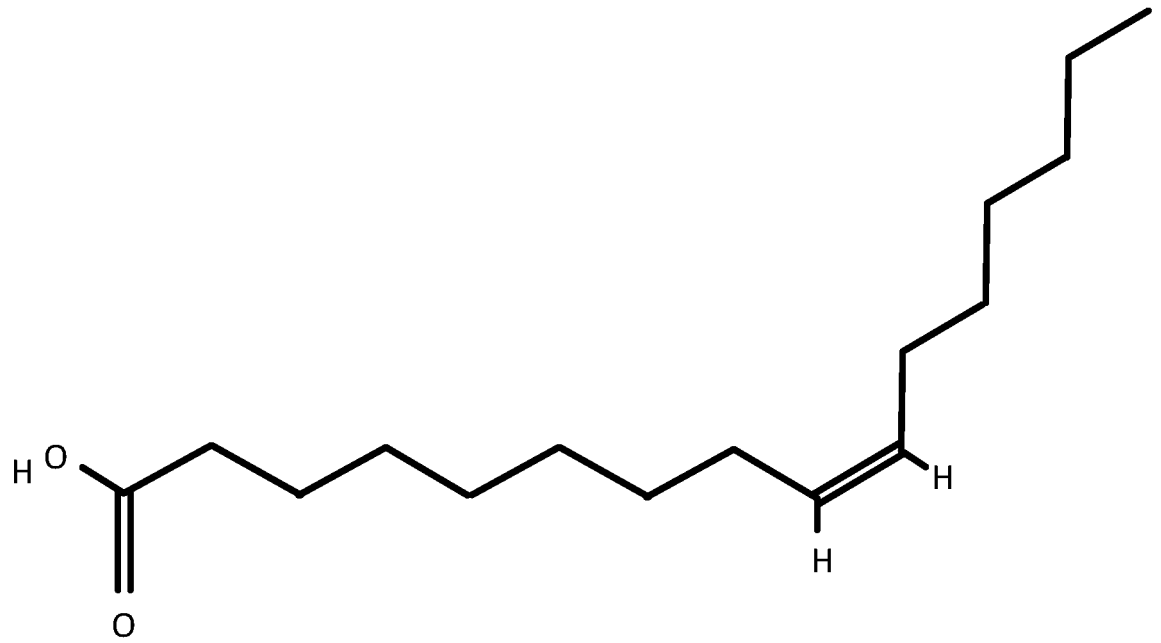
Figure 3F:
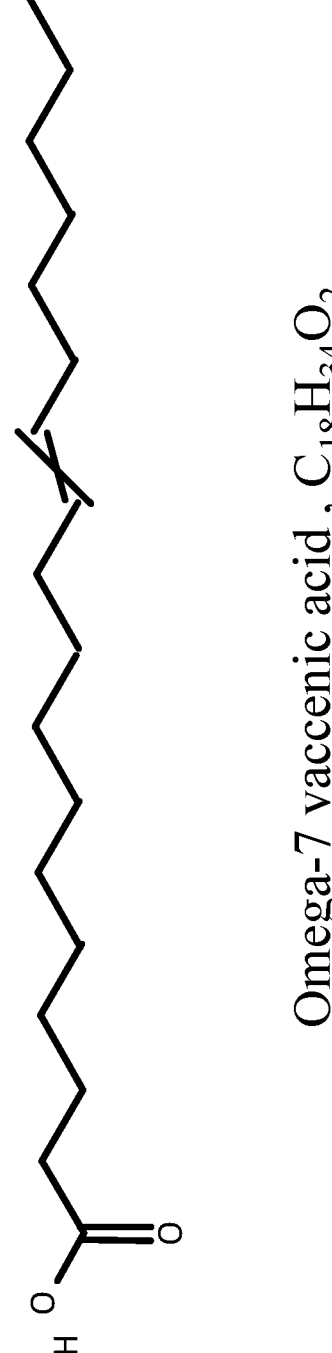
Figure 3G:
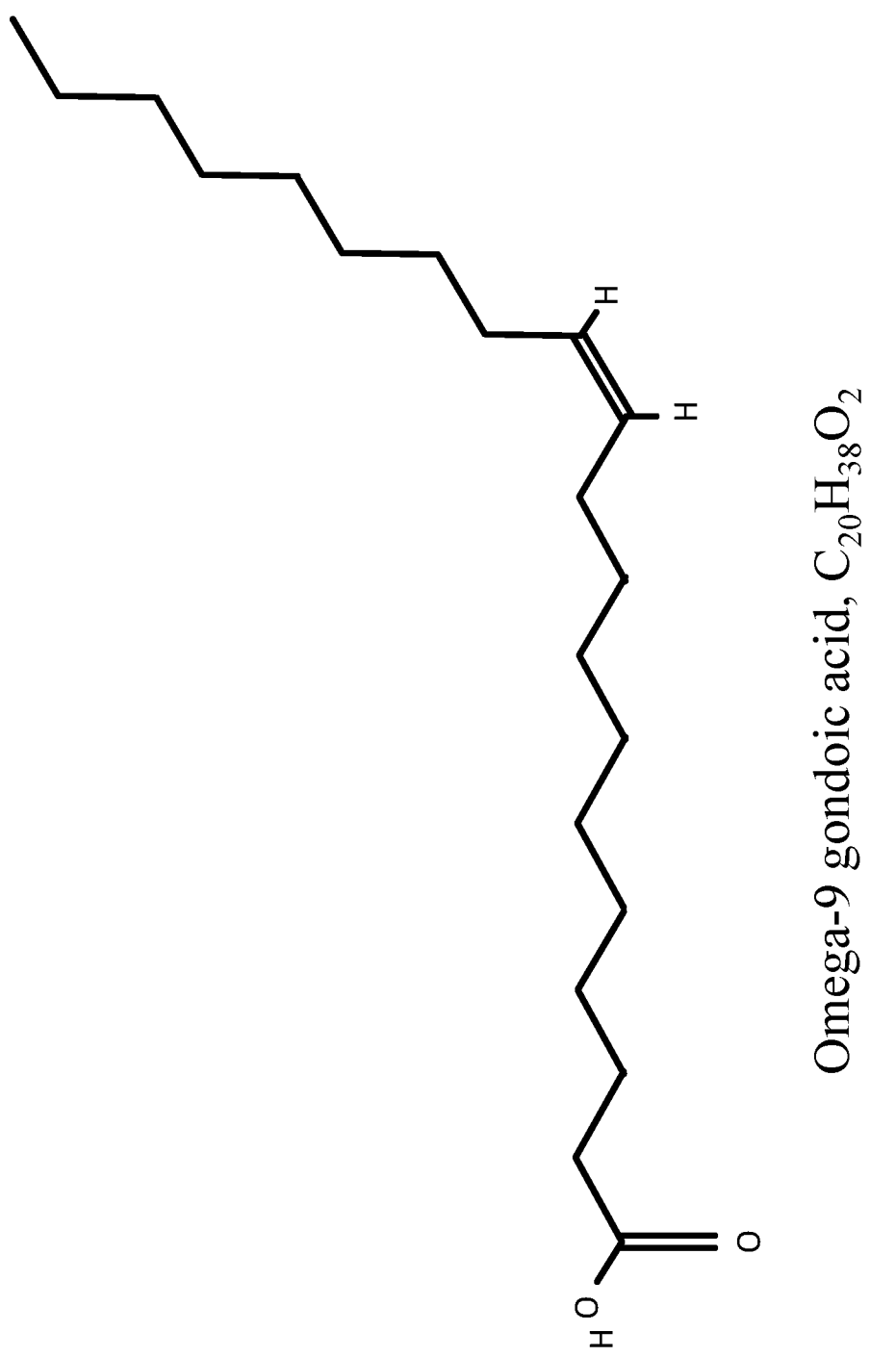
Figure 3H:
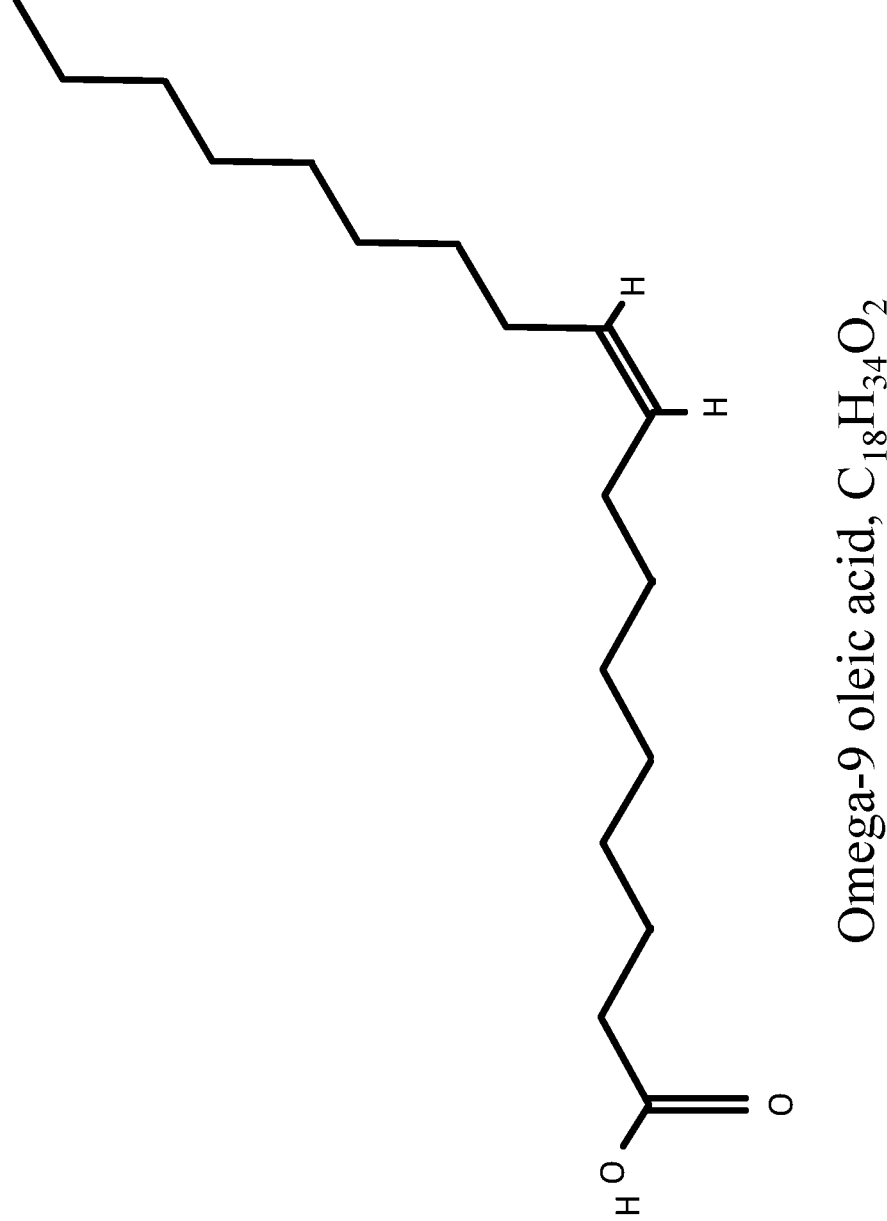

In some embodiments, the omega fatty acid may include an anti-inflammatory omega unsaturated fatty acid. In some embodiments, the omega fatty acid may include an omega-3 fatty acid. An omega-3 fatty acid may include α-linolenic acid (ALA) (FIG. 3A), docosahexaenoic acid (DHA) (FIG. 3B), eicosapentaenoic acid (EPA) (FIG. 3C), or octadecatetraenoic acid (FIG. 3D). The omega-3 fatty acid may include some other type of omega-3 fatty acid. In one embodiment, the omega fatty acid may include an omega-7 fatty acid. An omega-7 fatty acid may include palmitoleic acid (FIG. 3E) or vaccenic acid (FIG. 3F). An omega-7 fatty acid may include some other type of omega-7 fatty acid. In certain embodiments, the omega fatty acid may include an omega-9 fatty acid. An omega-9 fatty acid may include gondoic acid (FIG. 3G) or oleic acid (FIG. 3H). An omega-9 fatty acid may include some other type of omega-9 fatty acid. In some embodiments, an omega fatty acid may include some other type of unsaturated fatty acid.

Omega unsaturated fatty acids have anti-inflammatory properties and can reduce inflammation and suppress immune responses. Like other anti-inflammatory agents, omega fatty acids may lower the levels of cytokines (Simopoulos, 2002; Fritsche; Calder, 2017).

In some embodiments, ALA may be extracted from plant seeds, such as flax seeds or hemp seeds. DHA or EPA may be extracted from fish, such as salmon or pollock. In certain embodiments, omega-7 or omega-9 fatty acids may be extracted from fish. Table 3, below, shows the percentage of the major unsaturated fatty acids that are found in various fish oils. Table 4, below, shows the percentage of the omega-3, omega-7, and omega-9 fatty acids that are found in various fish oils.

TABLE 3

| Major Unsaturated Fatty Acids that are Found in Various Fish Oils | | |
|---|---|---|
| Unsaturated fatty acid | Salmon | Pollock |
| Omega-3 alpha-linolenic acid | 1.73% | 0.64% |
| Omega-3 docosahexaenoic acid | 11.60% | 6.75% |
| Omega-3 eicosapentaenoic acid | 9.69% | 10.15% |
| Omega-3 octadecatetraenoic acid | 3.07% | 3.04% |
| Omega-7 palmitoleic acid | 3.88% | 4.92% |
| Omega-7 vaccenic acid | 1.83% | 4.18% |
| Omega-9 gondoic acid | 1.92% | 3.34% |
| Omega-9 oleic acid | 9.77% | 10.73% |

TABLE 4

| Percentage of the Omega Fatty Acids Found in Various Fish Oils | | |
|---|---|---|
| Unsaturated fatty acid | Salmon | Pollock |
| Omega-3 unsaturated fatty acids | 31.48% | 22.50% |
| Omega-7 unsaturated fatty acids | 5.70% | 9.10% |
| Omega-9 unsaturated fatty acids | 13.16% | 15.43% |

In nature ALA, DHA and EPA can exist as triacylglycerols or triglycerides where three fatty acids are combined with glycerol. Single or mono ethyl ester forms of the fatty acids may be isolated by esterifying the triglyceride form with ethanol. This process allows an entity to readily concentrate and purify fatty acids.

Pharmaceutical Compositions

In another aspect, the present disclosure provides a pharmaceutical composition that comprises a cannabinoid and a pharmaceutically acceptable carrier. In an exemplary embodiment, the cannabinoid is chosen from i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA.

In another aspect, the present disclosure provides a pharmaceutical composition that comprises a cannabinoid, an omega fatty acid, and a pharmaceutically acceptable carrier. In an exemplary embodiment, the cannabinoid is chosen from i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA.

In one embodiment, the omega fatty acid of the pharmaceutical composition may include multiple types of omega fatty acids. For example, the pharmaceutical composition may include a mixture of different types of fatty acids. A majority (e.g., by weight, volume, or some other measurement) of the omega fatty acids in the mixture may include DHA. In other embodiments, a majority of the omega fatty acids in the mixture may include EPA. In certain embodiments, a majority of the omega fatty acids in the mixture may include DHA and EPA.

In one or more embodiments, a majority of the plurality of omega fatty acids may include a mixture of DHA and EPA.

The active agent may be formulated in a pharmaceutical composition to be administered to a subject in a formulation adapted to the chosen route of administration. The formulation may include one suitable for oral, rectal, vaginal, topical, nasal, ophthalmic, or parenteral (including subcutaneous, intramuscular, intraperitoneal, and intravenous) administration.

The pharmaceutically acceptable carrier may include, for example, an excipient, a diluent, a solvent, an accessory ingredient, a stabilizer, a protein carrier, or a biological compound. Non-limiting examples of solvents include propanediol, propylene glycol, and polysorbate 80. In some embodiments, an oil may be used as a solvent. Non-limiting examples of an oil include a vegetable oil such as corn oil, peanut oil, or coconut oil. Non-limiting examples of a protein carrier includes keyhole limpet hemocyanin (KLH), bovine serum albumin (BSA), ovalbumin, or the like. Non-limiting examples of a biological compound which may serve as a carrier include a glycosaminoglycan, a proteoglycan, and albumin. The carrier may be a synthetic compound, such as dimethyl sulfoxide or a synthetic polymer, such as a polyalkyleneglycol. Ovalbumin, human serum albumin, other proteins, polyethylene glycol, or the like may be employed as the carrier. In some embodiments, the pharmaceutically acceptable carrier includes at least one compound that is not naturally occurring or a product of nature. In some embodiments, the composition including the pharmaceutically acceptable carrier is a composition that is not naturally occurring or a product of nature.

In some embodiments, the pharmaceutical composition is formulated in combination with one or more additional (for example, "second") active agent(s). For example, the pharmaceutical composition may be formulated in combination with a nonsteroidal anti-inflammatory drug (NSAIDs), such as acetylsalicylic acid, ibuprofen, naproxen, or celecoxib; a conventional synthetic disease-modifying antirheumatic drugs (DMARDs), such as methotrexate, hydroxychloroquine, sulfasalazine, leflunomide, or gold salts; a corticosteroid, such as cortisone, dexamethasone, hydrocortisone, or prednisone; a non-antibody tumor necrosis factor alpha (TNFα or TNF) inhibitor such as a xanthine derivative (pentoxifylline or bupropion); or a monoclonal antibody TNF inhibitor, such as adalimumab, etanercept, or infliximab; or a combination thereof.

In some embodiments, such a combination therapy includes at least one compound that is not naturally occurring or a product of nature. In some embodiments, the pharmaceutical composition includes at least one non-naturally occurring therapeutic or prophylactic agent.

The composition may be conveniently presented in unit dosage form and may be prepared by any of the methods well-known in the art of pharmacy. All methods include the step of bringing the active agent into association with a pharmaceutical carrier. In some embodiments, the composition may be prepared by uniformly and intimately bringing the active compound into association with a liquid carrier, a finely divided solid carrier, or both, and then, if necessary, shaping the product into the desired formulations.

A composition suitable for oral administration may be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like may also contain one or more of the following: a binder such as gum tragacanth, acacia, corn starch, or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into preparations and devices in formulations that may, or may not, be designed for sustained release or controlled release.

A formulation suitable for parenteral administration may include a sterile aqueous preparation of the active agent, or a dispersion of a sterile powder of the active agent, which is preferably isotonic with the blood of the subject. Parenteral administration of a pharmaceutical composition (for example, through an IV drip) is one form of administration. An isotonic agent may be included in the liquid preparation including, for example, a sugar; a buffer; and/or a salt including, for example, sodium chloride. A solution of the active agent may be prepared in water, optionally mixed with a nontoxic surfactant. A dispersion of the active agent may be prepared in water, ethanol, a polyol (such as glycerol, propylene glycol, liquid polyethylene glycols, and the like), a vegetable oil, or a glycerol ester, or a mixture thereof. The ultimate dosage form may be sterile, fluid, and stable under the conditions of manufacture and storage. The necessary fluidity may be achieved, for example, by using liposomes, by employing the appropriate particle size in the case of dispersions, or by using surfactants. Sterilization of a liquid preparation may be achieved by any convenient method that preserves the bioactivity of the active agent, preferably by filter sterilization. Methods for preparing a powder include vacuum drying and freeze drying of the sterile injectable solutions. Subsequent microbial contamination may be prevented using various antimicrobial agents, for example, antibacterial, antiviral and antifungal agents including parabens, chlorobutanol, phenol, sorbic acid, thimerosal, and the like. Absorption of the active agents over a prolonged period may be achieved by including agents for delaying, for example, aluminum monostearate and gelatin.

Nasal spray formulations include purified aqueous solutions of the active agent with a preservative agent and/or an isotonic agents. Such formulations may be adjusted to a pH and isotonic state compatible with the nasal mucous membranes. Formulations for rectal or vaginal administration may be presented as a suppository with a suitable carrier such as cocoa butter, or hydrogenated fats, or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations. Topical formulations may be provided in the form of a bandage, wherein the formulation is incorporated into a gauze or other structure and brought into contact with the skin.

In some embodiments, a CBD product may be prepared in a neutral medium chain triglyceride (MCT) oil. The MCT may be low in anti-inflammatory unsaturated fatty acids. An example of such an MCT may include MCT coconut oil. However, CBD is soluble in a variety of oils. Thus, certain CBD products may be prepared in an oil that may include an unsaturated fatty acid, such as an omega fatty acid. In one embodiment, preparing a CBD product in an unsaturated fatty acid may enhance the anti-inflammatory capability of the CBD product.

Administration

In another aspect, this disclosure describes administration of a cannabinoid (including, for example, a cannabinoid chosen from i) CBC, CBCA, CBD, CBDA, CBDV, CBDVA, CBG, CBGA, CBL, CBLA, CBN, CBNA, THCV, THCVA, and a combination thereof, and ii) an approximately 1:1 equimolar mixture of CBD:CBDA), as the active agent, to a subject.

In another aspect, this disclosure describes administration of a composition including a cannabinoid (including, for example, a cannabinoid chosen from i) CBC, CBCA, CBD, CBDA, CBDV, CBDVA, CBG, CBGA, CBL, CBLA, CBN, CBNA, THCV, THCVA, and a combination thereof, and ii)

an approximately 1:1 equimolar mixture of CBD:CBDA) and an omega fatty acid, as the active agent, to a subject.

The active agent may be administered alone or in a pharmaceutical composition that includes the active agent and a pharmaceutically acceptable carrier. The term "administered" encompasses administration of a prophylactically and/or therapeutically effective dose or amount of the active agent to a subject. The active agent may be administered to a subject in an effective amount to produce the desired effect.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

By a "therapeutically effective amount" is meant a sufficient amount of the compound to treat the subject at a reasonable benefit/risk ratio applicable to obtain a desired therapeutic response. It will be understood, however, that the total daily usage of the compounds and compositions will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

A composition (either a cannabinoid composition or a cannabinoid-omega fatty acid composition) as an active agent may be introduced into the subject systemically or locally. For example, in some embodiments, a composition may be introduced at a site of inflammation or the site of a tumor. The active agent may be administered to the subject in an amount effective to produce the desired effect. A composition may be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Local administration may include topical administration, administration by injection, or perfusion or bathing of an organ or tissue, for example.

A formulation may be administered as a single dose or in multiple doses. In some embodiments, a formulation may be administered once per day or more than once per day including, for example, twice per day, three times per day, or four times per day. Useful dosages of the active agent may be determined by comparing their in vitro activity and the in vivo activity in animal models. Methods for extrapolation of effective dosages in mice, and other animals, to humans are known in the art.

In some embodiments, examples of anti-inflammatory therapies which may form the basis for determining dosages and dosing regiments for a cannabinoid may be found in online at, cbdoilreview.org/cbd-cannabidiol/cbd-dosage/medium.com/cbd-origin/whats-the-best-cbd-dosage-81ec4195503b; www.projectcbd.org/how-to/cbd-dosage; or www.marijuanabreak.com/cbd-oil-dosage.

Dosage levels of the active agent in the pharmaceutical compositions may be varied to obtain an amount of the active agent which is effective to achieve the desired therapeutic response for a particular subject, composition, and mode of administration, without being toxic to the subject. The selected dosage level will depend upon a variety of factors including the activity of the particular compound employed, the route of administration, the time of administration, the rate of excretion of the particular compound being employed, the duration of the treatment, other drugs, compounds and/or materials used in combination with the composition, the age, sex, weight, condition, general health, and prior medical history of the subject being treated, and like factors well known in the medical arts.

In an exemplary embodiment, a composition may be administered to a subject in an amount of at least 5 mg, at least 10 mg, at least 20 mg, at least 30 mg, at least 40 mg, at least 50 mg, or at least 5 g. In exemplary embodiment, a composition may be administered to a subject in an amount of up to 40 mg, up to 50 mg, up to 60 mg, up to 70 mg, up to 80 mg, up to 90 mg, up to 100 mg, up to 1000 mg, up to 5 g, or up to 10 g. In an exemplary embodiment, a composition may be administered orally at least once per day including, for example, as a medication, nutritional supplement, or food additive. In a further exemplary embodiment, a composition may be administered to a subject intravenously or intramuscularly.

In another exemplary embodiment, a composition may be administered to a subject in an amount effect to provide a daily dosage of at least 0.01 mg/kg body weight, at least 0.03 mg/kg body weight, at least 0.1 mg/kg body weight, at least 0.3 mg/kg body weight, or at least 1 mg/kg body weight. In another exemplary embodiment, a composition may be administered to a subject in an amount effect to provide a daily dosage of up to 1 mg/kg body weight, up to 5 mg/kg body weight, up to 10 mg/kg body weight, or up to 20 mg/kg body weight.

A physician or veterinarian having ordinary skill in the art may determine and prescribe the effective amount of the pharmaceutical composition required. For example, a physician could start doses of the composition employed at levels lower than that required in order to achieve the desired therapeutic effect and gradually increase the dosage until the desired effect is achieved.

Methods of Using a Cannabinoid and Cannabinoid-Omega Fatty Acid Composition as an Anti-Inflammatory Agent or Immunosuppressant In another aspect, this disclosure describes methods that include using a cannabinoid to treat or prevent inflammation and/or as an immunosuppressant. In another aspect, this disclosure describes methods that include using a cannabinoid-omega fatty acid composition to treat or prevent inflammation and/or as an immunosuppressant.

As further described in the Examples and discussed above, the individual cannabinoids CBC, CBCA, CBD, CBDA, CBDV, CBDVA, CBG, CBGA, CBL, CBLA, CBN, CBNA, THCV and THCVA, and a 1:1 equimolar mixture of CBD:CBDA each showed potential as anti-inflammatory agents, immunosuppressants and/or antioxidants (see Tables 7 and 8). Accordingly, the present disclosure provides in some embodiments methods of treating or preventing inflammation and/or autoimmunity in a subject in need thereof using the cannabinoid compositions described herein.

As further described in the Examples and discussed above, i) the individual cannabinoids CBC, CBCA, CBD, CBDA, CBDV, CBDVA, CBG, CBGA, CBL, CBLA, CBN, CBNA, THCV, and THCVA and an omega fatty acid, and ii) a 1:1 equimolar mixture of CBD:CBDA and an omega fatty acid; each showed potential as anti-inflammatory agents, immunosuppressants and/or antioxidants (see Tables 15-20, below). Accordingly, the present disclosure provides in some embodiments methods of treating or preventing inflammation and/or autoimmunity in a subject in need thereof using the cannabinoid-omega fatty acid compositions described herein.

In another embodiment, the present disclosure provides methods for inducing autophagy in a subject in need thereof comprising administering an effective amount of a composition comprising a cannabinoid chosen from: i) CBL, CBLA, THCVA, and ii) an approximately 1:1 equimolar mixture of CBD:CBDA.

In another embodiment, the present disclosure provides methods for inducing autophagy in a subject in need thereof comprising administering an effective amount of a composition comprising a cannabinoid chosen from: i) CBL, CBLA, THCVA, and ii) an approximately 1:1 equimolar mixture of CBD:CBDA; and iii) an omega fatty acid. In some embodiments, the induction of the autophagy may treat or prevent cancer. The induction of the autophagy may reduce inflammation in the subject.

Given the side effects associated with existing anti-inflammation treatments—for example, TNF inhibitors cause a number of side effects that may be fatal, and many patients are nonresponsive to them (Jain and Singh, 2013; Hadam et al., 2014)—one or more compositions (either cannabinoid compositions or cannabinoid-omega fatty acid compositions) identified herein as anti-inflammatory agents or immunosuppressants could be used as a replacement for one or more of a more toxic anti-inflammatory drugs that is currently in use. Additionally or alternatively, as further described herein, a composition may be used in combination with another anti-inflammation drug or drug cocktail.

In one embodiment, a composition is administered in an amount effective to treat or prevent inflammation. Administration of the composition may be performed before, during, or after a subject develops inflammation and/or or manifests symptoms of inflammation. Therapeutic treatment is initiated after the development of inflammation. Treatment initiated after the development of inflammation, or after manifestation of a symptom of inflammation, may result in decreasing the severity of a symptom, or completely removing a symptom. For example, a composition may be administered before, during, or after a subject develops symptoms of an autoimmune disease. Exemplary symptoms of an autoimmune disease or inflammation include fatigue, joint pain and/or swelling, skin problems, abdominal pain and/or digestive issues, recurring fever, swollen glands, etc.

In another embodiment, a composition may be administered prophylactically in an amount effective to prevent or delay the development of inflammation in a subject. Treatment that is prophylactic, for instance, may be initiated before a subject develops inflammation, or manifests symptoms of inflammation. An example of a subject who is at particular risk of developing inflammation is a person with an autoimmune disease including, for example, rheumatoid arthritis Crohn's disease, lupus erythematosus (SLE), Sjogren syndrome, immune thrombocytopenic purpura (ITP), myasthenia gravis, sarcoidosis, Addison's disease, autoimmune hepatitis, Celiac disease, Grave's disease, idiopathic thrombocytopenic purpura, multiple sclerosis, primary biliary cirrhosis, psoriatic disease, scleroderma, systemic lupus, etc.

Administration of a composition may occur before, during, and/or after other treatments including, for example, additional active agent(s). In an exemplary embodiment, such combination therapy may involve the administration of a composition before, during and/or after the use of other therapeutics used to treat inflammatory conditions or autoimmune diseases including, for example, nonsteroidal anti-inflammatory drugs (NSAIDs), conventional synthetic disease-modifying antirheumatic drugs (DMARDs), corticosteroids, non-antibody tumor necrosis factor alpha (TNFα or TNF) inhibitors, and monoclonal antibody TNF inhibitors.

The administration of a composition may be separated in time from the administration of another active agent by hours, days, or even weeks; alternatively, the other active agent(s) may be administered concurrently, either together in the same composition or in separate compositions. Additionally or alternatively, the administration of a composition may be combined with another active agent or modality such as, for example, non-drug therapies, such as, but not limited to, radiotherapy, heat therapy, cryotherapy, electrical therapy, massage, and acupuncture.

The results described in Example 4—that CBL, CBLA, and a 1:1 equimolar mixture of CBD:CBDA were effective at inducing autophagy—are noteworthy, given the increasing evidence that autophagy plays an important role in regulating the immune system (Kuballa et al., 2012) and suggest these compounds may serve as therapeutics for the treatment of inflammatory conditions and autoimmune diseases. Autophagy has been demonstrated to be downregulated in a number of autoimmune diseases (Wang and Muller, 2015; Wang et al., 2017) and agents that may induce autophagy have been proposed as potential new therapeutics for the treatment of inflammatory conditions and autoimmune diseases (Nguyen et al., 2013).

Superior immunosuppressant activities of the 1:1 equimolar mixture of CBD:CBDA were observed in the in vitro cellular studies of Examples 2 and 4. These results further indicate the potential for this composition as a potential therapeutic for the treatment of inflammatory conditions or autoimmune diseases. Although there are some differences between the physiology of mice and humans, mouse animal studies are highly predictive and widely utilized to determine the suitability of therapeutics to treat inflammation and autoimmune diseases in humans (Mestas and Hughes, 2004; Jameson and Masopust, 2018), and the results of the mouse LPS cytokine studies of Example 3 further demonstrated the potential of the 1:1 equimolar mixture of CBD:CBDA as a therapeutic for treating inflammation and autoimmune diseases.

Methods of Using the Compositions as Anti-Cancer Therapeutics

In a further aspect, this disclosure describes methods that include using a cannabinoid or cannabinoid-omega fatty acid composition as an anti-cancer therapeutic.

CBD has been used as a nutritional supplement to treat cancer and recent scientific reports have validated its potential as an anticancer agent (Kenyon et al., 2018; Sulé-Suso et al, 2019). The results described in Example 4—that CBL, CBLA, THCVA, and a 1:1 equimolar mixture of CBD: CBDA were effective at inducing autophagy—might explain the potential of CBD as an anticancer agent. Moreover, the results of Example 4 indicate for the first time that CBL, CBLA, THCVA, and a 1:1 equimolar mixture of CBD: CBDA may be useful anticancer agents. Defects in autophagy cause cancer (Edinger and Thompson, 2003; Choi, 2012) and agents that induce autophagy have been proposed as potential new therapeutics for the treatment of cancer (Mukhtar, et al., 2012; Byun et al., 2017; Jiang et al., 2019). Additionally, anti-inflammatory agents have been touted as possible agents for the treatment of cancer (Rayburn et al., 2009; Todoric et al., 2016). Because the cannabinoids show great promise as anti-inflammatory agents, they could be used to treat cancer.

In some embodiments, the cancer includes a lung cancer. (See Sulé-Suso et al, 2019). In some embodiments, the cancer includes breast cancer (Kenyon et al., 2018). In some embodiments, the cancer includes glioma (Kenyon et al., 2018). In some embodiments, the cancer includes cervical cancer (Lukhele et al. BMC Complement Altern Med. 2016; 16:335). In some embodiments, the cancer includes colon cancer (Aviello et al. J Mol Med (Berl). 2012; 90:925-934).

Additionally or alternatively, cancers to be treated include, but are not limited to, melanoma, basal cell carcinoma, colorectal cancer, pancreatic cancer, breast cancer, prostate cancer, lung cancer (including small-cell lung carcinoma and non-small-cell lung carcinoma), leukemia, lymphoma, sarcoma, ovarian cancer, Kaposi's sarcoma, Hodgkin's lymphoma, Non-Hodgkin's lymphoma, multiple myeloma, neuroblastoma, rhabdomyosarcoma, primary thrombocytosis, primary macroglobulinemia, small-cell lung tumors, primary brain tumors, stomach cancer, head and neck cancers, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, kidney cancer, endometrial cancer, glioblastoma, mesothelioma, oral leukoplakia, Barrett's esophageal cancer, and adrenal cortical cancer. In some aspects, the cancer is a primary cancer. In some aspects, the cancer is metastatic, including, but not limited to a metastatic melanoma, metastatic breast cancer, or metastatic colorectal cancer.

In one embodiment, a composition is administered in an amount effective to treat or prevent a cancer. Administration of the composition may be performed before, during, or after a subject develops cancer and/or or manifests symptoms of cancer. Therapeutic treatment is initiated after the development of cancer. Treatment initiated after the development of cancer, or after manifestation of a symptom of cancer, may result in decreasing the severity of a symptom, or completely removing a symptom. For example, a composition may be administered before, during, or after a subject develops symptoms of a cancer. Treatment of a cancer may include, for example, killing tumor cells, reducing the growth of tumor cells, reducing tumor size, inducing apoptosis in a tumor cell, and/or inducing tumor cells syncytial formation.

The efficacy of such methods for the treatment of cancer may be assessed by any of various parameters well known in the art. Such methods include, but are not limited to, determinations of a reduction in tumor size, determinations of the inhibition of the growth, spread, invasiveness, vascularization, angiogenesis, and/or metastasis of a tumor, determinations of the inhibition of the growth, spread, invasiveness and/or vascularization of any metastatic lesions, determinations of tumor infiltrations by immune system cells, and/or determinations of an increased delayed type hypersensitivity reaction to tumor antigen. The efficacy of treatment may also be assessed by the determination of a delay in relapse or a delay in tumor progression in the subject or by a determination of survival rate of the subject, for example, an increased survival rate at one or five years post treatment. As used herein, a relapse is the return of a tumor or neoplasm after its apparent cessation.

In another embodiment, a composition may be administered prophylactically in an amount effective to prevent or delay the development of cancer in a subject. Treatment that is prophylactic, for instance, may be initiated before a subject develops cancer, or manifests symptoms of cancer. An example of a subject who is at particular risk of developing cancer is a person who has been exposed to a carcinogen or who has tested positive for a genetic marker of cancer risk (for example, BRCA1 or BRCA2).

Administration of a composition may occur before, during, and/or after other treatments including, for example, additional active agent(s) or therapeutic agent(s). In an exemplary embodiment, such combination therapy may involve the administration of a composition before, during and/or after the use of other therapeutics used to treat cancer.

The administration of a composition may be separated in time from the administration of another active agent or therapeutic agent by hours, days, or even weeks; alternatively, the other active agent(s) or therapeutic agent(s) may be administered concurrently, either together in the same composition or in separate compositions. Additionally or alternatively, the administration of a composition may be combined with another active agent or modality such as, for example, non-drug therapies, such as, but not limited to, radiotherapy, heat therapy, cryotherapy, electrical therapy, massage, and acupuncture.

In some embodiments, the administration of a composition may allow for the effectiveness of a lower dosage of other therapeutic modalities when compared to the administration of the other therapeutic modalities alone, providing relief from the toxicity observed with the administration of higher doses of the other modalities.

As used herein, an additional active agent or therapeutic agent may be an agent whose use for the treatment of cancer is known to the skilled artisan. Such treatments include, but are not limited to, surgical resection, radiation therapy, hormone therapy, vaccines, antibody based therapies, whole body irradiation, bone marrow transplantation, peripheral blood stem cell transplantation, the administration of a chemotherapeutic agent, cytokines, antiviral agents, immune enhancers, tyrosine kinase inhibitors, protein kinase C (PKC) modulator (such as, for example, the PKC activator ingenol 3-angelate (PEP005) or the PKC inhibitor bisindolylmaleimid (enzastaurin), signal transduction inhibitors, antibiotics, antimicrobial agents, a TLR agonist (such as for example, bacterial lipopolysaccharides (LPS) or a CpG oligonucleotide (ODN)), an inhibitor of IDO, such as, for example, 1-MT, and adjuvants.

A chemotherapeutic agent may be, for example, a cytotoxic chemotherapy agent, such as, for example, epidophyllotoxin, mitoxantrone, platinum coordination complexes such as cisplatin and carboplatin, leucovorin, tegafur, paclitaxel, docetaxol, vincristine, vinblastine, methotrexate, cyclophosphamide, gemcitabine, estramustine, carmustine, adriamycin (doxorubicin), etoposide, arsenic trioxide, irinotecan, epothilone derivatives, navelbene, CPT-11, anastrazole, letrazole, capecitabine, reloxafine, ifosamide, and droloxafine.

A chemotherapeutic agent may be, for example, an alkylating agent, such as, for example, irofulven, nitrogen mustards (such as chlorambucil, cyclophosphamide, ifosfamide, mechlorethamine, melphalan, and uracil mustard), aziridines (such as thiotepa), methanesulphonate esters (such as busulfan), nitroso ureas (such as carmustine, lomustine, and streptozocin), platinum complexes (such as cisplatin and carboplatin), and bioreductive alkylators (such as mitomycin, procarbazine, dacarbazine and altretamine), ethylenimine derivatives, alkyl sulfonates, triazenes, pipobroman, temozolomide, triethylene-melamine, and triethylenethiophosphoramine.

A chemotherapeutic agent may be an antimetabolite, such as, for example, a folate antagonist (such as methotrexate and trimetrexate), a pyrimidine antagonist (such as fluorouracil, fluorodeoxyuridine, CB3717, azacitidine, cytarabine, gemcitabine, and floxuridine), a purine antagonist (such as mercaptopurine, 6-thioguanine, fludarabine, and pentostatin), a ribonucleotide reductase inhibitor (such as hydroxyurea), and an adenosine deaminase inhibitor.

A chemotherapeutic agent may be a DNA strand-breakage agent (such as, for example, bleomycin), a topoisomerase II inhibitor (such as, for example, amsacrine, dactinomycin, daunorubicin, idarubicin, mitoxantrone, doxorubicin, etoposide, and teniposide), a DNA minor groove binding agent (such as, for example, plicamydin), a tubulin interactive agent (such as, for example, vincristine, vinblastine, and paclitaxel), a hormonal agent (such as, for example, estrogens, conjugated estrogens, ethinyl estradiol, diethyl stilbesterol, chlortrianisen, idenestrol, progestins (such as hydroxyprogesterone caproate, medroxyprogesterone, and megestrol), and androgens (such as testosterone, testosterone propionate, fluoxymesterone, and methyltestosterone), an adrenal corticosteroid (such as, for example, prednisone, dexamethasone, methylprednisolone, and prednisolone), a leutinizing hormone releasing agent or gonadotropin-releasing hormone antagonist (such as, for example, leuprolide acetate and goserelin acetate), an antihormonal agent (such as, for example, tamoxifen), an antiandrogen agent (such as flutamide), an antiadrenal agent (such as mitotane and aminoglutethimide), and a natural product or derivative thereof (such as, for example, vinca alkaloids, antibiotics, enzymes and epipodophyllotoxins, including, for example vinblastine, vincristine, vindesine, bleomycin, dactinomycin, daunorubicin, doxorubicin, epirubicin, idarubicin, ara-C, paclitaxel, mithramycin, deoxyco-formycin, mitomycin-C, L-asparaginase, and teniposide.

In some embodiments, at least one additional therapeutic agent includes radiation therapy. In some aspects, radiation therapy includes localized radiation therapy delivered to the tumor. In some aspects, radiation therapy includes total body irradiation.

Cytokines include, but are not limited to, IL-1$\alpha$, IL-1$\beta$, IL-2, IL-3, IL-4, IL-6, IL-8, IL-9, IL-10, IL-12, IL-13, IL-15, IL-18, IL-19, IL-20, IFN-$\alpha$, IFN-$\beta$, IFN-$\gamma$, tumor necrosis factor (TNF), transforming growth factor-$\beta$ (TGF-$\beta$), granulocyte colony stimulating factor (G-CSF), macrophage colony stimulating factor (M-CSF), granulocyte-macrophage colony stimulating factor (GM-CSF), and or Flt-3 ligand. Antibody therapeutics, include, for example, trastuzumab (Herceptin) and antibodies to cytokines, such as IL-10 and TGF-$\beta$.

In some embodiments, a measurement of response to treatment observed after administering both a composition and an additional active agent or therapeutic agent is improved over the same measurement of response to treatment observed after administering either the composition alone or the additional agent alone. In some embodiments, the administration of a composition as described herein and the at least one additional therapeutic agent demonstrate therapeutic synergy. As used herein, a combination may demonstrate therapeutic synergy if it is therapeutically superior to one or other of the constituents used at its optimum dose (Corbett et al., 1982, Cancer Treatment Reports; 66:1187. In some embodiments, a combination demonstrates therapeutic synergy if the efficacy of a combination is characterized as more than additive actions of each constituent.

Kits

This disclosure further describes a kit that contains at least one cannabinoid or composition described herein, together with instructions for use. This disclosure also further describes a kit that contains at least one cannabindoid, an omega fatty acid, or composition described herein, together with instructions for use. In some embodiments, the instructions for use provide instructions for use in the treatment or prevention of inflammation and/or autoimmunity. Optionally, the kit includes a pharmaceutically acceptable carrier. The carrier may be separately provided, or it may be present in a composition that includes the compound. Optionally, the kit may further include one or more additional active agents which may be co-administered with the composition. The one or more active agent(s) may have cumulative or complementary activities, as described in more detail elsewhere herein.

EXEMPLARY EMBODIMENTS

1. A pharmaceutical composition comprising a cannabinoid chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA; wherein the pharmaceutical composition is formulated for use as an anti-inflammatory agent and/or an immunosuppressant.

2. The pharmaceutical composition of embodiment 1, wherein the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA.

3. The pharmaceutical composition of embodiment 1, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

4. The pharmaceutical composition of embodiment 1, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

5. The pharmaceutical composition of embodiment 1, wherein the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA.

6. The pharmaceutical composition of embodiment 5, wherein the cannabinoid is chosen from the CBCA, CBDA, CBDV, CBDVA, CBGA, CBL, CBLA, CBN, CBNA, and any combination thereof.

7. The pharmaceutical composition of embodiment 6, wherein the cannabinoid is chosen from the CBDV, CBL, CBLA, CBN, CBNA and any combination thereof.

8. The pharmaceutical composition of embodiment 1, wherein the cannabinoid is chosen from i) the CBCA, CBD, CBDA, CBDV, CBDVA, CBG, CBL, CBLA, CBN, CBNA, THCV, and THCVA, and ii) the approximately 1:1 equimolar mixture of CBD:CBDA.

9. The pharmaceutical composition of embodiment 1, wherein the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

10. The pharmaceutical composition of any one of embodiments 1, 2, 4, 5, 8, or 9, wherein the cannabinoid is the approximately 1:1 equimolar mixture of CBD:CBDA.

11. The pharmaceutical composition of embodiment 10, wherein the pharmaceutical composition is substantially free of other cannabinoids.

12. The pharmaceutical composition of embodiment 10 or 11, wherein the cannabinoid consists essentially of the approximately 1:1 equimolar mixture of CBD:CBDA.

13. The pharmaceutical composition of any one of embodiments 10 to 12, wherein the cannabinoid consists essentially of a 1:1 equimolar mixture of CBD:CBDA.

14. The pharmaceutical composition of any one of the preceding embodiments, wherein the pharmaceutical composition reduces cytokine levels in vivo or in vitro.

15. A pharmaceutical composition comprising a cannabinoid chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA; wherein the pharmaceutical composition is formulated to have antioxidant activity.

16. The pharmaceutical composition of embodiment 15, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

17. The pharmaceutical composition of embodiment 15, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

18. The pharmaceutical composition of embodiment 15, wherein the cannabinoid is chosen from the CBC, CBCA, CBD, CBDA, CBDV, CBDVA, CBG, CBGA, CBL, CBLA, CBN, CBNA, THCV, and THCVA.

19. The pharmaceutical composition of embodiment 15, wherein the cannabinoid is chosen from the CBDV, CBL, CBLA, CBN, CBNA, and any combination thereof.

20. The pharmaceutical composition of embodiment 15, wherein the cannabinoid is chosen from i) the CBD, CBDA, CBDV, CBDVA, CBG, and THCV and ii) the approximately 1:1 equimolar mixture of CBD:CBDA.

21. The pharmaceutical composition of any one of embodiments 15, 17, or 20, wherein the cannabinoid is the approximately 1:1 equimolar mixture of CBD:CBDA.

22. The pharmaceutical composition of embodiment 21, wherein the pharmaceutical composition is substantially free of other cannabinoids.

23. The pharmaceutical composition of embodiment 21 or 22, wherein the cannabinoid consists essentially of the approximately 1:1 equimolar mixture of CBD:CBDA.

24. The pharmaceutical composition of any one of embodiments 21 to 23, wherein the cannabinoid consists essentially of a 1:1 equimolar mixture of CBD:CBDA.

25. A pharmaceutical composition comprising a cannabinoid chosen from: i) CBL, CBLA, and THCVA, and any mixture thereof; and ii) an approximately 1:1 equimolar mixture of CBD:CBDA, wherein the pharmaceutical composition is formulated to induce autophagy in vivo or in vitro.

26. The pharmaceutical composition of embodiment 25, wherein the cannabinoid is chosen from: i) the CBL, CBLA, and a mixture thereof; and ii) the approximately 1:1 equimolar mixture of CBD:CBDA.

27. The pharmaceutical composition of embodiment 26, wherein the cannabinoid is chosen from the CBL, CBLA, and a mixture thereof.

28. The pharmaceutical composition of embodiment 25 or 26, wherein the cannabinoid is chosen from the approximately 1:1 equimolar mixture of CBD:CBDA.

29. The pharmaceutical composition of embodiment 28, wherein the pharmaceutical composition is substantially free of other cannabinoids.

30. The pharmaceutical composition of embodiment 28 or 29, wherein the cannabinoid consists essentially of the approximately 1:1 equimolar mixture of CBD:CBDA.

31. The pharmaceutical composition of any one of embodiments 28 to 30, wherein the cannabinoid consists essentially of a 1:1 equimolar mixture of CBD:CBDA.

32. A pharmaceutical composition comprising an approximately 1:1 equimolar mixture of CBD:CBDA.

33. The pharmaceutical composition of embodiment 32, wherein the pharmaceutical composition is substantially free of other cannabinoids.

34. The pharmaceutical composition of embodiment 32 or 33, wherein the cannabinoid consists essentially of the approximately 1:1 equimolar mixture of CBD:CBDA.

35. The pharmaceutical composition of any one of embodiments 32 to 34, wherein the cannabinoid consists essentially of a 1:1 equimolar mixture of CBD:CBDA.

36. The pharmaceutical composition of embodiment 32, wherein the pharmaceutical composition comprises an additional cannabinoid chosen from CBC, CBCA, CBDV, CBDVA, CBG, CBGA, CBL, CBLA, CBN, CBNA, THCV, THCVA, and any combination thereof.

37. The pharmaceutical composition of any one of claims 1 to 36, wherein the composition further comprises a pharmaceutical carrier.

38. The pharmaceutical composition of any one of embodiments 1 to 37, wherein the composition further comprises a nonsteroidal anti-inflammatory drug (NSAIDs), a conventional synthetic disease-modifying antirheumatic drug (DMARDs), a corticosteroid, a non-antibody tumor necrosis factor alpha inhibitor, or a monoclonal antibody TNF inhibitor, or a combination thereof.

39. The pharmaceutical composition of any one of embodiments 1 to 38, wherein the composition is formulated for use as an anti-cancer agent.

40. A method of using the composition of any one of embodiments 1 to 39, the method comprising administering an effective amount of the composition to a subject in need thereof.

41. A method for treating or preventing inflammation and/or autoimmunity in a subject, the method comprising administering to the subject a composition comprising an effective amount of a cannabinoid chosen from i) CBC, CBCA, CBD, CBDA, CBDV, CBDVA, CBG, CBGA, CBL, CBLA, CBN, CBNA, THCV, THCVA, and any combination thereof; and ii) an approximately 1:1 equimolar mixture of CBD:CBDA.

42. The method of embodiment 41, wherein the subject in need thereof is has an autoimmune disease.

43. The method of embodiment 42, wherein the autoimmune disease comprises rheumatoid arthritis Crohn's disease, lupus erythematosus (SLE), Sjogren syndrome, immune thrombocytopenic purpura (ITP), myasthenia gravis, sarcoidosis, Addison's disease, autoimmune hepatitis, Celiac disease, Grave's disease, idiopathic thrombocytopenic purpura, multiple sclerosis, primary biliary cirrhosis, psoriatic disease, scleroderma, or systemic lupus.

44. The method of any one of embodiments 41 to 43, wherein treating or preventing inflammation comprises treating or preventing a symptom of inflammation.

45. The method of any one of embodiments 41 to 44, wherein the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA.

46. The method of any one of embodiments 41 to 44, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

47. The method of any one of embodiment 41 to 44, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

48. The method of any one of embodiments 41 to 44, wherein the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA.

49. The method of any one of embodiments 41 to 44, wherein the cannabinoid is chosen from the CBCA, CBDA, CBDV, CBDVA, CBGA, CBL, CBLA, CBN, CBNA, and any combination thereof.

50. The method of any one of embodiments 41 to 44, wherein the cannabinoid is chosen from the CBDV, CBL, CBLA, CBN, CBNA, and any combination thereof.

51. The method of any one of embodiments 41 to 44, wherein the cannabinoid is chosen from i) the CBCA, CBDA, CBD, CBDV, CBDVA, CBG, CBGA, CBL, CBLA, CBN, CBNA, THCV, and THCVA, and ii) the approximately 1:1 equimolar mixture of CBD:CBDA.

52. The method of any one of embodiments 41 to 44, wherein the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

53. The method of any one of embodiments 41 to 44, wherein the cannabinoid is the approximately 1:1 equimolar mixture of CBD:CBDA.

54. The method of any one of embodiments 41 to 44, wherein the pharmaceutical composition is substantially free of other cannabinoids.

55. The method of any one of claims 41 to 44, wherein the cannabinoid consists essentially of the approximately 1:1 equimolar mixture of CBD:CBDA.

56. The method of any one of embodiment 41 to 44, wherein the cannabinoid consists essentially of the 1:1 equimolar mixture of CBD:CBDA.

57. The method of any one of embodiment 41 to 56, wherein the method reduces elevated cytokine levels in the patient.

58. The method of any one of embodiments 41 to 57, the method further comprising administering to the subject an effective amount of an additional active agent.

59. The method of embodiment 63, wherein the additional active agent is chosen from a nonsteroidal anti-inflammatory drug (NSAIDs), a conventional synthetic disease-modifying antirheumatic drug (DMARDs), a corticosteroid, a non-antibody tumor necrosis factor alpha inhibitor, or a monoclonal antibody TNF inhibitor, and any combination thereof.

60. A method for inducing autophagy in a patient in need thereof comprising administering to the patient an effective amount of a pharmaceutical composition comprising a cannabinoid chosen from: i) CBL, CBLA, and THCVA, and any mixture thereof; and ii) an approximately 1:1 equimolar mixture of CBD:CBDA.

61. The method of embodiment 60, wherein the cannabinoid is chosen from: i) the CBL, CBLA, and a mixture thereof; and ii) the approximately 1:1 equimolar mixture of CBD:CBDA.

62. The method of any one of embodiments 60 or 61, wherein the cannabinoid is chosen from the CBL, CBLA, and a mixture thereof.

63. The method of any one of embodiments 60 to 62, wherein the method treats or prevents cancer in the patient.

64. A method of treating or preventing cancer in a patient in need thereof comprising the method comprising administering to the subject a composition comprising an effective amount of a cannabinoid chosen from i) CBC, CBCA, CBD, CBDA, CBDV, CBDVA, CBG, CBGA, CBL, CBLA, CBN, CBNA, THCV, THCVA, and any combination thereof; and ii) an approximately 1:1 equimolar mixture of CBD:CBDA.

65. The method of embodiment 64, wherein the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA.

66. The method of embodiment 64 or 65, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

67. The method of any one of embodiments 64 to 66, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

68. The method of any one of embodiments 64 to 66, wherein the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA.

69. The method of any one of embodiments 64 to 66, wherein the cannabinoid is chosen from the CBCA, CBDA, CBDV, CBDVA, CBGA, CBL, CBLA, CBN, CBNA, and any combination thereof.

70. The method of any one of embodiments 64 to 66, wherein the cannabinoid is chosen from the CBDV, CBL, CBLA, CBN, CBNA, and any combination thereof.

71. The method of any one of embodiments 64 to 66, wherein the cannabinoid is chosen from i) the CBCA, CBDA, CBD, CBDV, CBDVA, CBG, CBGA, CBL, CBLA, CBN, CBNA, THCV, and THCVA, and ii) the approximately 1:1 equimolar mixture of CBD:CBDA.

72. The method of any one of embodiments 64 to 66, wherein the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

73. The method of any one of embodiments 64 to 66, wherein the cannabinoid is the approximately 1:1 equimolar mixture of CBD:CBDA.

74. The method of any one of embodiments 64 to 66, wherein the pharmaceutical composition is substantially free of other cannabinoids.

75. The method of any one of embodiments 64 to 66, wherein the cannabinoid consists essentially of the approximately 1:1 equimolar mixture of CBD:CBDA.

76. The method of any one of embodiments 64 to 66, wherein the cannabinoid consists essentially of the 1:1 equimolar mixture of CBD:CBDA.

77. The method any one of embodiments 60 to 76, further comprising administering and additional active agent chosen from a chemotherapeutic agent, a cytokine, an antiviral agent, an immune enhancer, a tyrosine kinase inhibitor, a protein kinase C (PKC) modulator, a signal transduction inhibitor, an antibiotic, an antimicrobial agent, a TLR agonist, an inhibitor of IDO, an adjuvant, and any combination thereof.

78. The method of any one of embodiments 60 to 77, further comprising administering radiation therapy to the patient.

79. The method of any one of embodiments 60 to 62, wherein the method further treats or prevents and inflammatory and/or autoimmune disease in the subject.

80. The method of any one of embodiments 41 to 79, wherein the composition further comprises a pharmaceutical carrier.

81. The method of any one of embodiments 41 to 80, wherein the subject is a mammal.

82. The method of embodiment 81, wherein the subject is a human.

83. A pharmaceutical composition comprising a cannabinoid chosen from: i) CBC, CBCA, CBD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA, and an omega fatty acid; wherein the pharmaceutical composition is formulated for use as an anti-inflammatory agent and/or an immunosuppressant.

84. The pharmaceutical composition of embodiment 83, wherein the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA.

85. The pharmaceutical composition of embodiment 83, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

86. The pharmaceutical composition of embodiment 83, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

87. The pharmaceutical composition of embodiment 83, wherein the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA.

88. The pharmaceutical composition of embodiment 87, wherein the cannabinoid is chosen from the CBCA, CBDA, CBDV, CBDVA, CBGA, CBL, CBLA, CBN, CBNA, and any combination thereof.

89. The pharmaceutical composition of embodiment 88, wherein the cannabinoid is chosen from the CBDV, CBL, CBLA, CBN, CBNA and any combination thereof.

90. The pharmaceutical composition of embodiment 83, wherein the cannabinoid is chosen from i) the CBCA, CBD, CBDA, CBDV, CBDVA, CBG, CBL, CBLA, CBN, CBNA, THCV, and THCVA, and ii) the approximately 1:1 equimolar mixture of CBD:CBDA.

91. The pharmaceutical composition of embodiment 83, wherein the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

92. The pharmaceutical composition of any one of embodiments 83, 84, 86, 87, 90, or 91, wherein the cannabinoid is the approximately 1:1 equimolar mixture of CBD:CBDA.

93. The pharmaceutical composition of embodiment 92, wherein the pharmaceutical composition is substantially free of other cannabinoids.

94. The pharmaceutical composition of embodiment 92 or 93, wherein the cannabinoid consists essentially of the approximately 1:1 equimolar mixture of CBD:CBDA.

95. The pharmaceutical composition of any one of embodiments 92 to 94, wherein the cannabinoid consists essentially of a 1:1 equimolar mixture of CBD:CBDA.

96. The pharmaceutical composition of any one of embodiments 83 to 95, wherein the pharmaceutical composition reduces cytokine levels in vivo or in vitro.

97. The pharmaceutical composition of any one of embodiments 83 to 95, wherein the pharmaceutical composition is formulated to induce autophagy.

98. A pharmaceutical composition comprising a cannabinoid chosen from: i) CBC, CBCA, 8BD, CBDA, CBDV, CBDVA, CBG, CBGA, CBL, CBLA, CBN, CBNA, THCV, THCVA, and any combination thereof, and ii) an approximately 1:1 equimolar mixture of CBD:CBDA, and an omega fatty acid; wherein the pharmaceutical composition is formulated to have antioxidant activity.

99. The pharmaceutical composition of embodiment 98, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

100. The pharmaceutical composition of embodiment 98, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

101. The pharmaceutical composition of embodiment 98, wherein the cannabinoid is chosen from the CBC, CBCA, CBD, CBDA, CBDV, CBDVA, CBG, CBGA, CBL, CBLA, CBN, CBNA, THCV, and THCVA.

102. The pharmaceutical composition of embodiment 98, wherein the cannabinoid is chosen from the CBDV, CBL, CBLA, CBN, CBNA, and any combination thereof.

103. The pharmaceutical composition of embodiment 98, wherein the cannabinoid is chosen from i) the CBD, CBDA, CBDV, CBDVA, CBG, and THCV and ii) the approximately 1:1 equimolar mixture of CBD:CBDA.

104. The pharmaceutical composition of any one of embodiments 98, 100, or 103, wherein the cannabinoid is the approximately 1:1 equimolar mixture of CBD:CBDA.

105. The pharmaceutical composition of embodiment 104, wherein the pharmaceutical composition is substantially free of other cannabinoids.

106. The pharmaceutical composition of embodiment 104 or 105, wherein the cannabinoid consists essentially of the approximately 1:1 equimolar mixture of CBD:CBDA.

107. The pharmaceutical composition of any one of embodiments 104 to 106, wherein the cannabinoid consists essentially of a 1:1 equimolar mixture of CBD:CBDA.

108. A pharmaceutical composition comprising a cannabinoid chosen from: i) CBL, CBLA, and THCVA, and any mixture thereof; and ii) an approximately 1:1 equimolar mixture of CBD:CBDA, and an omega fatty acid, wherein the pharmaceutical composition is formulated to induce autophagy in vivo or in vitro.

109. The pharmaceutical composition of embodiment 108, wherein the cannabinoid is chosen from: i) the CBL, CBLA, and a mixture thereof; and ii) the approximately 1:1 equimolar mixture of CBD:CBDA.

110. The pharmaceutical composition of embodiment 109, wherein the cannabinoid is chosen from the CBL, CBLA, and a mixture thereof.

111. The pharmaceutical composition of embodiment 108 or 109, wherein the cannabinoid is chosen from the approximately 1:1 equimolar mixture of CBD:CBDA.

112. The pharmaceutical composition of embodiment 111, wherein the pharmaceutical composition is substantially free of other cannabinoids.

113. The pharmaceutical composition of embodiment 111 or 112, wherein the cannabinoid consists essentially of the approximately 1:1 equimolar mixture of CBD:CBDA.

114. The pharmaceutical composition of any one of embodiments 111 to 113, wherein the cannabinoid consists essentially of a 1:1 equimolar mixture of CBD:CBDA.

115. A pharmaceutical composition comprising an approximately 1:1 equimolar mixture of CBD:CBDA and an omega fatty acid.

116. The pharmaceutical composition of embodiment 115, wherein the pharmaceutical composition is substantially free of other cannabinoids.

117. The pharmaceutical composition of embodiment 115 or 116, wherein the cannabinoid consists essentially of the approximately 1:1 equimolar mixture of CBD:CBDA.

118. The pharmaceutical composition of any one of embodiments 115 to 117, wherein the cannabinoid consists essentially of a 1:1 equimolar mixture of CBD:CBDA.

119. The pharmaceutical composition of embodiment 115, wherein the pharmaceutical composition comprises an additional cannabinoid chosen from CBC, CBCA, CBDV, CBDVA, CBG, CBGA, CBL, CBLA, CBN, CBNA, THCV, THCVA, and any combination thereof.

120. The pharmaceutical composition of any one of claims 83 to 119, wherein the composition further comprises a pharmaceutical carrier.

121. The pharmaceutical composition of any one of embodiments 83 to 120, wherein the composition further comprises a nonsteroidal anti-inflammatory drug (NSAIDs), a conventional synthetic disease-modifying antirheumatic drug (DMARDs), a corticosteroid, a non-antibody tumor necrosis factor alpha inhibitor, or a monoclonal antibody TNF inhibitor, or a combination thereof.

122. The pharmaceutical composition of any one of embodiments 83 to 121, wherein the composition is formulated for use as an anti-cancer agent.

123. The pharmaceutical composition of any one of embodiments 83 to 122, wherein the omega fatty acid comprises a plurality of omega fatty acids, and a majority of the omega fatty acids of the plurality of omega fatty acids is DHA.

124. The pharmaceutical composition of any one of embodiments 83 to 122, wherein the omega fatty acid comprises a plurality of omega fatty acids, and a majority of the omega fatty acids of the plurality of omega fatty acids is EPA.

125. The pharmaceutical composition of any one of embodiments 83 to 122, wherein the omega fatty acid comprises a plurality of omega fatty acids, and a majority of the plurality of omega fatty acids is a mixture of DHA and EPA.

126. A method of using the composition of any one of embodiments 83 to 125, the method comprising administering an effective amount of the composition to a subject in need thereof.

127. A method for treating or preventing inflammation and/or autoimmunity in a subject, the method comprising administering to the subject a composition comprising an effective amount of a cannabinoid chosen from i) CBC, CBCA, CBD, CBDA, CBDV, CBDVA, CBG, CBGA, CBL, CBLA, CBN, CBNA, THCV, THCVA, and any combination thereof; and ii) an approximately 1:1 equimolar mixture of CBD:CBDA, and an omega fatty acid.

128. The method of embodiment 127, wherein the subject in need thereof is has an autoimmune disease.

129. The method of embodiment 128, wherein the autoimmune disease comprises rheumatoid arthritis Crohn's disease, lupus erythematosus (SLE), Sjogren syndrome, immune thrombocytopenic purpura (ITP), myasthenia gravis, sarcoidosis, Addison's disease, autoimmune hepatitis, Celiac disease, Grave's disease, idiopathic thrombocytopenic purpura, multiple sclerosis, primary biliary cirrhosis, psoriatic disease, scleroderma, or systemic lupus.

130. The method of any one of embodiments 127 to 129, wherein treating or preventing inflammation comprises treating or preventing a symptom of inflammation.

131. The method of any one of embodiments 127 to 130, wherein the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA.

132. The method of any one of embodiments 127 to 130, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

133. The method of any one of embodiment 127 to 130, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

134. The method of any one of embodiments 127 to 130, wherein the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA.

135. The method of any one of embodiments 127 to 130, wherein the cannabinoid is chosen from the CBCA, CBDA, CBDV, CBDVA, CBGA, CBL, CBLA, CBN, CBNA, and any combination thereof.

136. The method of any one of embodiments 127 to 130, wherein the cannabinoid is chosen from the CBDV, CBL, CBLA, CBN, CBNA, and any combination thereof.

137. The method of any one of embodiments 125 to 128, wherein the cannabinoid is chosen from i) the CBCA, CBDA, CBD, CBDV, CBDVA, CBG, CBGA, CBL, CBLA, CBN, CBNA, THCV, and THCVA, and ii) the approximately 1:1 equimolar mixture of CBD:CBDA.

138. The method of any one of embodiments 127 to 130, wherein the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

139. The method of any one of embodiments 127 to 130, wherein the cannabinoid is the approximately 1:1 equimolar mixture of CBD:CBDA.

140. The method of any one of embodiments 127 to 130, wherein the pharmaceutical composition is substantially free of other cannabinoids.

141. The method of any one of claims 127 to 130, wherein the cannabinoid consists essentially of the approximately 1:1 equimolar mixture of CBD:CBDA.

142. The method of any one of embodiment 127 to 130, wherein the cannabinoid consists essentially of the 1:1 equimolar mixture of CBD:CBDA.

143. The method of any one of embodiment 127 to 142, wherein the method reduces elevated cytokine levels in the patient.

144. The method of any one of embodiments 127 to 143, the method further comprising administering to the subject an effective amount of an additional active agent.

145. The method of embodiment 144, wherein the additional active agent is chosen from a nonsteroidal anti-inflammatory drug (NSAIDs), a conventional synthetic disease-modifying antirheumatic drug (DMARDs), a corticosteroid, a non-antibody tumor necrosis factor alpha inhibitor, or a monoclonal antibody TNF inhibitor, and any combination thereof.

146. A method for inducing autophagy in a patient in need thereof comprising administering to the patient an effective amount of a pharmaceutical composition comprising a cannabinoid chosen from: i) CBL, CBLA, and THCVA, and any mixture thereof; and ii) an approximately 1:1 equimolar mixture of CBD:CBDA, and an omega fatty acid.

147. The method of embodiment 146, wherein the cannabinoid is chosen from: i) the CBL, CBLA, and a mixture thereof and ii) the approximately 1:1 equimolar mixture of CBD:CBDA.

148. The method of any one of embodiments 146 or 147, wherein the cannabinoid is chosen from the CBL, CBLA, and a mixture thereof.

149. The method of any one of embodiments 146 to 148, wherein the method treats or prevents cancer in the patient.

150. A method of treating or preventing cancer in a patient in need thereof comprising the method comprising administering to the subject a composition comprising an effective amount of a cannabinoid chosen from i) CBC, CBCA, CBD, CBDA, CBDV, CBDVA, CBG, CBGA, CBL, CBLA, CBN, CBNA, THCV, THCVA, and any combination thereof; and ii) an approximately 1:1 equimolar mixture of CBD:CBDA, and an omega fatty acid.

151. The method of embodiment 150, wherein the cannabinoid is chosen from: i) the CBCA, CBDA, CBDV, CBDVA, CBGA, CBL, CBLA, CBN, CBNA, THCVA, and any combination thereof, and ii) the approximately 1:1 equimolar mixture of CBD:CBDA.

152. The method of embodiment 150 or 151, wherein the cannabinoid is chosen from the CBC, CBCA, CBD, CBDA, CBDV, CBDVA, CBG, CBGA, CBL, CBLA, CBN, CBNA, THCV, THCVA, and any combination thereof.

153. The method of any one of embodiments 150 to 152, wherein the cannabinoid is chosen from: i) the CBC, CBCA, CBD, CBDA, CBDV, CBDVA, CBG, CBGA, CBL, CBLA, CBN, CBNA, and any combination thereof, and ii) the approximately 1:1 equimolar mixture of CBD:CBDA.

154. The method of any one of embodiments 150 to 152, wherein the cannabinoid is chosen from: i) the CBCA, CBDA, CBDV, CBDVA, CBGA, CBL, CBLA, CBN, CBNA, and any combination thereof, and ii) the approximately 1:1 equimolar mixture of CBD:CBDA.

155. The method of any one of embodiments 150 to 152, wherein the cannabinoid is chosen from the CBCA, CBDA, CBDV, CBDVA, CBGA, CBL, CBLA, CBN, CBNA, and any combination thereof.

156. The method of any one of embodiments 150 to 152, wherein the cannabinoid is chosen from the CBDV, CBL, CBLA, CBN, CBNA, and any combination thereof.

157. The method of any one of embodiments 150 to 152, wherein the cannabinoid is chosen from i) the CBCA, CBDA, CBD, CBDV, CBDVA, CBG, CBGA, CBL, CBLA, CBN, CBNA, THCV, and THCVA, and ii) the approximately 1:1 equimolar mixture of CBD:CBDA.

158. The method of any one of embodiments 150 to 152, wherein the cannabinoid is chosen from i) the CBCA, CBDA, CBDV, CBDVA, CBL, CBLA, CBN, CBNA, and THCVA, and ii) the approximately 1:1 equimolar mixture of CBD:CBDA.

159. The method of any one of embodiments 150 to 152, wherein the cannabinoid is the approximately 1:1 equimolar mixture of CBD:CBDA.

160. The method of any one of embodiments 150 to 152, wherein the pharmaceutical composition is substantially free of other cannabinoids.

161. The method of any one of embodiments 150 to 152, wherein the cannabinoid consists essentially of the approximately 1:1 equimolar mixture of CBD:CBDA.

162. The method of any one of embodiments 148 to 150, wherein the cannabinoid consists essentially of the 1:1 equimolar mixture of CBD:CBDA.

163. The method any one of embodiments 146 to 162, further comprising administering and additional active agent chosen from a chemotherapeutic agent, a cytokine, an anti-viral agent, an immune enhancer, a tyrosine kinase inhibitor, a protein kinase C (PKC) modulator, a signal transduction inhibitor, an antibiotic, an antimicrobial agent, a TLR agonist, an inhibitor of IDO, an adjuvant, and any combination thereof.

164. The method of any one of embodiments 146 to 163, further comprising administering radiation therapy to the patient.

165. The method of any one of embodiments 146 to 148, wherein the method further treats or prevents and inflammatory and/or autoimmune disease in the subject.

166. The method of any one of embodiments 127 to 165, wherein the composition further comprises a pharmaceutical carrier.

167. The method of any one of embodiments 127 to 166, wherein the subject is a mammal.

168. The method of embodiment 167, wherein the subject is a human.

169. The pharmaceutical composition of any one of the embodiments 83-125, wherein the omega fatty acid comprises an anti-inflammatory omega unsaturated fatty acid.

170. A method for inducing autophagy in a patient in need thereof comprising administering to the patient an effective amount of a pharmaceutical composition comprising: i) a cannabinoid; ii) an approximately 1:1 equimolar mixture of CBD:CBDA; and iii) an omega fatty acid.

171. The method of embodiment 170, wherein the induction of the autophagy treats or prevents cancer and/or reduced inflammation in the patient.

172. The method of embodiment 170, wherein the pharmaceutical composition comprises the pharmaceutical composition of any one of embodiments 83 to 125.

EXAMPLES

The Examples describe the identification of the antioxidant, anti-inflammatory, and immunosuppressant activity, as well as induction of autophagy, of a number of non-psychotropic cannabinoids and cannabinoid-omega fatty acid compositions.

As further described herein, the ability of CBDA versus CBD to suppress elevated cytokine levels was investigated using differentiated macrophage-like human THP-1 cells with stimulated cytokine expression induced by lipopolysaccharide (LPS). In these experiments, CBDA outperformed CBD. Because CBDA was superior to CBD at suppressing elevated cytokine levels, the effects of a 1:1 CBD:CBDA mixture versus CBD and CBDA alone was also examined. The 1:1 CBD:CBDA mixture suppressed cytokine expression better than CBD or CBDA and clearly had a synergistic effect versus CBD or CBDA alone. Since CBDA proved to be more effective as an anti-inflammatory agent than CBD in these studies, the immunosuppressant potential of the major non-psychotropic cannabinoids cannabichromenic acid (CBCA), cannabidiolic acid (CBDA), cannabidivarinic acid (CBDVA), cannabigerolic acid (CBGA), tetrahydrfocannabivarinic acid (THCVA) and their decarboxylated derivatives cannabichromene (CBC), cannabidiol (CBD), cannabidivarin (CBDV), cannabigerol (CBG), and tetrahydrocannabivarin (THCV), the most prominent non-psychotropic cannabinoids cannabicyclolic acid (CBLA) and cannabinolic acid (CBNA) that can be derived from the major cannabinoids and their decarboxylated derivatives cannabicyclol (CBL) and cannabinol (CBN), as well as the 1:1 equimolar mixture of CBD:CBDA was analyzed. The ability of CBD, CBDA and the 1:1 equimolar mixture of CBD:CBDA to suppress elevated cytokine levels was also evaluated in a mouse LPS cytokine model.

Materials and Methods

Cannabinoids

The major cannabinoids CBCA, CBDA, CBDVA, CBGA and THCVA and their decarboxylated derivatives, CBC, CBD, CBDV, CBG, and THCV were obtained from Cerilliant Corporation (Round Rock, Tex.). CBCVA and CBGVA and their decarboxylated derivatives CBCV and CBGV are not commercially available and were not analyzed. The CBLA and CBNA cannabinoids, as well as their decarboxylated derivatives CBL and CBN, are the most widely investigated cannabinoids which can be derivatized from the natural cannabinoids that are produced by *Cannabis*, and were obtained from Cerilliant Corporation (Round Rock, Tex.). Stock solutions of the cannabinoids were prepared at 10 mM in dimethyl sulfoxide (DMSO) for the in vitro human cellular studies and at 20 mg/mL for the mice studies. For injection into mice, an emulsified solution of the cannabinoids was prepared by diluting the 20 mg/mL DMSO solution 1:20 in phosphate buffer (PB). CBD is well tolerated in animals, such as mice and rats, and humans, and doses up to 100 mg in mice and 600 mg in humans have been used in multiple toxicological studies with no adverse side effects. (See Bergamaschi et al., 2011.) However, CBD is incredibly toxic to animal or human cells grown via tissue culture and doses of less than 5 µM can cause significant cytotoxicity (Choi et al., 2008; Liu et al., 2010; Mato et al., 2010; Lukhele and Motadi, 2016). For this reason, the doses of CBD that are used in in vitro cellular studies must be carefully determined to ensure they do not cause cytotoxicity.

Example 1: DPPH Antioxidant Assay

The ability of the cannabinoids to act as potential antioxidants was assessed using the 2,2-diphenyl-1-picrylhydrazyl (DPPH) antioxidant assay. The cannabinoids CBDA, CBD, CBDVA, CBDV, CBG, THCV, and the 1:1 CBD:CBDA mixture had the highest antioxidant activities with radical scavenging activities of 38.19%, 48.00%, 43.81%, 44.21%, 44.28%, 45.71%, and 43.74%, respectively.

The 2,2-diphenyl-1-picrylhydrazyl (DPPH) free radical (Alfa Aesar) was prepared at 0.1 mM in ethanol. The cannabinoids were tested at a final concentration of 100 uM. 2 uL of 7.5 mM stock solutions of the cannabinoids to be tested in DMSO were added to 148 uL of 0.1 mM DPPH to achieve a final concentration of 100 µM in the assay. Ascorbic acid (Thermo Scientific) at a final concentration of 10 mg/ml was used as a positive control. The reaction mixture was incubated in the dark at room temperature for 1 hour, the absorbance of the mixture was read at 517 nm using a Spectra Max 5M microplate reader (Molecular Devices, LLC, Sunnyvale, Calif., USA) and the absorbance was converted to percent radical scavenging activity (% RSA) using the following formula: % RSA=[(Absorbance of the control−Absorbance of the sample)/(Absorbance of the control)]×100.

Free radical production occurs when the immune system is activated and antioxidants represent potential effective treatments for inflammatory conditions and autoimmune diseases. Since a couple of recent studies have demonstrated the ability of CBD to act as an antioxidant (Hosseinzadeh et al., 2016; Rajan et al., 2016), the antioxidant potential of all of the major cannabinoids that had been evaluated as immunosuppressants was also investigated. The DPPH antioxidant assay can be used to measure the ability of a compound to scavenge free radicals by measuring the ability of compounds to hydrogenate and reduce DPPH. The DPPH assay was conducted on CBCA, CBDA, CBDVA, CBGA, CBLA, CBNA, THCVA, and their decarboxylated derivatives as well as the 1:1 CBD:CBDA mixture. Results are shown in Table 5.

TABLE 5

Ability of the non-psychotropic cannabinoids CBCA, CBDA, CBDVA, CBGA, CBLA, CBNA, THCVA, and their decarboxylated derivatives, to hydrogenate and reduce DPPH

| Compounds | % RSA (radical scavenging activity) |
|---|---|
| Untreated control | 17.00 |
| Ascorbic acid control | 94.00 |
| CBC | 31.95 |
| CBCA | 19.02 |
| CBD | 48.00 |
| CBDA | 38.19 |
| CBDV | 44.21 |
| CBDVA | 43.81 |
| CBG | 44.28 |
| CBGA | 26.84 |
| CBL | 30.84 |
| CBLA | 21.18 |
| CBN | 33.83 |
| CBNA | 24.92 |
| THCV | 45.71 |
| THCVA | 29.22 |
| 1:1 CBD:CBDA | 43.74 |

CBDA, CBD, CBDVA, CBDV, CBG, THCV, and the 1:1 CBD:CBDA mixture had the highest antioxidant activities with radical scavenging activities of 38.19%, 48.00%, 43.81%, 44.21%, 44.28%, 45.71%, and 43.74%, respectively. Ascorbic acid (10 mg/mL) was used as a positive control, and the ability of compounds to reduce DPPH was calculated as % RSA (radical scavenging activity).

Example 2: THP-1 Human Cellular LPS Cytokine
Assay

One of the most robust in vitro cellular tests that can be performed to evaluate the immunosuppressant potential of a therapeutic agent is to determine whether the agent can suppress the cytokine levels in THP-1 human monocyte cells that have been differentiated into macrophage-like cells using PMA and then had their immune system induced with an immunostimulant, such as LPS (Cochran F R, Finch-Arietta M B, 1989).

The THP-1 cytokine suppression assay was run as three independent experiments and only cytokines whose expression was induced more than two-fold in the LPS control versus the untreated sample were analyzed for suppression by the dexamethasone control and the CBC, CBCA, CBD, CBDA, CBDV, CBDVA, CBG, CBGA, CBL, CBLA, CBN, CBNA, THCV, THCVA cannabinoids, or the 1:1 CBD:CBDA cannabinoid mixture.

THP-1 cells were maintained in RPMI 1640 medium supplemented with 10% heat-inactivated FBS and 1% penicillin/streptomycin (complete culture medium) at 37° C. with 5% CO2 supplemented. Cell concentrations were adjusted to 5×105 cells/mL by centrifugation at 500×g for 5 minutes and resuspended in complete culture medium with 100 nM of phorbol 12-myristate 13-acetate (PMA). Cells were seeded onto 24-, or 12-well plates and incubated for 48 hours to 72 hours to allow for differentiation. Cells were washed with serum-free RPMI 1640 medium before each experiment to remove undifferentiated cells. Differentiated THP-1 cells were treated with cannabinoids, or the corticosteroid dexamethasone as a control, at a final concentration of 2□M for 1 hour and then stimulated with 20 ng/mL of lipopolysaccharide (LPS) for 4 hours. Supernatants were collected for quantification of human cytokine levels to assess the cytokine response. Cells remaining after the supernatant collection were tested to ensure they had at least 90% viability as determined by Alamar Blue assays. To conduct the Alamar Blue assays, supernatants were replaced with culture medium containing 1× Alamar Blue reagent and incubated overnight. Cell viability was assessed by measuring relative fluorescent units (RFU) on the SpectraMax M2e microplate reader (Molecular Devices Inc., Sunnyvale, Calif., USA) at Excitation 560 nm and Emission 590 nm. Controls included untreated cells with DMSO at the same concentration as the treated cells, LPS stimulated cells with DMSO at the same concentration as the treated cells and LPS stimulated cell with the various treatments. The levels of 42 of the most common human cytokines (Eve Technologies, Calgary, Canada Table 6) were determined by multiplex analysis.

TABLE 6

| Human Cytokines | |
| --- | --- |
| Abbreviation | Full name |
| EGF | Epidermal growth factor |
| Eotaxin-1 | Eotaxin-1 |
| FGF-β | Basic fibroblast growth factor |
| Flt-3L | Fibromyalgia syndrome (Fms)-like tyrosine kinase 3 ligand |
| Fractalkine | Fractalkine |
| G-CSF | Granulocyte colony-stimulating factor |
| GM-CSF | Granulocyte macrophage colony stimulating factor |
| GROα | Growth-regulated oncogene-alpha |
| IFNα | Interferon alpha |

TABLE 6-continued

| Human Cytokines | |
| --- | --- |
| Abbreviation | Full name |
| IFNγ | Interferon gamma |
| IL-1α | Interleukin 1 alpha |
| IL-1β | Interleukin 1 beta |
| IL-1RA | interleukin-1 receptor antagonist |
| IL-2 | Interleukin-2 |
| IL-3 | Interleukin-3 |
| IL-4 | Interleukin-4 |
| IL-5 | Interleukin-5 |
| IL-6 | Interleukin-6 |
| IL-7 | Interleukin-7 |
| IL-8 | Interleukin-8 |
| IL-9 | Interleukin-9 |
| IL-10 | Interleukin-10 |
| IL-12β p40 | Interleukin-12 beta subunit p40 |
| IL-12 p70 | Interleukin-12 p70 |
| IL-13 | Interleukin-13 |
| IL-15 | Interleukin-15 |
| IL-17 | Interleukin-17 |
| IL-18 | Interleukin-18 |
| IP-10 | Interferon gamma-induced protein 10 |
| MCP-1 | Monocyte chemoattractant protein-1 |
| MCP-3 | Monocyte chemoattractant protein-3 |
| MDC | Macrophage-derived chemokine |
| MIP-1α | Macrophage inflammatory protein-1 alpha |
| MIP-1β | Macrophage inflammatory protein-1 beta |
| PDGF-AA | Platelet-derived growth factor AA |
| PDGF-AB/BB | Platelet-derived growth factor AB/BB |
| RANTES | Regulated on activation, normal T cell expressed and secreted |
| sCD40L | Soluble CD40-ligand |
| TGF-α | Transforming growth factor alpha |
| TNF-α | Tumor necrosis factor-alpha |
| TNF-β | Tumor necrosis factor-beta |
| VEGF-A | Vascular endothelial growth factor |

The induction of cytokine levels in differentiated THP-1 human monocyte cells induced with LPS and the suppression of cytokine levels by the cannabinoids after LPS induction varied widely depending on the cytokine. For this reason, the level of cytokine suppression was determined for each cytokine by each cannabinoid that was tested and the total averaged suppression for each cannabinoid was determined by dividing the total suppression by the number of the cytokines that were analyzed. Only cytokines whose levels were induced at least two-fold by LPS in the LPS-only control versus the untreated control were considered for this analysis.

All of the cannabinoids were able to suppress cytokine expression, as shown in Table 7.

TABLE 7

| Suppression of cytokine induction in THP-1 by dexamethasone, the CBC, CBCA, CBD, CBDA, CBDV, CBDVA, CBG, CBGA, CBL, CBLA, CBN, CBNA, THCV, THCVA cannabinoids, or the 1:1 CBD:CBDA cannabinoid mixture | |
| --- | --- |
| Cannabinoid | % Cytokine Suppression |
| Dexamethasone (control) | 51.02 |
| CBC | 22.58 |
| CBCA | 34.58 |
| CBD | 33.15 |
| CBDA | 37.18 |
| CBDV | 36.72 |
| CBDVA | 32.37 |
| CBG | 35.84 |
| CBGA | 34.30 |
| CBL | 43.58 |
| CBLA | 34.42 |

TABLE 7-continued

| Suppression of cytokine induction in THP-1 by dexamethasone, the CBC, CBCA, CBD, CBDA, CBDV, CBDVA, CBG, CBGA, CBL, CBLA, CBN, CBNA, THCV, THCVA cannabinoids, or the 1:1 CBD:CBDA cannabinoid mixture | |
|---|---|
| Cannabinoid | % Cytokine Suppression |
| CBN | 37.04 |
| CBNA | 33.99 |
| THCV | 34.75 |
| THCVA | 28.37 |
| 1:1 CBD:CBDA | 45.51 |

The 1:1 CBD:CBDA mixture exhibited the greatest suppression followed by CBL. CBC and THCVA were not as effective at suppressing cytokine expression compared to the other cannabinoids. The suppression by the 1:1 equimolar mixture of CBD:CBDA was 37.28% more effective than CBD and 22.40% more effective than CBDA. The suppression by the 1:1 equimolar mixture of CBD:CBDA was clearly synergistic compared to the suppression by CBD or CBDA alone. The pharmaceutical definition of synergy is that the interaction of two or more agents should produce a combined effect which is greater than the sum of the separate effects of the agents. In this case the effect of a 1:1 CBD:CBDA or ½ CBD and ½ CBDA mixture should be greater than the sum of the individual effects of CBD and CBDA, which are (½×CBD+½×CBDA); i.e., the 45.51% suppression by 1:1 CBD:CBDA was greater than the 35.17% expression expected by ½×CBD+½×CBDA.

Next, the THP-1 cytokine suppression assay was run as four independent experiments and only cytokines whose expression was induced more than two-fold in the LPS control versus the untreated sample in at least three out of the four experiments were analyzed for suppression by the dexamethasone control and the CBD and CBDA cannabinoids or the 1:1 equimolar mixture of the CBD:CBDA cannabinoids. The results are summarized in Table 8.

TABLE 8

| Suppression of cytokine induction in THP-1 by dexamethasone, CBD, CBDA or the 1:1 equimolar mixture of CBD:CBDA | | | |
|---|---|---|---|
| | Percent cytokine suppression by dexamethasone, CBD, CBDA or 1:1 CBD:CBDA | | |
| Cytokines | Dexamethasone | CBD | CBDA | 1:1 CBD: CBDA |
| EGF | 0.74 | −5.61 | 5.34 | 71.26 |
| FGF-β | −18.23 | 41.85 | 30.37 | 58.97 |
| Flt-3L | 57.45 | 60.02 | 47.81 | 43.93 |
| G-CSF | 41.05 | 51.32 | 77.66 | 67.15 |
| GM-CSF | 80.68 | 45.16 | 43.68 | 47.23 |
| IFNγ | 56.19 | 13.71 | 60.44 | 49.19 |
| IL-1α | 77.5 | 55.14 | 44.04 | 54.61 |
| IL-1β | 67.84 | 71.06 | 53.82 | 61.02 |
| IL-4 | 56.32 | 14.63 | 10.49 | 11.38 |
| IL-6 | 90.56 | 66.26 | 69.39 | 69.39 |
| IL-7 | 64.36 | 18.2 | 37.62 | 36.27 |
| IL-10 | 74.07 | 32.42 | 23.20 | 53.96 |
| IL-12 p70 | 1.37 | −31.17 | 8.24 | 32.27 |
| IL-15 | 29.2 | 62.30 | 47.99 | 63.16 |
| IL-18 | −15.38 | 56.90 | 37.34 | 54.34 |
| IP-10 | 64.85 | 67.08 | 73.87 | 64.75 |
| MCP-1 | 83.18 | 43.90 | 54.97 | 54.08 |
| MIP-1β | 73.58 | 31.85 | 47.92 | 35.02 |
| TNFα | 45.33 | 29.05 | 28.56 | 28.11 |

TABLE 8-continued

| Suppression of cytokine induction in THP-1 by dexamethasone, CBD, CBDA or the 1:1 equimolar mixture of CBD:CBDA | | | |
|---|---|---|---|
| | Percent cytokine suppression by dexamethasone, CBD, CBDA or 1:1 CBD:CBDA | | |
| Cytokines | Dexamethasone | CBD | CBDA | 1:1 CBD: CBDA |
| TNFβ | 72.69 | 68.24 | 45.83 | 87.5 |
| Average | 50.17 | 39.62 | 42.43 | 52.18 |

The expression of 20 out of the 42 cytokines that were analyzed was induced more than two-fold in the LPS versus the untreated samples and either dexamethasone or the CBD, CBDA and the 1:1 equimolar mixture of CBD:CBDA cannabinoids suppressed the expression of these cytokines. The IFNγ, IL-1β, IL-2, IL-6, IL-12, IL-15, IL-16, IL-17, IL-18, IL-23 and TNFα cytokines are widely recognized to be inflammatory cytokines and all of them were included in the cytokines that were analyzed except for IL-16 and IL-23. The expression levels of all of these cytokines was induced more than two-fold by LPS with the exception of IL-2 and 11-17. The expression levels of 7 out of the 7, or 100.00%, of the inflammatory cytokines whose expression levels were induced more than two-fold by LPS, could be strongly suppressed by the cannabinoids. The IL-1RA, IL-4, IL-10, IL-11, IL-13 and TGFβ cytokines are widely recognized to be anti-inflammatory cytokines and all of them were included in the cytokines that were analyzed except for IL-11 and TGFβ. The expression levels of only 1 out of the 4, or 25% of the anti-inflammatory cytokines that were analyzed could be induced at least two-fold by LPS and strongly suppressed by the cannabinoids. Thus the cannabinoids preferentially targeted the suppression of inflammatory cytokines as opposed to anti-inflammatory cytokines. It is noteworthy that the suppression of FGF-2, IL-15, IL-18 could only be achieved by the cannabinoids and not dexamethasone and that IL-15 and IL-18 are generally recognized as two of the more important inflammatory cytokines.

The suppression by the 1:1 equimolar mixture of CBD:CBDA was 31.70% more effective than CBD and 22.98% more effective than CBDA and the effectiveness of the suppression by the 1:1 equimolar mixture of CBD:CBDA versus CBD and CBDA was very similar to the results that were achieved in the experiments that compared all of the cannabinoids. The suppression by the 1:1 equimolar mixture of CBD:CBDA was clearly synergistic compared to the suppression by CBD or CBDA alone. The 52.18% suppression by 1:1 CBD:CBDA was greater than the 41.03% expression expected by ½×CBD+½×CBDA.

Example 3: Mouse LPS Cytokine Animal Model

This experiment was conducted to compare the ability of CBD, CBDA or the 1:1 equimolar mixture of CBD:CBDA to suppress the induction of cytokines whose expression levels were induced in mice by LPS. If two out of the three cannabinoids that were evaluated could suppress the levels of cytokines that had been induced at least two-fold by LPS then all three of the cannabinoids that were tested were included in the analysis.

The ability of agents to suppress the immune system can be tested in vivo using an LPS mouse model, in which mice are injected with LPS to cause an immune response (Field et al., 1970; Ghezzi P and Sipe J D, 1988). Similar to the in vitro THP-1 LPS assay, compounds are then analyzed for their ability to suppress the immune response by measuring the cytokine levels.

Four 20 g female C57BL/6 mice were used per group. The experimental mice were first injected with 0.1 mL of the cannabinoids prepared at 1 mg/mL in phosphate buffer (PB) with 5% DMSO to yield a final dose of 5 mg/kg, followed one hour later by the injection of 0.1 mL of 0.02 mg/mL LPS in PB to yield a final dose of 0.1 mg/kg. Mice injected with 0.1 mL of PB with 5% DMSO and 0.1 mL of PBS served as a non-induced control and mice injected with 0.1 mL of PB with 5% DMSO and 0.1 mL of 0.02 mg/mL LPS in PB served as a LPS untreated control. After allowing two hours for the immune system to be induced by LPS, the mice were then euthanized, heart punctures performed to extract the blood, which was allowed to coagulate on ice for 1 hour before centrifuging to isolate the serum. The levels of 32 of the most common mouse cytokines (Eve Technologies, Calgary, Canada, Table 9) were determined by multi-plex analysis.

TABLE 9

| Mouse Cytokines | |
| --- | --- |
| Abbreviation | Full name |
| Eotaxin-1 | Eotaxin-1 |
| G-CSF | Granulocyte colony-stimulating factor |
| GM-CSF | Granulocyte macrophage colony stimulating factor |
| IFNγ | Interferon gamma |
| IL-1α | Interleukin 1 alpha |
| IL-1β | Interleukin 1 beta |
| IL-2 | Interleukin-2 |
| IL-3 | Interleukin-3 (IL-3) |
| IL-4 | Interleukin-4 (IL-4) |
| IL-5 | Interleukin-5 (IL-5) |
| IL-6 | Interleukin-6 (IL-6) |
| IL-7 | Interleukin-7 (IL-7) |
| IL-9 | Interleukin-9 (IL-9) |
| IL-10 | Interleukin-10 (IL-10) |
| IL-12β p40 | Interleukin-12 subunit p40 |
| IL-12 p70 | Interleukin-12 p70 |
| IL-13 | Interleukin-13 |
| IL-15 | Interleukin-15 (IL-15) |
| IL-17 | Interleukin-17 |
| IP-10 | Interferon gamma-induced protein 10 |
| KC | Keratinocyte chemoattractant |
| LIF | Leukemia inhibitory factor |
| LIX | C-X-C motif chemokine 5 |
| MCP-1 | Monocyte chemoattractant protein-1 |
| M-CSF | Macrophage colony- stimulating factor |
| MIG | Monokine induced by gamma interferon |
| MIP-1α | Macrophage inflammatory protein-1 alpha |
| MIP-1β | Macrophage inflammatory protein-1 beta |
| MIP-2 | Macrophage inflammatory protein-2 |
| RANTES | Regulated on activation, normal T cell expressed and secreted |
| TNF-α | Tumor necrosis factor-alpha |
| VEGF-A | Vascular endothelial growth factor |

The induction of cytokine levels in C57BL/6 mice induced with LPS and the suppression of cytokine levels by the cannabinoids after LPS induction varied widely depending on the cytokine. For this reason, the level of cytokine suppression was determined for each cytokine by each cannabinoid that was tested and the total averaged suppression for each cannabinoid was determined by dividing the total suppression by the number of the cytokines that were analyzed. Because the purpose of this experiment was to compare the effectiveness of CBD, CBDA or the 1:1 CBD: CBDA mixture at suppressing cytokine levels, only cytokines whose levels were induced at least two-fold by LPS in the LPS-only control versus the untreated control and could be suppressed by at least two of the cannabinoids were considered for this analysis. The results are summarized in Table 10.

TABLE 10

| Percent suppression of mouse cytokine induction in mice by CBD, CBDA or a 1:1 equimolar mixture of CBD:CBDA | | | |
| --- | --- | --- | --- |
| | Percent suppression by CBD, CBDA or 1:1 CBD:CBDA | | |
| Cytokines | CBD | CBDA | 1:1 CBD: CBDA |
| GM-CSF | 34.53 | 27.86 | 2.08 |
| IFNγ | −0.19 | 31.60 | 33.46 |
| IL-1β | 10.58 | 11.89 | 8.59 |
| IL-2 | −0.09 | 7.82 | 8.34 |
| IL-6 | 4.49 | 6.09 | 12.61 |
| IL-12β p40 | 34.89 | 58.93 | 27.98 |
| IL-13 | 6.38 | 4.16 | −10.80 |
| IL-17 | 7.51 | 7.86 | 17.67 |
| IP-10 | 1.72 | 4.58 | 5.82 |
| KC | 7.85 | 18.15 | 10.16 |
| LIF | 25.24 | 28.12 | 34.12 |
| M-CSF | 7.70 | −51.56 | 47.81 |
| MIP-1α | 6.69 | 14.86 | 41.97 |
| MIP-1β | −0.77 | 9.12 | 21.39 |
| MIP-2 | 34.56 | 20.19 | 29.65 |
| TNF-α | 24.74 | 19.69 | 44.53 |
| Average | 12.86 | 13.71 | 20.96 |

At least two out of the three cannabinoids that were tested, CBD, CBDA or the 1:1 equimolar mixture of CBD:CBDA, suppressed the expression of 16 out of the 23 cytokines that were induced more than two-fold in the LPS versus the untreated samples. The IFNγ, IL-1β, IL-2, IL-6, IL-12, IL-15, IL-16, IL-17, IL-18, IL-23 and TNFα cytokines are widely recognized to be inflammatory cytokines and all of them were included in the cytokines that were analyzed except for IL-16, IL-18 and IL-23. The expression levels of 7 out of the 8, or 87.50%, of the inflammatory cytokines that were analyzed could be suppressed by the cannabinoids. The IL-1RA, IL-4, IL-10, IL-11, IL-13 and TGFβ cytokines are widely recognized to be anti-inflammatory cytokines and all of them were included in the cytokines that were analyzed except for IL-1RA, IL-11 and TGFβ. The expression levels of only 1 out of the 3, or 33.33% of the anti-inflammatory cytokines that were analyzed could be induced at least two-fold by LPS and strongly suppressed by the cannabinoids. Thus the cannabinoids preferentially targeted the suppression of inflammatory cytokines as opposed to anti-inflammatory cytokines. The suppression by the 1:1 equimolar mixture of CBD:CBDA was clearly synergistic compared to the suppression by CBD or CBDA alone. The 20.96% suppression by 1:1 CBD:CBDA was greater than the 13.29% expression expected by ½×CBD+½×CBDA.

Example 4: Human Cellular U-937 Autophagy Induction Assay

The induction of autophagy was monitored using anti-LC3 antibodies to detect LC3 on the autophagosome in human U-937 pro-monocytic histiocytic lymphoma cells (ATCC, Manassas, Va., USA), which generate morphologies characteristic of macrophages upon induction by various stimuli. U-937 cells were cultured in RPMI-1640 medium with L-glutamine and sodium bicarbonate (Sigma-Aldrich, St Louis, Mo.) supplemented with 10% fetal bovine serum (FBS) and 1% penicillin in 25 cm2 tissue flasks at 37° C. in a 5% CO2 humidified atmosphere and passaged every 2-3 days. U-937 cells were seeded in 96 well plates at 5×105 cells/mL and stimulated with 100 ng/mL PMA to induce differentiation for 24 hours. The cells were then treated with the various cannabinoids at 1.0 µM concentrations for 12 hours. 30 µM chloroquine was used as a positive control. After treatment, the cells were fixed using 3.7% formaldehyde in PBS for 15 minutes at room temperature and washed with PBS to remove the fixative. Permeabilization reagent (0.2% Triton X-100 in PBS) (Sigma-Aldrich) was added, the cells were incubated for 15 minutes at room temperature and then the cells were washed with PBS to remove the permeabilization reagent. LC3B rabbit polyclonal antibody (Invitrogen) was added at a final concentration of 0.5 µg/ml for 1 hour at room temperature and the cells were washed with PBS remove the primary antibody. Secondary conjugated goat anti-rabbit polyclonal antibody (Thermo Scientific) was then added at a final concentration of 2.0 µg/ml for 1 hour at room temperature. The cells were washed, Hoechst dye was added to stain the nucleus and the cells were imaged using an Arrayscan VTI high-content screening (HCS) reader (Thermo Scientific) with the appropriate filters and the data was analyzed using the vHCS Scan software.

Autophagy, or autophagocytosis, is a complex lysosomal based process that degrades and recycles proteins and cellular components. It has become increasingly evident that autophagy is involved in regulating the immune system (Kuballa et al., 2012) and that autophagy is dysfunctional and downregulated in autoimmune diseases (Wang and Muller, 2015; Wang et al., 2017). Autophagy has been proposed as a potential treatment for inflammatory conditions and autoimmune diseases (Nguyen et al., 2013) and as therapeutics for the treatment of cancer (Mukhtar, et al., 2012; Byun et al., 2017; Jiang et al., 2019).

Results are shown in Table 11. While most of the cannabinoids did not induce autophagy, CBL, CBLA, THCVA and the 1:1 equimolar mixture of CBD:CBDA did. At a concentration of 1.0 µM, CBL, CBLA, THCVA and the 1:1 equimolar mixture of CBD:CBDA increased autophagy 59.30%, 49.78%, 37.72%, and 40.37%, respectively, compared to the untreated control. Chloroquine at a concentration of 30 µM was included as a positive control. The ability to induce autophagy was determined as a percentage with respect to the untreated control.

TABLE 11

Induction of autophagy

| Compounds | Fluorescence | Induction |
|---|---|---|
| Untreated | 48.25 | |
| Chloroquine (30 uM) | 111.20 | |
| CBC | 47.84 | −0.85% |
| CBCA | 42.61 | −11.69% |
| CBD | 45.43 | −5.84% |
| CBDA | 37.64 | −21.99% |
| CBDV | 38.19 | −20.85% |
| CBDVA | 39.29 | −18.57% |
| CBG | 37.35 | −22.59% |
| CBGA | 37.47 | −22.34% |
| CBL | 76.86 | +59.30% |
| CBLA | 72.27 | +49.78% |
| CBN | 40.80 | −15.44% |
| CBNA | 36.89 | −23.54% |
| THCV | 42.14 | −12.66% |
| THCVA | 66.45 | +37.72% |
| 1:1 CBD:CBDA | 67.73 | +40.37% |

42

Discussion

Examples 1 to 4 demonstrate the ability of the major non-psychotropic Cannabis cannabinoids to act as anti-inflammatory agents, immunosuppressants and/or antioxidants, as summarized in Table 12. While all of the tested cannabinoids demonstrated at least some ability to suppress cytokine induction, CBCA, CBDA, CBD, CBDVA, CBDV, CBGA, CBG, CBLA, CBL, CBNA, CBN, THCVA, THCV, and the 1:1 equimolar mixture of CBD:CBDA demonstrated the strongest cytokine suppression in these studies. The individual cannabinoids CBDA, CBD, CBDVA, CBDV, CBG, THCV, and a 1:1 equimolar mixture of CBD:CBDA induced radical scavenging activity by at least two-fold compared to the untreated control. The individual cannabinoids CBCA, CBD, CBDA, CBDV, CBDVA, CBG, CBGA, CBLA, CBL, CBNA, CBN, THCVA, THCV, and a 1:1 equimolar mixture of CBD:CBDA were at least half as effective as dexamethasone at reducing elevated cytokine levels in differentiated THP-1 cells that had been treated with LPS. The individual cannabinoids CBL, CBLA, THCVA, and a 1:1 equimolar mixture of CBD:CBDA proved to be particularly effective at inducing autophagy in differentiated U937 cells.

TABLE 12

Summary of Results

| Compounds | % RSA activity | % Cytokine Suppression | % Autophagy Induction |
|---|---|---|---|
| CBC | 31.95 | 22.58 | −0.85% |
| CBCA | 19.02 | 34.58 | −11.69% |
| CBD | 48.00 | 33.15 | −5.84% |
| CBDA | 38.19 | 37.18 | −21.99% |
| CBDV | 44.21 | 36.72 | −20.85% |
| CBDVA | 43.81 | 32.37 | −18.57% |
| CBG | 44.28 | 35.84 | −22.59% |
| CBGA | 26.84 | 34.30 | −22.34% |
| CBL | 30.84 | 43.58 | +59.30% |
| CBLA | 21.18 | 34.42 | +49.78% |
| CBN | 33.83 | 37.04 | −15.44% |
| CBNA | 24.92 | 33.99 | −23.54% |
| THCV | 45.71 | 34.75 | −12.66% |
| THCVA | 29.22 | 28.37 | +37.72% |
| 1:1 CBD:CBDA | 43.74 | 45.51 | +40.37% |

Example 5

Exemplary cannabinoid profiles of buds from a harvested and dried hemp Cherry variety, a typical hemp strain with a high CBDA content (Table 13) and Cherry Whine, a typical hemp strain with a high CBDA content (Table 15) were analyzed by Pixis Labs, Portland, Oreg., from hemp flowers sold by Tweedle Farms, Portland, Oreg.

TABLE 13

Cannabinoid profile of Cherry variety of hemp

| Cannabinoid | % by mass |
|---|---|
| CBC | 0.125 |
| CBCA | 1.170 |
| CBD | 0.998 |
| CBDA | 19.500 |
| CBDV | 0.000 |
| CBDVA | 0.091 |
| CBG | 0.080 |

TABLE 13-continued

| Cannabinoid profile of Cherry variety of hemp | |
| --- | --- |
| Cannabinoid | % by mass |
| CBGA | 0.328 |
| D8-THC | 0.000 |
| D9-THC | 0.127 |
| THCA | 0.652 |

TABLE 14

| Cannabinoid profile of Cherry Whine variety of hemp | |
| --- | --- |
| Cannabinoid | % by mass |
| CBC | 0.238 |
| CBCA | 0.561 |
| CBD | 3.02 |
| CBDA | 12.100 |
| CBDV | 0.000 |
| CBDVA | 0.052 |
| CBG | 0.141 |
| CBGA | 0.401 |
| A8-THC | 0.000 |
| A9-THC | 0.247 |
| THCA | 0.186 |

Example 6: Performing the Mouse LPS Cytokine Animal Model to Evaluate the Combination of 1:1 CBD:CBDA with Omega Fatty Acids A series of experiments using a mouse LPS cytokine animal model were performed. In the mouse LPS cytokine animal model, mice were injected with LPS, which induced the immune response shortly after the mice were injected with one of the potential anti-inflammatory compounds under evaluation (the "test compound"). The efficacy of the test compound was evaluated based on its ability to reduce expression levels of inflammatory cytokines that were elevated due to the immune response. The test compounds included a cannabinoid, an omega fatty acid, and a cannabinoid-omega fatty acid composition.

The mice were intraperitoneally injected with 0.1 mL of the test compound. One hour later, the mice were intraperitoneally injected with 0.1 mL of LPS in phosphate buffered saline (PBS). Four hours later, a heart puncture was performed and the blood was allowed to clot to generate serum. 0.1 mL of the serum was diluted 1:2 with PBS and stored at −80° C. The serum was then sent to a laboratory where a mouse cytokine array/chemokine array 31-plex (MD31) analysis was performed that analyzed the expression levels of the 32 cytokines/chemokines listed in Table 9, above.

Only inflammatory cytokines whose expression level were induced two fold or greater by LPS were considered in the analysis to determine the effectiveness of the test compounds to reduce or suppress inflammation. For each considered test compound, the ability of the test compound to suppress each inflammatory cytokine was calculated by determining the percent suppression. Then, the average suppression of the test compound was determined by adding the individual suppression values of the test compound for each cytokine and dividing by the total number of cytokines that were induced two fold or greater by LPS.

The dosing of therapeutics in animals to achieve the same efficacies that are observed in humans based on known human doses often have to be adjusted due to the large differences in drug metabolism between animals and humans. The required dose in mice based on the known human dose can be 12.3 times higher (Shin et al., 2010; Nair and Jacob, 2016).

Example 6A: Determining the Dosing Efficacy of a Cannabinoid in Mice Using the Mouse LPS Cytokine Animal Model CBD has been tested in numerous mice studies and the preferred vehicle for injection is propylene glycol (PG), which poses a significantly lower toxicological risk than dimethyl sulfoxide (DMSO). CBD that has been resuspended in propylene glycol is missed with PBS for injection. In rats, the LD50 of propylene glycol is 20,000 mg/kg while the LD50 of dimethyl sulfoxide is 14,500 mg/kg.

A typical dose of CBD in human adults that is used in the US is 25 to 50 mg and is based on the currently accepted 181 lb. or 82.1 kg average weight value for human adults in the US. This is equivalent to 0.30 to 0.60 mg/kg for a 20 g mouse. Thus, in mice, the most efficacious dose may range from 0.30 to 7.38 mg/kg depending on how CBD is metabolized in mice versus humans. Initially, a study of doses of 10 mg/kg, 3 mg/kg, and 1 mg/kg of 1:1 CBD:CBDA in mice was performed using propylene glycol as the vehicle (Study 1, below). Based on the results from this initial study, a second study (Study 2, below) was performed with doses of 1 mg/kg, 0.5 mg/kg, and 0.25 mg/kg of 1:1 CBD:CBDA using propylene glycol as the vehicle to determine the most efficacious dose of 1:1 CBD:CBDA in mice. Because the goal was to examine the effects of combining 1:1 CBD:CBDA with omega fatty acids, a third study (Study 3, below) was performed to verify the effectiveness of 1:1 CBD:CBDA when MCT oil was used as the vehicle since mice experiments with omega fatty acids have to use MCT oil as the vehicle. The third study was performed with doses of 5 mg/kg, 1.67 mg/kg, 0.5 mg/kg, 0.167 mg/kg, and 0.05 mg/kg of 1:1 CBD:CBDA using MCT oil as the vehicle to determine the most efficacious dose of 1:1 CBD:CBDA in mice.

Study 1: 10 mg/kg, 3 mg/kg, and 1 mg/kg of 1:1 CBD:CBDA Resuspended in 90% PBS, 10% Propylene Glycol 20 female C57BL/6 mice that weighed approximately 20 g each were allowed to acclimate for one week with unlimited access to food and water. On the day of the study, the mice were weighed and split into five groups of four mice each so the average weight of each group was as close as possible to each other. The five groups were (1) Untreated (0.1 mL injection of 90% PBS, 10% propylene glycol, followed 1 hour later by a 0.1 mL injection of PBS instead of LPS); (2) LPS control (0.1 mL injection of 90% PBS, 10% propylene glycol, followed 1 hour later by a 0.1 mL injection of LPS in PBS); (3) 10 mg/kg 1:1 CBD:CBDA treatment group (0.1 mL injection of 1:1 CBD:CBDA in 90% PBS, 10% propylene glycol, followed 1 hour later by a 0.1 mL injection of LPS in PBS); (4) 3 mg/kg 1:1 CBD:CBDA treatment group (0.1 mL injection of 1:1 CBD:CBDA in 90% PBS, 10% propylene glycol, followed 1 hour later by a 0.1 mL injection of LPS in PBS); and (5) 1 mg/kg 1:1 CBD:CBDA treatment group (0.1 mL injection of 1:1 CBD:CBDA in 90% PBS, 10% propylene glycol, followed 1 hour later by a 0.1 mL injection of LPS in PBS).

The 1:1 CBD:CBDA test compounds were dosed at 10.0 mg/kg or 0.2 mg per 20 g mouse, 3.33 mg/kg or 0.067 mg per 20 g mouse and 1.0 mg/kg or 0.02 mg per 20 g mouse. The test compounds were prepared as 20 mg/mL, 6.67 mg/mL and 2 mg/mL solutions in propylene glycol and then diluted 1:10 with phosphate buffered saline (PBS) and mixed well to create a 2 mg/mL, 0.67 mg/mL and 0.2 mg/mL emulsion for a 0.1 mL injection. The LPS was dosed at 0.1 mg/kg or 0.002 mg per 20 g mouse. The LPS was prepared as a 0.02 mg/mL solution in PBS for a 0.1 mL injection. The results of Study 1 are shown in Table 15.

TABLE 15

Percent suppression of elevated cytokine levels by different doses of 1:1 CBD:CBDA

| Cytokine | 10 mg/kg | 3.33 mg/kg | 1.0 mg/kg |
|---|---|---|---|
| GM-CSF | 32.74 | 24.28 | 45.56 |
| IFNγ | −25.96 | 2.92 | 28.03 |
| IL-1α | −47.78 | −26.75 | 10.63 |
| IL-1β | 6.48 | −10.07 | 43.64 |
| IL-2 | 16.42 | 36.22 | 27.10 |
| IL-4 | −6.25 | −100.00 | 31.25 |
| IL-6 | −69.31 | −8.79 | 44.70 |
| IL-7 | 19.78 | 64.20 | 66.63 |
| IL-10 | −89.32 | −60.35 | −39.06 |
| IL-12β p40 | −44.71 | −12.62 | 12.19 |
| IL-17 | 4.12 | 8.70 | 26.11 |
| IP-10 | −80.70 | −40.80 | 13.28 |
| KC | −4.66 | 12.04 | 35.42 |
| LIF | −53.94 | −9.45 | 31.89 |
| MCP-1 | −31.93 | −20.28 | 2.51 |
| M-CSF | 59.20 | 45.92 | 58.51 |
| MIG | −2.39 | −1.35 | 25.06 |
| MIP-1α | −100.00 | −100.00 | −43.27 |
| MIP-1β | −100.00 | −28.14 | −3.18 |
| MIP-2 | 22.09 | 31.93 | 20.10 |
| RANTES | −100.00 | −41.15 | −38.67 |
| TNF-α | −65.33 | −46.52 | 17.98 |
| AVERAGE SUPPRESSION | −30.07 | −12.73 | 18.93 |

22 out of the 32 analyzed cytokines were induced two-fold by LPS. Of the 22 cytokines whose expression level was induced two-fold or greater by LPS, the levels of 18 of these cytokines were suppressed or reduced by at least one of the doses of 1:1 CBD:CBDA that were used in Study 1. Because the greatest efficacy was achieved by the lowest dose of 1:1 CBD:CBDA, the study was repeated with lower doses of 1:1 CBD:CBDA in order to determine the optimal dose of 1:1 CBD:CBDA to suppress inflammation in the mouse LPS cytokine animal model. This repeated study with the lower doses is described below in Study 2.

Study 2: 1 mg/kg, 0.5 mg/kg, and 0.25 mg/kg of 1:1 CBD:CBDA Resuspended in 90% PBS, 10% Propylene Glycol 20 female C57BL/6 mice that weighed approximately 20 g each were allowed to acclimate for one week with unlimited access to food and water. On the day of the study, the mice were weighed and split into five groups of four mice each so that the average weight of each group was as close as possible to each other. The five groups were: (1) Untreated (0.1 mL injection of 90% PBS, 10% propylene glycol, followed 1 hour later by a 0.1 mL injection of PBS instead of LPS); (2) LPS control (0.1 mL injection of 90% PBS, 10% propylene glycol, followed 1 hour later by a 0.1 mL injection of LPS in PBS); (3) 1 mg/kg 1:1 CBD:CBDA treatment group (0.1 mL injection of 1:1 CBD:CBDA in 90% PBS, 10% propylene glycol, followed 1 hour later by a 0.1 mL injection of LPS in PBS); (4) 0.5 mg/kg 1:1 CBD:CBDA treatment group (0.1 mL injection of 1:1 CBD:CBDA in 90% PBS, 10% propylene glycol, followed 1 hour later by a 0.1 mL injection of LPS in PBS); and (5) 0.25 mg/kg 1:1 CBD:CBDA treatment group (0.1 mL injection of 1:1 CBD:CBDA in 90% PBS, 10% propylene glycol, followed 1 hour later by a 0.1 mL injection of LPS in PBS).

The 1:1 CBD:CBDA test compounds were dosed at 1.0 mg/kg or 0.02 mg per 20 g mouse, 0.5 mg/kg or 0.01 mg per 20 g mouse and 0.25 mg/kg or 0.005 mg per 20 g mouse. The test compounds were prepared as 2 mg/mL, 1 mg/mL and 0.5 mg/mL solutions in propylene glycol and then diluted 1:10 with phosphate buffered saline (PBS) and mixed well to create a 0.2 mg/mL, 0.1 mg/mL and 0.05 mg/mL emulsion for a 0.1 mL injection. The LPS was dosed at 0.1 mg/kg or 0.002 mg per 20 g mouse. The LPS was prepared as a 0.02 mg/mL solution in PBS for a 0.1 mL injection. The results of Study 2 are shown below in Table 16.

TABLE 16

Percent suppression of elevated cytokine levels by different doses of 1:1 CBD:CBDA

| Cytokine | 1 mg/kg | 0.5 mg/kg | 0.25 mg/kg |
|---|---|---|---|
| G-CSF | −6.37 | −0.95 | −4.88 |
| GM-CSF | 1.4 | 53.62 | 81.52 |
| IFNγ | 51.31 | 56.09 | 50.42 |
| IL-1β | 35.71 | 27.74 | 29.66 |
| IL-2 | 37.78 | 61.33 | 67.61 |
| IL-6 | −47.20 | 9.95 | 17.99 |
| IL-7 | 77.07 | 43.18 | 85.65 |
| IL-10 | −0.33 | −1.24 | 15.01 |
| IL-12β p40 | 21.17 | 38.29 | 37.21 |
| IL-13 | −46.76 | 10.85 | 14.40 |
| IL-15 | 19.05 | 55.94 | 39.50 |
| IL-17 | 25.29 | 38.45 | 41.37 |
| IP-10 | 56.70 | 70.27 | 68.43 |
| KC | 33.76 | 67.32 | 58.02 |
| LIF | 65.42 | 22.77 | 81.27 |
| MCP-1 | 36.54 | 17.89 | −60.20 |
| M-CSF | 42.86 | 67.28 | 63.93 |
| MIG | 7.65 | 21.98 | −18.87 |
| MIP-1α | −38.89 | −15.73 | −1.95 |
| MIP-1β | −91.05 | −13.60 | −10.32 |
| MIP-2 | 62.13 | 41.78 | 41.74 |
| RANTES | −8.27 | 5.66 | −21.25 |
| TNF-α | −5.81 | 6.07 | −10.33 |
| AVERAGE SUPPRESSION | 14.31 | 29.78 | 28.95 |

23 out of the 32 analyzed cytokines were induced two-fold by LPS. Of the 23 cytokines whose expression level was induced two-fold or greater by LPS, the levels of 20 of these cytokines were suppressed or reduced by at least one of the doses of 1:1 CBD:CBDA that were used in the study. Based on this study, the optimal dose of 1:1 CBD:CBDA was 0.5 mg/kg.

Study 3: 5 mg/kg, 1.67 mg/kg, 0.5 mg/kg, 0.167 mg/kg and 0.05 mg/kg 1:1 CBD:CBDA Resuspended in MCT Oil 32 female C57BL/6 mice that weighed approximately 20 g each were allowed to acclimate for one week with unlimited access to food and water. On the day of the study, the mice were weighed and split into eight groups of four mice each so that the average weight of each group was as close as possible to each other. The eight groups were: (1) Untreated (0.1 mL injection of MCT oil, followed 1 hour later by a 0.1 mL injection of PBS instead of LPS); (2) LPS control (0.1 mL injection of MCT oil, followed 1 hour later by a 0.1 mL injection of LPS in PBS); (3) 0.5 mg/kg dexamethasone treatment group (0.1 mL injection of dexamethasone in MCT oil, followed 1 hour later by a 0.1 mL injection of LPS in PBS); (4) 0.05 mg/kg CBD:CBDA treatment group (0.1 mL injection of 1:1 CBD:CBDA in MCT oil, followed 1 hour later by a 0.1 mL injection of LPS in PBS); (5) 0.167 mg/kg CBD:CBDA treatment group (0.1 mL injection of 1:1 CBD:CBDA in MCT oil, followed 1 hour later by a 0.1 mL injection of LPS in PBS); (6) 0.5 mg/kg CBD:CBDA treatment group (0.1 mL injection of 1:1 CBD:CBDA in MCT oil, followed 1 hour later by a 0.1 mL injection of LPS in PBS); (7) 1.67 mg/kg CBD:CBDA treatment group (0.1 mL injection of 1:1 CBD:CBDA in MCT oil, followed 1 hour later by a 0.1 mL injection of LPS in PBS); and (8) 5.0 mg/kg CBD:CBDA treatment group (0.1 mL injection of 1:1 CBD:CBDA in MCT oil followed 1 hour later by a 0.1 mL injection of LPS in PBS)

The 1:1 CBD:CBDA test compounds were dosed at 5 mg/kg or 0.1 mg per 20 g mouse, 1.67 mg/kg or 0.033 mg per 20 g mouse, 0.5 mg/kg or 0.01 mg per 20 g mouse, 0.167 mg/kg or 0.0033 mg per 20 g mouse and 0.05 mg/kg or 0.001 mg per 20 g mouse. The test compounds were prepared as 1 mg/mL, 0.33 mg/mL, 0.1 mg/mL, 0.033 mg/mL and 0.01 mg/mL solutions in MCT oil for a 0.1 mL injection. The dexamethasone control was dosed at 0.5 mg/kg or 0.01 mg per 20 g mouse. The LPS was dosed at 0.1 mg/kg or 0.002 mg per 20 g mouse. The LPS was prepared as a 0.02 mg/mL solution in PBS for a 0.1 mL injection. The results of Study 3 are shown below in Table 17.

the vehicle can dramatically affect the abilities of pharmaceutical agents, but this was not the case.

Example 6B: Determining the Dosing Efficacy of Omega Fatty Acids in Mice Using the Mouse LPS Cytokine Animal Model In humans, the minimal dose of fish oil omega-3 that most health organizations recommend is 250 to 500 mg per day. Most people use two or three times this amount, i.e., 500 to 1,500 mg of omega-3 fatty acids per day. As previously discussed, since adult humans have an average weight of 82.1 kg and mice can require a dose of up to 12.3 times more of a pharmaceutical agent to observe the same effect as seen in humans due to metabolic differences, the most efficacious dose of omega-3 fatty acids in a 20 g mouse could range from 6.09 to 224.73 mg/kg depending on how the omega-3 fatty acid is metabolized in mice versus humans.

As previously discussed, a number of anti-inflammatory omega-3, -7, and -9 fatty acids can be isolated from fish oil and numerous commercial fish oil products. In this Example 6B, pollock oil that contained a total omega fatty acid

TABLE 17

Percent suppression of elevated cytokine levels by different doses of 1:1 CBD:CBDA

|  | 0.5 mg/kg | 1:1 CBD:CBDA | | | | |
|---|---|---|---|---|---|---|
| Cytokine | DXM | 5.0 mg/kg | 1.67 mg/kg | 0.5 mg/kg | 0.167 mg/kg | 0.05 mg/kg |
| Eotaxin | 55.51 | 34.92 | 29.19 | 43.70 | 58.86 | 18.64 |
| G-CSF | 3.88 | −4.74 | 0.34 | 7.96 | −5.57 | −0.70 |
| GM-CSF | 21.21 | 41.96 | 40.80 | 42.85 | 47.64 | 29.62 |
| IFNγ | 14.14 | 53.29 | 6.23 | −14.28 | 62.49 | 26.31 |
| IL-1β | 61.12 | 47.01 | 59.18 | 39.08 | 35.10 | 27.70 |
| IL-2 | −15.63 | 40.53 | 33.70 | 55.15 | 52.82 | 17.25 |
| IL-6 | 78.65 | 76.60 | 19.91 | 49.51 | 65.53 | −75.92 |
| IL-7 | 12.53 | −100.00 | 42.51 | 52.77 | 64.89 | 19.92 |
| IL-9 | 5.23 | 48.93 | 53.84 | 56.47 | 66.72 | 45.43 |
| IL-10 | 46.83 | 24.77 | 45.79 | 56.05 | 28.70 | −32.77 |
| IL-12β p40 | 29.69 | 47.44 | 40.87 | 36.53 | 49.41 | 38.39 |
| IL-12 p70 | −46.46 | 49.58 | 25.30 | 6.42 | 22.03 | −10.11 |
| IL-13 | 21.00 | 24.80 | 16.33 | 28.00 | 35.88 | 12.26 |
| IL-17 | 53.81 | 33.99 | −58.08 | −5.01 | 43.90 | −12.62 |
| IP-10 | 38.48 | −19.16 | 21.41 | 44.63 | 33.25 | −16.74 |
| KC | 86.96 | 64.16 | 69.31 | 71.92 | 58.67 | 23.47 |
| LIF | 35.14 | 37.96 | 38.39 | 19.74 | 40.13 | 7.59 |
| MCP-1 | 69.72 | 41.37 | 22.75 | 52.48 | 51.02 | −7.54 |
| M-CSF | 18.55 | −31.86 | 10.74 | 9.71 | 12.59 | −100.00 |
| MIG | 37.08 | 15.23 | 19.79 | 25.01 | 24.98 | 8.85 |
| MIP-1α | 48.38 | 47.06 | 39.09 | 49.37 | 38.76 | 15.48 |
| MIP-1β | 32.24 | 26.49 | 34.98 | 22.61 | 13.92 | −31.29 |
| MIP-2 | 41.28 | 40.29 | 53.01 | 39.95 | 46.65 | 17.99 |
| RANTES | 32.46 | 9.16 | 13.11 | 40.86 | 27.63 | −12.57 |
| TNF-α | 53.09 | 27.18 | 38.61 | 38.33 | 26.70 | 18.10 |
| VEGF | 66.07 | 44.35 | 15.76 | 17.15 | 58.32 | 31.89 |
| AVERAGE SUPPRESSION | 34.65 | 27.74 | 28.19 | 34.11 | 40.81 | 2.26 |

26 out of the 32 analyzed cytokines were induced two-fold by LPS. Of the 26 cytokines whose expression level was induced two-fold or greater by LPS, the levels of all 26 of these cytokines were suppressed or reduced by at least one of the doses of 1:1 CBD:CBDA that were used in the study. The ability of dexamethasone, abbreviated DXM in the table, to suppress the elevated cytokine levels, similarly to 1:1 CBD:CBDA, indicated that the study worked. There was excellent agreement between this Study 3 and Study 2. The optimal dose of 1:1 CBD:CBDA ranged from 0.167 mg/kg to 0.5 mg/kg, and the vehicle that 1:1 CBD:CBDA was resuspended in did not affect the outcome. Sometimes concentration of 456 mg/mL with total omega-3 fatty acids at 209 mg/mL, total omega-7 fatty acids at 85 mg/mL and total omega-9 fatty acids at 144 mg/mL was used.

Study 1: 625 mg/kg, 187.5 Mg/Kg, 62.5 Mg/Kg, 18.75 mg/kg, and 6.25 mg/kg of Omega Fatty Acids 28 female C57BL/6 mice that weighed approximately 20 g each were allowed to acclimate for one week with unlimited access to food and water. On the day of the study, the mice were weighed and split into seven groups of four mice each so that the average weight of each group was as close as possible to each other. The seven groups included: (1) Untreated (0.1 mL injection of MCT oil, followed 1 hour later by a 0.1 mL injection of PBS instead of LPS); (2) LPS control (0.1 mL injection of MCT oil, followed 1 hour later by a 0.1 mL injection of LPS in PBS); (3) 625 mg/kg omega fatty acid treatment groups (0.1 mL injection of omega fatty acids in MCT oil, followed 1 hour later by a 0.1 mL injection of LPS in PBS; (4) 187.5 mg/kg omega fatty acid treatment groups (0.1 mL injection of omega fatty acids in MCT oil, followed 1 hour later by a 0.1 mL injection of LPS in PBS; (5) 62.5 mg/kg omega fatty acid treatment groups (0.1 mL injection of omega fatty acids in MCT oil, followed 1 hour later by a 0.1 mL injection of LPS in PBS; (6) 18.75 mg/kg omega fatty acid treatment groups (0.1 mL injection of omega fatty acids in MCT oil, followed 1 hour later by a 0.1 mL injection of LPS in PBS; and (7) 6.25 mg/kg omega fatty acid treatment groups (0.1 mL injection of omega fatty acids in MCT oil, followed 1 hour later by a 0.1 mL injection of LPS in PBS).

The omega fatty acids were dosed at 625.0 mg/kg or 12.5 mg per 20 g mouse, 187.5 mg/kg or 3.75 mg per 20 g mouse, 62.5.0 mg/kg or 1.25 mg per 20 g mouse, 18.75 mg/kg or 0.375 mg per 20 g mouse and 6.25 mg/kg or 0.125 mg per 20 g mouse. The omega fatty acids were diluted with MCT oil to create 125.00 mg/mL, 37.5 mg/mL, 12.5 mg/mL, 3.75 mg/mL and 1.25 mg/mL solutions for the 0.1 mL injections. The LPS was dosed at 0.1 mg/kg or 0.002 mg per 20 g mouse. The LPS was prepared as a 0.02 mg/mL solution in PBS for a 0.1 mL injection. The results of Study 1 appear in Table 18, below.

TABLE 18

| Percent suppression of elevated cytokine levels by different doses of omega fatty acids | | | | |
| --- | --- | --- | --- | --- |
| Cytokines | 625 mg/kg | 187.5 mg/kg | 62.5 mg/kg | 18.75 mg/kg | 6.25 mg/kg |
| G-CSF | 1.56 | −0.06 | 6.26 | 22.62 | −1.63 |
| GM-CSF | 12.58 | 28.92 | 3.48 | 19.35 | −8.62 |
| IFNγ | −2.78 | −20.28 | −8.13 | −86.86 | −100.00 |
| IL-1β | −14.14 | 12.26 | 10.81 | 14.24 | −19.30 |
| IL-3 | −100.00 | 41.00 | −100.00 | −3.50 | 16.00 |
| IL-6 | 51.89 | 19.96 | 60.45 | −39.08 | −57.52 |
| IL-7 | 14.99 | 2.62 | 11.50 | −34.79 | −4.95 |
| IL-10 | 23.45 | −23.99 | 31.12 | 10.63 | −12.68 |
| IL-12β p40 | 52.78 | 52.96 | 47.85 | 34.81 | 29.89 |
| IL-12 p70 | 18.31 | 8.68 | 19.89 | −8.64 | −1.68 |
| IL-13 | 11.78 | −0.15 | 13.06 | 2.20 | 11.96 |
| IL-15 | −5.60 | −15.38 | −15.19 | −16.82 | 5.39 |
| IL-17 | 0.08 | 11.09 | 17.24 | 0.38 | −64.16 |
| IP-10 | 26.86 | −31.27 | 44.13 | 9.27 | −29.75 |
| KC | 47.26 | 7.91 | 40.58 | 32.72 | −20.85 |
| LIF | 47.26 | 13.35 | 31.07 | 3.06 | −33.26 |
| MCP-1 | 47.55 | −46.90 | 42.65 | 0.75 | 0.50 |
| M-CSF | 26.20 | −5.76 | 6.38 | 9.03 | −6.47 |
| MIG | 12.78 | −27.72 | −4.22 | −23.26 | −38.95 |
| MIP-1α | 47.53 | 16.16 | 51.59 | 11.22 | 2.59 |
| MIP-1β | 41.49 | 26.46 | 55.30 | 41.69 | 11.50 |
| MIP-2 | 53.95 | 35.52 | 47.72 | 18.84 | 8.33 |
| RANTES | 36.70 | −38.12 | 32.12 | 38.64 | −42.77 |
| TNF-α | 33.31 | −0.67 | 26.59 | 24.13 | −7.79 |
| AVERAGE SUPPRESSION | 20.24 | 2.77 | 19.68 | 3.36 | −16.51 |

24 out of the 32 analyzed cytokines were induced two-fold by LPS. Of the 24 cytokines whose expression level was induced two-fold or greater by LPS, the levels of 23 of these cytokines were suppressed or reduced by at least one of the doses of omega fatty acids used in the study. Because the greatest suppression was achieved by the highest dose of the omega fatty acids used, the study was repeated using higher doses of the omega fatty acids. This repeated study is Study 2, below.

Study 2: 1875 mg/kg, 625 mg/kg, 187.5 mg/kg, and 62.5 mg/kg of Omega Fatty Acids 28 female C57BL/6 mice that weighed approximately 20 g each were allowed to acclimate with unlimited access to food and water. On the day of the study, the mice were weighed and split into six groups of four mice each so that the average weight of each group was as close as possible to each other. The six groups included: (1) Untreated (0.1 mL injection of MCT oil, followed 1 hour later by a 0.1 mL injection of PBS instead of LPS); (2) LPS control (0.1 mL injection of MCT oil, followed 1 hour later by a 0.1 mL injection of LPS in PBS); (3) 1,875 of mg/kg omega fatty acid treatment groups (0.1 mL injection of omega fatty acids in MCT oil, followed 1 hour later by a 0.1 mL injection of LPS in PBS); (4) 625 of mg/kg omega fatty acid treatment groups (0.1 mL injection of omega fatty acids in MCT oil, followed 1 hour later by a 0.1 mL injection of LPS in PBS); (5) 187.5 of mg/kg omega fatty acid treatment groups (0.1 mL injection of omega fatty acids in MCT oil, followed 1 hour later by a 0.1 mL injection of LPS in PBS); and (6) 62.5 of mg/kg omega fatty acid treatment groups (0.1 mL injection of omega fatty acids in MCT oil, followed 1 hour later by a 0.1 mL injection of LPS in PBS)

The omega fatty acids were dosed at 1,875 mg/kg or 37.5 mg per 20 g mouse, 625.0 mg/kg or 12.5 mg per 20 g mouse, 187.5 mg/kg or 3.75 mg per 20 g mouse and 62.5.0 mg/kg or 1.25 mg per 20 g mouse. The omega fatty acids were diluted with MCT oil to create 375.00 mg/mL, 125.00 mg/mL, 37.5 mg/mL and 12.5 mg/mL solutions for the 0.1 mL injections. The LPS was dosed at 0.1 mg/kg or 0.002 mg per 20 g mouse. The LPS was prepared as a 0.02 mg/mL solution in PBS for a 0.1 mL injection. The results of Study 2 are given in Table 19, below.

TABLE 19

| Percent suppression of elevated cytokine levels by different doses of omega fatty acids | | | | |
| --- | --- | --- | --- | --- |
| Cytokines | 1,875 mg/kg | 625 mg/kg | 187.5 mg/kg | 62.5 mg/kg |
| GM-CSF | 3.58 | 17.25 | −2.65 | −44.93 |
| IFNγ | −12.68 | 3.26 | 31.07 | −33.22 |
| IL-3 | 74.37 | 70.81 | 60.66 | 60.66 |
| IL-6 | 72.24 | 56.46 | 37.45 | −14.37 |
| IL-10 | 7.80 | −0.82 | −13.84 | 35.46 |
| IL-12β p40 | −17.93 | −19.00 | 24.19 | −52.87 |
| IL-15 | 35.58 | 22.63 | 42.67 | 18.41 |
| IL-17 | 34.82 | 30.99 | 49.98 | 4.52 |
| IP-10 | 60.53 | 69.91 | −100.00 | 86.66 |
| KC | 27.64 | 31.04 | 26.22 | −0.91 |
| LIF | 30.29 | 30.20 | 36.08 | 2.71 |
| MCP-1 | 29.79 | 9.70 | 22.63 | 6.85 |
| M-CSF | 28.19 | 18.69 | −17.85 | 5.37 |
| MIG | −1.36 | 1.68 | −11.96 | 0.97 |
| MIP-1α | 47.28 | 32.51 | 58.55 | 40.51 |
| MIP-1β | 44.04 | 50.59 | 41.33 | 48.59 |
| MIP-2 | 36.98 | 10.93 | 26.01 | −28.08 |
| RANTES | −4.36 | 17.55 | 19.96 | −6.81 |
| TNF-α | 24.60 | −3.88 | 11.15 | 7.63 |
| AVERAGE SUPPRESSION | 27.44 | 23.71 | 17.98 | 7.22 |

Figure 4:
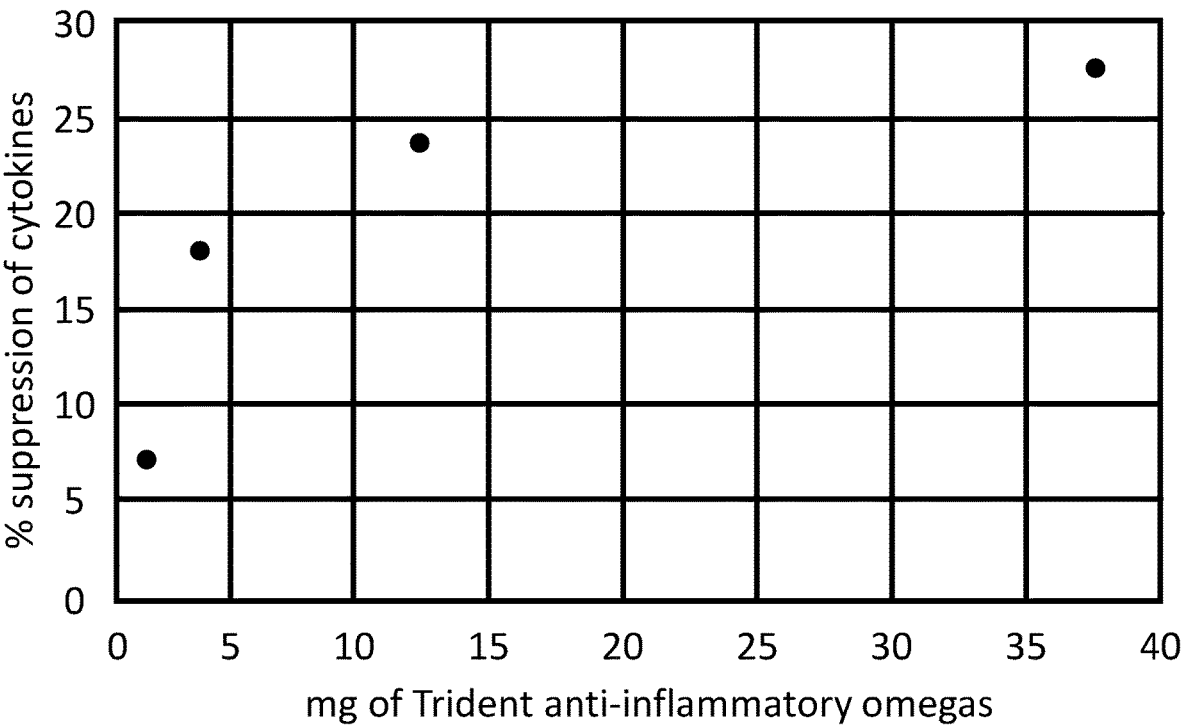
FIG. 4 depicts a graph of anti-inflammatory omega fatty acids dosed per mouse versus the percent suppression of cytokines as observed in Example 6B.

19 out of the 32 analyzed cytokines were induced two-fold by LPS. Of the 19 cytokines whose expression level was induced two fold or greater by LPS, the levels of all 19 of cytokines were suppressed or reduced by at least one of the doses of omega fatty acids used in the study. The highest possible dose of the omega fatty acids that could be used in mice showed the highest level of suppression. FIG. 4 depicts a graph of anti-inflammatory omega fatty acids dosed per mouse versus the percent suppression of cytokines that is observed reveals that the anti-inflammatory effect starts to saturate at around the dose of 12.5 mg anti-inflammatory omega fatty acids per mouse. Table 20, below, shows the suppression increase percentage that occurs as the dose of anti-inflammatory omega fatty acids is increased per mouse.

TABLE 20

Omega fatty acid dosage vs. suppression increase

| Omega Fatty Acid Dosage (mg) | Suppression Percentage | Percentage Increase |
|---|---|---|
| 1.25 | 7.22 | n/a |
| 3.75 | 17.98 | 149 |
| 12.5 | 23.71 | 32 |
| 37.5 | 27.44 | 16 |

Example 6C: Determining the Dosing Efficacy of Cannabinoid-Omega Fatty Acid Compositions in Mice Using the Mouse LPS Cytokine Animal Model In this study, the effects of combining 1:1 CBD:CBDA with anti-inflammatory omega unsaturated fatty acids using the mouse LPS cytokine animal model were examined. Because the most efficacious dose of 1:1 CBD:CBDA versus the anti-inflammatory omega unsaturated fatty acids varied so greatly in the mouse LPS cytokine animal model (i.e., 0.25-0.5 mg/kg or 0.005-0.01 mg per 20 g mouse for 1:1 CBD:CBDA and 1,875 mg/kg or 37.5 mg per 20 g mouse for omega unsaturated fatty acids), multiple combinations of various doses of the omega unsaturated fatty acids and various doses of 1:1 CBD:CBDA were examined. Because 1:1 CBD:CBDA, omega fatty acids and dexamethasone are soluble in MCT oil, MCT oil was used to prepare the solutions for these studies.

Study 1: Comparing 0.5 mg/kg 1:1 CBD:CBDA, 1,875 mg/kg Omega Fatty Acids, 187.5 mg/kg Omega Fatty Acids, 0.5 mg/kg 1:1 CBD:CBDA Combined with 1,875 mg/kg Omega Fatty Acids and 0.5 mg/kg 1:1 CBD:CBDA Combined with 187.5 mg/kg Omega Fatty Acids.

In the first study, a high dose (1,875 mg/kg) of omega unsaturated fatty acids and a low dose dose (187.5 mg/kg) of omega unsaturated fatty acids combined with 0.5 mg/kg 1:1 CBD:CBDA were used.

32 female C57BL/6 mice that weighed approximately 20 g each were allowed to acclimate for one week with unlimited access to food and water. On the day of the study, the mice were weighed and split into eight groups of four mice each so that the average weight of each group was as close as possible to each other. The groups included: (1) Untreated (0.1 mL injection of MCT oil, followed 1 hour later by a 0.1 mL injection of PBS instead of LPS); (2) LPS (0.1 mL injection of MCT oil, followed 1 hour later by a 0.1 mL injection of LPS in PBS); (3) LPS plus 0.01 mg dexamethasone in MCT oil (0.1 mL injection of 100% MCT oil containing 0.1 mg/mL dexamethasone, followed 1 hour later by a 0.1 mL injection of LPS in PBS); (4) LPS plus 0.01 mg 1:1 CBD:CBDA in MCT oil (0.1 mL injection of 100% MCT oil containing 0.1 mg/mL 1:1 CBD:CBDA, followed 1 hour later by a 0.1 mL injection of LPS in PBS); (5) LPS plus 3.750 mg omega fatty acids (0.1 mL injection of 37.50 mg/mL omega fatty acids diluted in MCT oil, followed 1 hour later by a 0.1 mL injection of LPS in PBS); (6) LPS plus 3.750 mg omega fatty acids/0.01 mg 1:1 CBD:CBDA (0.1 mL injection of 37.50 mg/mL omega fatty acids/0.1 mg/mL 1:1 CBD:CBDA diluted in MCT oil, followed 1 hour later by a 0.1 mL injection of LPS in PBS); (7) LPS plus 37.50 mg omega fatty acids (0.1 mL injection of 375.00 mg/mL omega fatty acids diluted in MCT oil, followed 1 hour later by a 0.1 mL injection of LPS in PBS); and (8) LPS plus 37.50 mg omega fatty acids/0.01 mg 1:1 CBD:CBDA (0.1 mL injection of 375.00 mg/mL omega fatty acids/0.1 mg/mL 1:1 CBD:CBDA diluted in MCT oil, followed 1 hour later by a 0.1 mL injection of LPS in PBS). The results of study 1 are shown in Table 21, below.

TABLE 21

Percent suppression of elevated cytokine levels by different doses of the omega fatty acids with or without 0.5 mg/kg 1:1 CBD:CBDA

| Cytokines | DXM | 0.5 mg/kg CBD:CBDA only | 187.5 mg/kg omegas only | 187.5 mg/kg omegas plus 0.5 mg/kg CBD:CBDA | 1,875.0 mg/kg omegas only | 1,875.0 mg/kg omegas plus 0.5 mg/kg CBD:CBDA |
|---|---|---|---|---|---|---|
| GM-CSF | −0.14 | −9.42 | −9.71 | 3.74 | 85.84 | 43.21 |
| IFNγ | −41.63 | 24.80 | −19.57 | 9.82 | 17.39 | 18.60 |
| IL-1β | 19.75 | 16.92 | 10.39 | 24.02 | 33.91 | 32.55 |
| IL-6 | 64.76 | 71.03 | 75.52 | 67.78 | 71.12 | 68.63 |
| IL-10 | 19.59 | −25.10 | 18.25 | 4.41 | −1.26 | −6.98 |
| IL-12β p40 | 39.02 | 37.47 | 52.16 | 48.98 | 50.41 | 56.96 |
| IL-12 p70 | 10.64 | 33.64 | −1.21 | −22.78 | −46.84 | −8.74 |
| IL-15 | 26.30 | 26.61 | 18.39 | 30.59 | −77.33 | 32.56 |
| IL-17 | 49.77 | 49.47 | 26.17 | −25.57 | 17.25 | 11.04 |
| IP-10 | 24.44 | 16.25 | 37.03 | 5.29 | −3.36 | 30.30 |
| KC | 40.63 | 66.40 | 59.81 | 65.95 | 67.06 | 59.51 |
| LIF | 29.55 | 10.98 | 38.64 | 35.61 | −21.59 | 7.95 |
| MCP-1 | 26.32 | 46.58 | 58.42 | 45.63 | 24.70 | 53.42 |
| MIG | 3.78 | −1.60 | −0.28 | 7.91 | −14.34 | 20.23 |
| MIP-1α | 26.86 | 36.00 | 39.49 | 32.99 | 62.47 | 51.57 |
| MIP-1β | 5.51 | 35.04 | 43.26 | 43.82 | 43.62 | 48.22 |
| MIP-2 | 34.16 | 31.98 | 33.75 | 26.04 | 34.40 | 33.07 |
| RANTES | −13.70 | 10.04 | 26.00 | −9.42 | −11.83 | 13.33 |
| TNF-α | 26.92 | 35.05 | 36.95 | 33.79 | 29.69 | 37.62 |
| AVERAGE SUPPRESSION | 20.66 | 26.95 | 28.60 | 22.56 | 19.02 | 31.74 |

20 out of the 32 analyzed cytokines were induced two-fold by LPS. Because the purpose of this experiment was to evaluate the effectiveness of combining 1:1 CBD:CBDA and the anti-inflammatory omega fatty acids, only cytokines that could be suppressed by one of the anti-inflammatory agents used in this study were considered. 19 out of the 20 cytokines whose expression level was induced-two fold or greater by LPS met this criteria.

In this study, the highest suppression of the cytokine levels was observed with the combination of 0.5 mg/kg 1:1 CBD:CBDA and 1,875 mg/kg of the anti-inflammatory omega fatty acids. The suppression achieved by the combination of 0.5 mg/kg 1:1 CBD:CBDA and 1,875 mg/kg of the anti-inflammatory omega fatty acids was significantly higher than that of the 0.5 mg/kg 1:1 CBD:CBDA or 1,875 mg/kg of the anti-inflammatory omega fatty acids alone. The control dexamethasone, which is abbreviated DXM in Table 21, caused a 20.66% decrease in the cytokine expression levels.

Study 2: Comparing 0.5 mg/kg 1:1 CBD:CBDA, 1,875 mg/kg Omega Fatty Acids, 625 mg/kg Omega Fatty Acids, 187.5 mg/kg Omega Fatty Acids, 0.5 mg/kg 1:1 CBD:CBDA Combined with 1,875 mg/kg Omega Fatty Acids, 0.5 mg/kg 1:1 CBD:CBDA Combined with 625 mg/kg Omega Fatty Acids and 0.5 mg/kg 1:1 CBD:CBDA Combined with 187.5 mg/kg Omega Fatty Acids.

In the second study, a high dose (1,875 mg/kg) of omega unsaturated fatty acids, an intermediate dose (625 mg/kg) of omega unsaturated fatty acids and a low dose dose (187.5 mg/kg) of omega unsaturated fatty acids combined with 0.5 mg/kg 1:1 CBD:CBDA were used.

injection of MCT oil, followed 1 hour later by a 0.1 mL injection of LPS in PBS); (3) LPS plus 0.01 mg dexamethasone in MCT oil (0.1 mL injection of 100% MCT oil containing 0.1 mg/mL dexamethasone, followed 1 hour later by a 0.1 mL injection of LPS in PBS); (4) LPS plus 0.01 mg 1:1 CBD:CBDA in MCT oil (0.1 mL injection of 100% MCT oil containing 0.1 mg/mL 1:1 CBD:CBDA, followed 1 hour later by a 0.1 mL injection of LPS in PBS); (5) LPS plus 3.750 mg omega fatty acids (0.1 mL injection of 37.50 mg/mL omega fatty acids diluted in MCT oil, followed 1 hour later by a 0.1 mL injection of LPS in PBS); (6) LPS plus 3.750 mg omega fatty acids/0.01 mg 1:1 CBD:CBDA (0.1 mL injection of 37.50 mg/mL omega fatty acids/0.1 mg/mL 1:1 CBD:CBDA diluted in MCT oil, followed 1 hour later by a 0.1 mL injection of LPS in PBS); (7) LPS plus 12.50 mg omega fatty acids (0.1 mL injection of 125.00 mg/mL omega fatty acids diluted in MCT oil, followed 1 hour later by a 0.1 mL injection of LPS in PBS); and (8) LPS plus 12.50 mg omega fatty acids/0.01 mg 1:1 CBD:CBDA (0.1 mL injection of 125.00 mg/mL omega fatty acids/0.1 mg/mL 1:1 CBD:CBDA diluted in MCT oil, followed 1 hour later by a 0.1 mL injection of LPS in PBS). (9) LPS plus 37.50 mg omega fatty acids (0.1 mL injection of 375.00 mg/mL omega fatty acids diluted in MCT oil, followed 1 hour later by a 0.1 mL injection of LPS in PBS); and (10) LPS plus 37.50 mg omega fatty acids/0.01 mg 1:1 CBD:CBDA (0.1 mL injection of 375.00 mg/mL omega fatty acids/0.1 mg/mL 1:1 CBD:CBDA diluted in MCT oil, followed 1 hour later by a 0.1 mL injection of LPS in PBS). The results of study 2 are shown in Table 22, below.

TABLE 22

| | | | | | | | | |
|---|---|---|---|---|---|---|---|---|
| Percent suppression of elevated cytokine levels by different doses of the omega fatty acids with or without 0.5 mg/kg 1:1 CBD:CBDA | | | | | | | | |
| Cytokines | DXM | 0.5 mg/kg CBD:CBDA only | 187.5 mg/kg omegas only | 187.5 mg/kg omegas plus 0.5 mg/kg CBD:CBDA | 625.0 mg/kg omegas only | 625.0 mg/kg omegas plus 0.5 mg/kg CBD:CBDA | 1,875.0 mg/kg omegas only | 1,875.0 mg/kg omegas plus 0.5 mg/kg CBD:CBDA |
| G-CSF | −1.83 | −2.14 | 6.62 | 24.11 | 7.72 | 3.71 | −3.05 | −1.80 |
| GM-CSF | 26.4 | 11.96 | 20.48 | −0.21 | 19.42 | 40.79 | 18.41 | 4.97 |
| IFNγ | 70.28 | 42.65 | −8.53 | 17.64 | 33.40 | 48.85 | −3.71 | 61.90 |
| IL-6 | 76.63 | 44.61 | 55.17 | 57.64 | 56.82 | 49.11 | 38.42 | 80.85 |
| IL-7 | 31.25 | 23.75 | 0.63 | −0.63 | 74.38 | 51.25 | −68.13 | 23.75 |
| IL-10 | 24.07 | 8.19 | 54.82 | 39.62 | 20.64 | 48.56 | −27.62 | 65.69 |
| IL-12β p40 | 56.90 | 16.99 | 16.10 | 41.34 | 49.91 | 41.88 | 27.83 | 47.44 |
| IL-15 | 42.45 | −97.03 | 45.94 | 43.62 | 22.00 | 21.19 | 39.94 | 21.38 |
| IL-17 | 64.04 | 2.50 | 29.21 | 45.07 | 32.21 | 53.68 | 49.31 | 8.24 |
| IP-10 | 44.62 | −9.02 | 25.85 | −44.42 | 12.43 | 15.17 | −10.41 | 32.73 |
| KC | 79.04 | 42.86 | 70.58 | 62.57 | 56.69 | 54.13 | 37.30 | 82.46 |
| LIF | 51.34 | 23.92 | 34.95 | 38.44 | 27.96 | 36.29 | 16.13 | 42.20 |
| MCP-1 | 57.38 | 53.10 | 55.69 | 65.09 | 57.82 | 66.81 | 55.62 | 80.49 |
| M-CSF | 46.02 | 30.98 | 54.94 | 41.28 | 30.75 | 37.27 | 9.37 | 54.24 |
| MIG | 20.57 | −10.71 | −3.38 | −4.95 | −5.64 | −12.59 | −20.83 | −4.00 |
| MIP-1α | 59.54 | 30.14 | 50.60 | 46.85 | 47.69 | 52.47 | 47.11 | 71.72 |
| MIP-1β | 27.89 | 27.15 | 58.71 | 46.59 | 37.78 | 35.19 | 42.84 | 68.45 |
| RANTES | 46.25 | 7.13 | 18.51 | 32.70 | 22.59 | 21.77 | 16.91 | 47.46 |
| TNF-α | 61.44 | 18.15 | 35.28 | 32.22 | 31.54 | 41.05 | 43.40 | 51.36 |
| AVERAGE SUPPRESSION | 46.54 | 13.96 | 32.75 | 30.77 | 33.48 | 37.19 | 14.32 | 44.19 |

40 female C57BL/6 mice that weighed approximately 20 g each were allowed to acclimate for one week with unlimited access to food and water. On the day of the study, the mice were weighed and split into ten groups of four mice each so that the average weight of each group was as close as possible to each other. The groups included: (1) Untreated (0.1 mL injection of MCT oil, followed 1 hour later by a 0.1 mL injection of PBS instead of LPS); (2) LPS (0.1 mL 19 out of the 32 analyzed cytokines were induced two-fold by LPS. Because the purpose of this experiment was to evaluate the effectiveness of combining 1:1 CBD:CBDA and the anti-inflammatory omega fatty acids, only cytokines that could be suppressed by one of the anti-inflammatory agents used in this study were considered. 19 out of the 19 cytokines whose expression level was induced-two fold or greater by LPS met these criteria.

In this study, the highest suppression of the cytokine levels was observed with the combination of 0.5 mg/kg 1:1 CBD:CBDA and 1,875 mg/kg of the anti-inflammatory omega fatty acids and the suppression achieved by the combination of 0.5 mg/kg 1:1 CBD:CBDA and 1,875 mg/kg of the anti-inflammatory omega fatty acids was significantly higher than that of the 0.5 mg/kg 1:1 CBD:CBDA or 1,875 mg/kg of the anti-inflammatory omega fatty acids alone. The control dexamethasone, which is abbreviated DXM in Table 22, caused a 46.54% decrease in the cytokine expression levels.

Study 3: Comparing 0.25 mg/kg 1:1 CBD:CBDA, 1,875 mg/kg Omega Fatty Acids, 625 mg/kg Omega Fatty Acids, 187.5 mg/kg Omega Fatty Acids, 0.25 mg/kg 1:1 CBD:CBDA Combined with 1,875 mg/kg Omega Fatty Acids, 0.25 mg/kg 1:1 CBD:CBDA Combined with 625 mg/kg Omega Fatty Acids and 0.25 mg/kg 1:1 CBD:CBDA Combined with 187.5 mg/kg Omega Fatty Acids.

In the third study, a high dose (1,875 mg/kg) of omega unsaturated fatty acids, an intermediate dose (625 mg/kg) of omega unsaturated fatty acids and a low dose dose (187.5 mg/kg) of omega unsaturated fatty acids combined with 0.25 mg/kg 1:1 CBD:CBDA were used.

40 female C57BL/6 mice that weighed approximately 20 g each were allowed to acclimate for one week with unlimited access to food and water. On the day of the study, the mice were weighed and split into ten groups of four mice by a 0.1 mL injection of LPS in PBS); (4) LPS plus 0.005 mg 1:1 CBD:CBDA in MCT oil (0.1 mL injection of 100% MCT oil containing 0.05 mg/mL 1:1 CBD:CBDA, followed 1 hour later by a 0.1 mL injection of LPS in PBS); (5) LPS plus 3.750 mg omega fatty acids (0.1 mL injection of 37.50 mg/mL omega fatty acids diluted in MCT oil, followed 1 hour later by a 0.1 mL injection of LPS in PBS); (6) LPS plus 3.750 mg omega fatty acids/0.005 mg 1:1 CBD:CBDA (0.1 mL injection of 37.50 mg/mL omega fatty acids/0.05 mg/mL 1:1 CBD:CBDA diluted in MCT oil, followed 1 hour later by a 0.1 mL injection of LPS in PBS); (7) LPS plus 12.50 mg omega fatty acids (0.1 mL injection of 125.00 mg/mL omega fatty acids diluted in MCT oil, followed 1 hour later by a 0.1 mL injection of LPS in PBS); and (8) LPS plus 12.50 mg omega fatty acids/0.005 mg 1:1 CBD:CBDA (0.1 mL injection of 125.00 mg/mL omega fatty acids/0.05 mg/mL 1:1 CBD:CBDA diluted in MCT oil, followed 1 hour later by a 0.1 mL injection of LPS in PBS). (9) LPS plus 37.50 mg omega fatty acids (0.1 mL injection of 375.00 mg/mL omega fatty acids diluted in MCT oil, followed 1 hour later by a 0.1 mL injection of LPS in PBS); and (10) LPS plus 37.50 mg omega fatty acids/0.005 mg 1:1 CBD:CBDA (0.1 mL injection of 375.00 mg/mL omega fatty acids/0.05 mg/mL 1:1 CBD:CBDA diluted in MCT oil, followed 1 hour later by a 0.1 mL injection of LPS in PBS). The results of study 2 are shown in Table 23, below.

TABLE 23

Percent suppression of elevated cytokine levels by different doses of the omega fatty acids with or without 0.25 mg/kg 1:1 CBD:CBDA

| Cytokines | DXM | 0.25 mg/kg CBD:CBDA only | 187.5 mg/kg omegas only | 187.5 mg/kg omegas plus 0.25 mg/kg CBD:CBDA | 625.0 mg/kg omegas only | 625.0 mg/kg omegas plus 0.25 mg/kg CBD:CBDA | 1,875.0 mg/kg omegas only | 1,875.0 mg/kg omegas plus 0.25 mg/kg CBD:CBDA |
|---|---|---|---|---|---|---|---|---|
| Eotaxin | 7.26 | −0.77 | 26.57 | 8.57 | 8.81 | 19.73 | 6.91 | 35.73 |
| IFNγ | 44.52 | 40.05 | −72.07 | 28.18 | −30.02 | 46.03 | 32.92 | −20.53 |
| IL-1β | 35.53 | 19.93 | −41.64 | 21.16 | 0.29 | 16.28 | 47.65 | 16.92 |
| IL-2 | −9.46 | 21.32 | 2.83 | −5.85 | −17.02 | 6.88 | 4.83 | 4.83 |
| IL-6 | 85.95 | 62.49 | 50.46 | 69.01 | 76.74 | 86.89 | 73.32 | 82.41 |
| IL-7 | 96.66 | 96.66 | −64.29 | 96.66 | 66.13 | 43.20 | 96.66 | 61.18 |
| IL-10 | 57.41 | 28.19 | 29.74 | 38.78 | 46.21 | 70.90 | 38.49 | 17.62 |
| IL-12β p40 | 54.79 | 44.74 | 8.67 | 10.86 | 15.63 | 44.87 | 34.76 | −50.20 |
| IL-12β p70 | −51.07 | 41.23 | 34.28 | 24.07 | −9.86 | 37.48 | −2.19 | 3.33 |
| IL-13 | 11.39 | 0.90 | 0.28 | 27.84 | 23.95 | 28.16 | 16.17 | 9.38 |
| IL-15 | −13.42 | 4.36 | −7.23 | 13.47 | 7.34 | 59.55 | 39.30 | −32.33 |
| IL-17 | 63.75 | 35.44 | 10.38 | −1.69 | 40.38 | 51.63 | 41.31 | 32.56 |
| IP-10 | 42.02 | 43.61 | 46.15 | 30.27 | 50.82 | 62.48 | 49.75 | 64.66 |
| KC | 60.10 | 17.48 | 26.75 | 25.58 | 27.43 | 51.48 | 38.38 | 63.61 |
| LIF | 47.18 | 58.05 | 42.37 | 40.99 | 54.47 | 71.53 | 43.88 | 57.77 |
| MCP-1 | 57.29 | 55.57 | 35.72 | 63.12 | 63.27 | 65.87 | 53.12 | 35.98 |
| M-CSF | 28.01 | 46.68 | 31.52 | 22.92 | −3.14 | −20.83 | 43.31 | −6.04 |
| MIG | −0.29 | 3.25 | 15.89 | 7.65 | −4.13 | 10.51 | 20.98 | 44.15 |
| MIP-1α | 47.13 | 28.39 | 35.74 | 37.09 | 49.71 | 64.67 | 50.02 | 46.93 |
| MIP-1β | 34.67 | −8.15 | 7.45 | 15.49 | 24.42 | 37.38 | 32.26 | 22.47 |
| MIP-2 | 37.57 | 48.44 | −16.86 | 21.15 | 29.55 | 45.49 | 21.59 | 9.57 |
| RANTES | 37.87 | 5.72 | 19.89 | 0.09 | −16.82 | 34.70 | −18.67 | 32.70 |
| TNF-α | 51.43 | 27.41 | −2.12 | 26.43 | 34.78 | 43.19 | 38.23 | 44.26 |
| VEGF | 75.98 | −100.00 | −62.01 | 1.80 | −18.94 | 60.11 | 44.44 | −43.17 |
| AVERAGE SUPPRESSION | 37.59 | 25.87 | 6.60 | 25.99 | 21.67 | 43.26 | 35.31 | 22.24 | each so that the average weight of each group was as close as possible to each other. The groups included: (1) Untreated (0.1 mL injection of MCT oil, followed 1 hour later by a 0.1 mL injection of PBS instead of LPS); (2) LPS (0.1 mL injection of MCT oil, followed 1 hour later by a 0.1 mL injection of LPS in PBS); (3) LPS plus 0.01 mg dexamethasone in MCT oil (0.1 mL injection of 100% MCT oil containing 0.1 mg/mL dexamethasone, followed 1 hour later 24 out of the 32 analyzed cytokines were induced two-fold by LPS. Because the purpose of this experiment was to evaluate the effectiveness of combining 1:1 CBD:CBDA and the anti-inflammatory omega fatty acids, only cytokines that could be suppressed by one of the anti-inflammatory agents used in this study were considered. 24 out of the 24 cytokines whose expression level was induced-two fold or greater by LPS met these criteria.

In this study, the highest suppression of the cytokine levels was observed with the combination of 0.25 mg/kg 1:1 CBD:CBDA and 625 mg/kg of the anti-inflammatory omega fatty acids and the suppression achieved by the combination of 0.25 mg/kg 1:1 CBD:CBDA and 625 mg/kg of the anti-inflammatory omega fatty acids was significantly higher than that of the 0.25 mg/kg 1:1 CBD:CBDA or 625 mg/kg of the anti-inflammatory omega fatty acids alone. The control dexamethasone, which is abbreviated DXM in Table 23, caused a 37.59% decrease in the cytokine expression levels.

Collectively, the results of the three studies that examined combining 1:1 CBD:CBDA with anti-inflammatory omega fatty acids were very consistent. In all three studies, the maximal suppression of increased cytokine levels was achieved by a combination of 1:1 CBD:CBDA and anti-inflammatory omega fatty acids, and that suppression was significantly greater than the suppression that could be achieved by 1:1 CBD:CBDA or the anti-inflammatory omega fatty acids alone. In study 1 and study 2, the greatest suppression with 0.5 mg/kg 1:1 CBD:CBDA was achieved with the combination of 1875 mg/kg omega fatty acids. In study 3, the greatest suppression with 0.25 mg/kg 1:1 CBD:CBDA was achieved with the combination of 625 mg/kg omega fatty acids. These results indicate that, in order to achieve a high anti-inflammatory effect, the levels of 1:1 CBD:CBDA and omega fatty acids should be optimized when combined and that results can be dependent on the concentrations used.

Example 6D: Examining the Efficacy of ALA, DHA, and EPA Omega-3 Unsaturated Fatty Acids as Anti-Inflammatory Agents Give the unexpected success of combining the 1:1 CBD:CBDA with anti-inflammatory omega unsaturated fatty acids from fish oil, further experimentation was performed to explore whether one of the most prevalent omega-3 fatty acids, ALA, DHA or EPA, was more effective as an anti-inflammatory agent. Because both the mono and triglyceride forms of DHA and EPA may be available, the further experimentation also explored whether the mono or triglyceride forms of DHA and EPA were more effective as anti-inflammatory agents.

36 female C57BL/6 mice that weighed approximately 20 g each were obtained and allowed to acclimate for one week after arrival with unlimited access to food and water. On the day of the study, the mice were weighed and split into eight groups of four mice each so that the average weight of each group was as close as possible to each other.

All of the omega fatty acid samples that were tested were diluted so the dose was 12.5 mg of total omega fatty acids per mouse. The dose of the control dexamethasone was 0.01 mg per mouse. The omega fatty acids samples tested included: (1) pollock oil, 456 mg/mL omega unsaturated fatty acids. The pollock oil contained a mixture of anti-inflammatory omega-3, omega-7 and omega-9 unsaturated fatty acids. The omega-3, omega-7 and omega-9 unsaturated fatty acids constituted 45.8%, 18.6% and 31.6%, respectively, of the omega fatty acids contained in the pollock oil. The DHA:EPA ratio was 0.67:1. The major omega unsaturated fatty acids found in most commercially utilized fish oils are DHA and EPA at a DHA:EPA ratio of 0.67:1 to 0.75:1, where EPA is in greater abundance than DHA. A 12.5 mg dose contained 1.72 mg of DHA and 2.58 mg of EPA in the triglyceride form. (2) Flaxseed oil, 656 mg/mL anti-inflammatory omega unsaturated fatty acids. The flaxseed oil contained a mixture of anti-inflammatory omega-3 and omega-9 unsaturated fatty acids. The omega-3 and omega-9 unsaturated fatty acids constituted 77.6% and 28.8%, respectively, of the anti-inflammatory omega fatty acids contained in the flaxseed oil. A 12.5 mg dose contained 9.7 mg of ALA in the triglyceride form. (3) Mono 2:1 DHA:EPA, 744 mg/mL omega-3 unsaturated fatty acids that were primarily DHA or EPA. A 12.5 mg dose contained 7.81 mg of DHA and 3.91 mg of EPA. The omega-3 unsaturated fatty acids were in the free mono form. (4) Mono 1:2 DHA:EPA, 604.5 mg/mL omega-3 unsaturated fatty acids that were primarily DHA or EPA. A 12.5 mg dose contained 3.85 mg of DHA and 7.69 mg of EPA. The omega-3 unsaturated fatty acids were in the free mono form. (5) Tri 2:1 DHA:EPA, 678.9 mg/mL omega-3 unsaturated fatty acids that were primarily DHA or EPA. A 12.5 mg dose contained 7.88 mg of DHA and 3.94 mg of EPA. The omega-3 unsaturated fatty acids were in the triglyceride form. (6) Tri 1:2 DHA:EPA, 678.9 mg/mL omega-3 unsaturated fatty acids that were primarily DHA or EPA. A 12.5 mg dose contained 3.60 mg of DHA and 7.19 mg of EPA. The omega-3 unsaturated fatty acids were in the triglyceride form.

The mice were divided into nine groups: (1) Untreated (0.1 mL injection of medium-chain triglyceride (MCT) oil, followed 1 hour later by a 0.1 mL injection of PBS instead of LPS); (2) LPS (0.1 mL injection of MCT oil, followed 1 hour later by a 0.1 mL injection of LPS in PBS); (3) LPS plus 0.01 mg dexamethasone in MCT oil (0.1 mL injection of 100% MCT oil containing 0.1 mg/mL dexamethasone, followed 1 hour later by a 0.1 mL injection of LPS in PBS); (4) LPS plus 12.50 mg omega fatty acids (0.1 mL injection of 125.00 mg/mL omega fatty acids diluted in MCT oil, followed 1 hour later by a 0.1 mL injection of LPS in PBS); (5) LPS plus 12.50 mg ALA omega-3 (0.1 mL injection of 125.00 mg/mL ALA omega-3 diluted in MCT oil, followed 1 hour later by a 0.1 mL injection of LPS in PBS); (6) LPS plus 12.50 mg mono 2:1 DHA:EPA omega-3 (0.1 mL injection of 125.00 mg/mL mono 2:1 DHA:EPA omega-3 diluted in MCT oil, followed 1 hour later by a 0.1 mL injection of LPS in PBS); (7) LPS plus 12.50 mg mono 1:2 DHA:EPA omega-3 (0.1 mL injection of 125.00 mg/mL mono 1:2 DHA:EPA omega-3 diluted in MCT oil, followed 1 hour later by a 0.1 mL injection of LPS in PBS); (8) LPS plus 12.50 mg tri 2:1 DHA:EPA omega-3 (0.1 mL injection of 125.00 mg/mL tri 2:1 DHA:EPA omega-3 diluted in MCT oil, followed 1 hour later by a 0.1 mL injection of LPS in PBS); and (9) LPS plus 12.50 mg tri 1:2 DHA:EPA omega-3 (0.1 mL injection of 125.00 mg/mL tri 1:2 DHA:EPA omega-3 diluted in MCT oil, followed 1 hour later by a 0.1 mL injection of LPS in PBS).

The results of the study are shown in Table 24, below.

TABLE 24

Percent suppression of elevated cytokine levels by tri ALA, mono 2:1 DHA:EPA, mono 1:2 DHA:EPA, tri 2:1 DHA:EPA, and tri 1:2 DHA:EPA

| Cytokines | DXM | Pollock oil | tri ALA | mono 2:1 DHA:EPA | mono 1:2 DHA:EPA | tri 2:1 DHA:EPA | tri 1:2 DHA:EPA |
|---|---|---|---|---|---|---|---|
| Eotaxin | 24.14 | 13.36 | 28.57 | 24.53 | −3.25 | 10.41 | 22.84 |
| G-CSF | 7.36 | −8.62 | −5.64 | −2.89 | −9.06 | 4.87 | −9.44 |
| IL-6 | 76.02 | 6.05 | −3.21 | 19.40 | 0.46 | 60.46 | 59.85 |
| IL-10 | 47.30 | 8.69 | 23.15 | 21.67 | 31.23 | 26.18 | 20.28 |
| IP-10 | 41.65 | 15.47 | 25.07 | 31.99 | 16.45 | 36.14 | 42.31 |
| KC | 56.41 | 50.93 | 37.70 | 34.62 | 58.59 | 52.77 | 57.68 |
| MCP-1 | 54.99 | 3.55 | 13.79 | 41.79 | −10.93 | 37.87 | 19.90 |
| MIG | 25.46 | 17.14 | 21.54 | 18.59 | 19.83 | 24.64 | 26.82 |
| MIP-1α | 55.47 | 36.00 | 39.79 | 41.50 | 47.16 | 54.38 | 59.89 |
| MIP-1β | 48.33 | 41.40 | 31.95 | 39.04 | 48.27 | 58.33 | 48.35 |
| RANTES | 39.58 | 6.61 | 2.17 | −10.64 | −3.21 | 5.78 | −8.15 |
| Average Suppression | 43.34 | 17.33 | 19.53 | 23.60 | 17.78 | 33.80 | 30.94 |

12 out of the 32 cytokines that were analyzed were induced two-fold by LPS. Of the 12 cytokines whose expression level was induced two-fold or greater by LPS, the levels of all 12 of these cytokines were suppressed or reduced by at least one of the combination of omega fatty acids that were used in this study. The control dexamethasone, which is abbreviated DXM in Table 24, caused a 43.34% decrease in the cytokine expression levels and indicated that the study worked as expected.

Table 25 shows the average percent suppression versus the major omega fatty acids that are present in the sample.

TABLE 25

Average suppression vs. major omega fatty acids

| Agent | % Suppression | Total ALA | Total DHA | Total EPA |
|---|---|---|---|---|
| Dexamethasone | 43.34% | — | — | — |
| Pollock oil | 17.33% | 0.16 mg | 1.72 mg | 2.58 mg |
| Tri ALA | 19.53% | 9.7 mg | — | — |
| Mono 2:1 DHA:EPA | 23.6% | — | 7.81 mg | 3.91 mg |
| Mono 1:2 DHA:EPA | 17.78% | — | 3.85 mg | 7.69 mg |
| Tri 2:1 DHA:EPA | 33.8% | — | 7.88 mg | 3.94 mg |
| Tri 1:2 DHA:EPA | 30.94% | — | 3.60 mg | 7.19 mg |

The study of Example 6D shows that DHA has the highest anti-inflammatory capability of the three omega-3 unsaturated fatty acids most commonly found in nature, ALA, DHA and EPA, and that the natural triglyceride form of DHA and EPA are more effective than the mono form of DHA and EPA.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

REFERENCES

Barrie N, Manolios N, 2017 The endocannabinoid system in pain and inflammation: Its relevance to rheumatic disease Eur J Rheumatol. 4:210-218.

Behrens E M, Koretzky G A (2017) Review: Cytokine storm syndrome: Looking toward the precision medicine era. Arthritis Rheumatol. 6:1135-1143.

Bergamaschi M M, Queiroz R H, Zuardi A W, Crippa A S (2011) Safety and side effects of cannabidiol, a Cannabis sativa constituent. Curr Drug Saf. 6:237-249.

Byun S, Lee E, Lee K W (2017) Therapeutic implications of autophagy inducers in immunological disorders, infection, and cancer. Int J Mol Sci. 2017 18:1959.

Calder P C. 2017. Omega-3 fatty acids and inflammatory processes: from molecules to man. Biochem Soc Trans. 45:1105-1115.

Choi K S (2012) Autophagy and cancer. Exp Mol Med. 44:109-120.

Choi W H, Park H D, Baek S H (2008) Cannabidiol induces cytotoxicity and cell death via apoptotic pathway in cancer cell lines. Biomol Ther. 16:87-94.

Cochran F R, Finch-Arietta M B, 1989. Regulation of interleukin-1 beta and tumor necrosis factor secretion by the human monocytic leukemia cell line, THP-1. Agents Actions. 27:271-273.

Costa B, Colleoni M, Conti S, Parolaro D, Franke C, Trovato A E, Giagnoni G (2004) Oral anti-inflammatory activity of cannabidiol, a non-psychoactive constituent of Cannabis, in acute carrageenan-induced inflammation in the rat paw. Naunyn Schmiedebergs Arch Pharmacol. 369:294-299.

Di Marzo V, Piscitelli F (2015) The endocannabinoid system and its modulation by phytocannabinoids. Neurotherapeutics. 12:692-698.

Dinarello C A (2007) Historical review of cytokines. Eur J Immunol. 37:S34-S45.

Edinger A L, Thompson C B (2003) Defective autophagy leads to cancer. Cancer Cell. 4:422-424.

Field C, Allen J L, Friedman H, 1970. The immune response of mice to Serratia marcescens LPS or intact bacteria. J Immunol. 105:193-203.

Fine P G, Rosenfeld M J (2013) The endocannabinoid system, cannabinoids, and pain. Rambam Maimonides Med J. 4:e0022.

Fritsche K L. 2015. The science of fatty acids and inflammation. Adv Nutr. 6:293 S-301S.

Gerlach H (2016) Agents to reduce cytokine storm. F1000Research 2016, 5(F1000 Faculty Rev):2909.

Ghezzi P, Sipe J D, 1988. Dexamethasone modulation of LPS, IL-1, and TNF stimulated serum amyloid A synthesis in mice. Lymphokine Res. 7:157-166.

Hadam J, Aoun E, Clarke K, Wasko M C (2014) Managing risks of TNF inhibitors: an update for the internist. Cleve Clin J Med. 81:115-127.

Hosseinzadeh M, Nikseresht S, Khodagholi F, Naderi N, Maghsoudi N (2016) Cannabidiol post-treatment alleviates rat epileptic-related behaviors and activates hippocampal cell autophagy pathway along with antioxidant defense in chronic phase of pilocarpine-induced seizure. J Mol Neurosci. 58:432-440.

Husni A S, McCurdy C R, Radwan M M, Ahmed S A, Slade D, Ross S A, ElSohly M A, Cutler S J (2014) Evaluation of phytocannabinoids from high potency *Cannabis sativa* using in vitro bioassays to determine structure-activity relationships for cannabinoid receptor 1 and cannabinoid receptor 2. Med Chem Res. 23:4295-4300.

Jain A, Singh J A (2013) Harms of TNF inhibitors in rheumatic diseases: a focused review of the literature. Immunotherapy. 5:265-299.

Jameson S C, Masopust D (2018) What Is the Predictive Value of Animal Models for Vaccine Efficacy in Humans? Reevaluating the Potential of Mouse Models for the Human Immune System. Cold Spring Harb Perspect Biol. 2018 10:a029132.

Jiang G M, Tan Y, Wang H, Peng L, Chen H T, Meng X J, Li L L, Liu Y, Li W F, Shan H (2019) The relationship between autophagy and the immune system and its applications for tumor immunotherapy. Mol Cancer. 18:17.

Kenyon J, Liu W, Dalgleish A (2018) Report of objective clinical responses of cancer patients to pharmaceutical-grade synthetic cannabidiol. Anticancer Res. 38:5831-5835.

Kuballa P, Nolte W M, Castoreno A B, Xavier R J (2012) Autophagy and the immune system. Ann Rev Immunol. 30:611-646.

Liu D Z, Hu C M, Huang C H, Wey S P, Jan T R (2010) Cannabidiol attenuates delayed-type hypersensitivity reactions via suppressing T-cell and macrophage reactivity. Acta Pharmacol Sin. 31:1611-1617.

Lodzki M, Godin B, Rakou L, Mechoulam R, Gallily R, Touitou E (2003) Cannabidiol-transdermal delivery and anti-inflammatory effect in a murine model. J Control Release. 93:377-387.

Lukhele S T, Motadi L R (2016) Cannabidiol rather than *Cannabis sativa* extracts inhibit cell growth and induce apoptosis in cervical cancer cells. BMC Complement Altern Med. 16:335

Mato S, Victoria Sanchez-Gomez M, Matute C (2010) Cannabidiol induces intracellular calcium elevation and cytotoxicity in oligodendrocytes. Glia. 58:1739-1747.

McPartland J M, Duncan M, Di Marzo V, Pertwee R G (2015) Are cannabidiol and Δ9-tetrahydrocannabivarin negative modulators of the endocannabinoid system? A systematic review. Br J Pharmacol. 172:737-753.

Mestas J, Hughes C C W (2004) Of mice and not men: Differences between mouse and human immunology. J Immunol. 172:2731-2738.

Mukhtar E, Adhami V M, Khan N, Mukhtar H (2012) Apoptosis and autophagy induction as mechanism of cancer prevention by naturally occurring dietary agents. Curr Drug Targets. 13:1831-41.

Musolino C, Allegra A, Innao V, Allegra A G, Pioggia G, Gangemi S (2017) Inflammatory and anti-inflammatory equilibrium, proliferative and antiproliferative balance: the role of cytokines in multiple myeloma. Mediators Inflamm. 2017:1852517.

Nagarkatti P, Pandey R, Rieder S A, Hegde V L, Nagarkatti M (2009) Cannabinoids as novel anti-inflammatory drugs. Future Med Chem. 7:1333-1349.

Nair A B, Jacob S. 2016. A simple practice guide for dose conversion between animals and human. J Basic Clin Pharma. 7:27-31.

Nalbant S, Birlik A M (2017) Cytokines in rheumatoid arthritis (R A). In New developments in the pathogenesis of rheumatoid arthritis (Sakkas S, ed). IntechOpen, London, U K.

Nguyen H T, Lapaquette P, Bringer M A, Darfeuille-Michaud A (2013) Autophagy and Crohn's disease. J Innate Immun. 5:434-443.

Pandey R, Mousawy K, Nagarkatti M, Nagarkatti P (2009) Endocannabinoids and immune regulation. Pharmacol Res. 60:85-92.

Petrosino S, Verde R, Vaia M, Allarà M, Iuvone T, Di Marzo V (2018) Anti-inflammatory Properties of Cannabidiol, a Nonpsychotropic Cannabinoid, in Experimental Allergic Contact Dermatitis. J Pharmacol Exp Ther. 365:652-663.

Pripp A H, Stanišić M (2014) The correlation between pro- and anti-inflammatory cytokines in chronic subdural hematoma patients assessed with factor analysis. PLoS ONE. 9: e90149.

Rajan T S, Giacoppo S, Iori R, De Nicola G R, Grassi G, Pollastro F, Bramanti P, Mazzon E (2016) Anti-inflammatory and antioxidant effects of a combination of cannabidiol and moringin in LPS-stimulated macrophages. Fitoterapia. 112:104-115.

Rayburn E R, Ezell S J, Zhang R (2009) Anti-Inflammatory agents for cancer therapy. Mol Cell Pharmacol. 1:29-43.

Rosenthaler S, Pöhn B, Kolmanz C, Huu C N, Krewenka C, Huber A, Kranner B, Rausch W D, Moldzio R (2014) Differences in receptor binding affinity of several phytocannabinoids do not explain their effects on neural cell cultures. Neurotoxicol Teratol. 46:49-56.

Shin J-W, Seol I-C, Son C-G. 2010. Interpretation of animal dose and human equivalent dose for drug development. J Korean Orient Med. 31:1-7.

Showalter V M, Compton D R, Martin B R, Abood M E (1996) Evaluation of binding in a transfected cell line expressing a peripheral cannabinoid receptor (CB2): identification of cannabinoid receptor subtype selective ligands. J Pharmacol Exp Ther 278:989-999.

Simopoulos A P. 2002. Omega-3 fatty acids in inflammation and autoimmune diseases. J Am Coll Nutr. 21:495-505.

Sulé-Suso J, Watson N A, van Pittius D G, Jegannathen A (2019) Striking lung cancer response to self-administration of cannabidiol: A case report and literature review. SAGE Open Med Case Rep. 7:2050313X19832160.

Tisoncik J R, Korth M J, Simmons C P, Farrar J, Martin T R, Katze M G (2012) Into the eye of the cytokine storm. Microbiol Mol Biol Rev. 76:16-32.

Todoric J, Antonucci L, Karin M (2016) Targeting inflammation in cancer prevention and therapy. Cancer Prev Res (Phila). 12:895-905.

Wang F, Li B, Schall N, Wilhelm M, Muller S (2017) Assessing autophagy in mouse models and patients with systemic autoimmune diseases. Cells. 6:16.

Wang F, Muller S (2015) Manipulating autophagic processes in autoimmune diseases: a special focus on modulating chaperone-mediated autophagy, an emerging therapeutic target. Front Immunol. 6:252.

Wang W-Y, Tan M-S, Yu J-T, Tan L (2015) Role of pro-inflammatory cytokines released from microglia in Alzheimer's disease. Ann Transl Med. 3:136.

Wang L, Wang F-S, Gershwin M E (2015) Human autoimmune diseases; a comprehensive update. J Intern Med. 278:369-395.

Zhang J-M, An J (2007) Cytokines, inflammation and pain. Int Anesthesiol Clin. 45:27-37.

Zou S, Kumar U (2018) Cannabinoid receptors and the endocannabinoid system: signaling and function in the central nervous system. Int J Mol Sci. 19:833.

What is claimed is:

1. A pill, comprising:
a cannabinoid component consisting essentially of an approximately 1:1 equimolar mixture of CBD: CBDA; and
an omega fatty acid component,
wherein the weight-to-weight ratio of the cannabinoid component to the omega fatty acid component ranges from approximately 1:1,250 to approximately 1:3,750.

2. The pill of claim 1, wherein the omega fatty acid component comprises an anti-inflammatory omega unsaturated fatty acid.

3. The pill of claim 1, wherein:
the omega fatty acid component comprises a plurality of omega fatty acids; and
a majority of the omega fatty acids of the plurality of omega fatty acids is docosahexaenoic acid (DHA).

4. The pill of claim 1, wherein:
the omega fatty acid component comprises a plurality of omega fatty acids; and
a majority of the omega fatty acids of the plurality of omega fatty acids is eicosapentaenoic acid (EPA).

5. The pill of claim 1, wherein:
the omega fatty acid component comprises a plurality of omega fatty acids; and
a majority of the plurality of omega fatty acids is a mixture of DHA and EPA.

6. A method for at least one of reducing cytokine levels in vivo or in vitro or promoting antioxidant activity in a subject, comprising administering to the subject the pill of claim 1.

7. A method for treating or preventing cancer in a subject, comprising:
administering to the subject the pill of claim 1; and
administering an additional active agent to the subject, wherein the additional active agent comprises at least one of:

a chemotherapeutic agent;
a cytokine;
an antiviral agent;
an immune enhancer;
a tyrosine kinase inhibitor;
a protein kinase C (PKC) modulator;
a signal transduction inhibitor;
an antibiotic;
an antimicrobial agent;
a TLR agonist;
an inhibitor of IDO;
or an adjuvant.

8. A pill, comprising:
a cannabinoid component consisting essentially of an approximately 1:1 equimolar mixture of CBD: CBDA; and
an omega fatty acid component consisting essentially of a mixture of docosahexaenoic acid (DHA) and eicosapentaenoic acid (EPA)
wherein the weight-to-weight ratio of the cannabinoid component to the omega fatty acid component ranges from approximately 1:1,250 to approximately 1:3,750.

9. The pill of claim 8, further comprising a pharmaceutical carrier.

10. A method of administering the pill of claim 8, comprising administering an effective amount of the pill to a subject in need.

11. The method of claim 10, wherein the subject is a mammal.

12. The method of claim 11, wherein the mammal is a human.

13. A method for inducing autophagy in a patient in need thereof comprising administering to the patient an effective amount of a pill comprising: i) an approximately 1:1 equimolar mixture of CBD: CBDA; and ii) an omega fatty acid, wherein the wherein the weight-to-weight ratio of the 1:1 equimolar mixture of CBD: CBDA to the omega fatty acid is approximately 1:375.

14. The method of claim 13, wherein the induction of the autophagy treats or prevents cancer and/or reduces inflammation in the patient.

15. The pill of claim 1, wherein the pill comprises from about 250 mg to about 1,500 mg of the omega fatty acid component.

16. The pill of claim 1, wherein the pill comprises from about 500 mg to about 1,000 mg of the omega fatty acid component.

* * * * *